(12) United States Patent
Xu

(10) Patent No.: US 10,899,723 B2
(45) Date of Patent: Jan. 26, 2021

(54) HETEROCYCLIC CONTAINING CYCLOPROPYL FXR MODULATORS

(71) Applicant: Hepagene Therapeutics (HK) Limited, Wan Chai (HK)

(72) Inventor: Xiaodong Xu, Doylestown, PA (US)

(73) Assignee: Hepagene Therapeutics (HK) Limited, Wan Chai (HK)

( * ) Notice: Subject to any disclaimer, the term of this patent is extended or adjusted under 35 U.S.C. 154(b) by 0 days.

(21) Appl. No.: 16/343,748

(22) PCT Filed: Sep. 27, 2017

(86) PCT No.: PCT/US2017/053773
§ 371 (c)(1),
(2) Date: Apr. 19, 2019

(87) PCT Pub. No.: WO2018/075207
PCT Pub. Date: Apr. 26, 2018

(65) Prior Publication Data
US 2019/0248752 A1 Aug. 15, 2019

Related U.S. Application Data

(60) Provisional application No. 62/423,928, filed on Nov. 18, 2016.

(30) Foreign Application Priority Data

Oct. 22, 2016 (CN) .......................... 2016 1 0925882

(51) Int. Cl.
| | | |
|---|---|---|
| C07D 261/08 | (2006.01) |
| C07D 413/12 | (2006.01) |
| C07D 417/12 | (2006.01) |
| A61P 1/16 | (2006.01) |
| A61P 3/06 | (2006.01) |
| A61P 3/04 | (2006.01) |
| A61P 9/10 | (2006.01) |
| A61P 13/12 | (2006.01) |
| A61P 3/10 | (2006.01) |
| A61P 9/00 | (2006.01) |
| A61P 3/00 | (2006.01) |
| A61P 1/10 | (2006.01) |
| C07D 413/04 | (2006.01) |

(52) U.S. Cl.
CPC .............. *C07D 261/08* (2013.01); *A61P 1/10* (2018.01); *A61P 1/16* (2018.01); *A61P 3/00* (2018.01); *A61P 3/04* (2018.01); *A61P 3/06* (2018.01); *A61P 3/10* (2018.01); *A61P 9/00* (2018.01); *A61P 9/10* (2018.01); *A61P 13/12* (2018.01); *C07D 413/04* (2013.01); *C07D 413/12* (2013.01); *C07D 417/12* (2013.01)

(58) Field of Classification Search
CPC .. C07D 261/08; C07D 413/04; C07D 413/12; C07D 417/12
See application file for complete search history.

(56) References Cited

U.S. PATENT DOCUMENTS 8,952,042 B2 * 2/2015 Kremoser ............ C07D 249/06
514/378

FOREIGN PATENT DOCUMENTS

| EP | 2 289 883 A1 | 3/2011 |
| EP | 2 545 964 A1 | 1/2013 |
| WO | WO-2011/020615 A1 | 2/2011 |
| WO | WO-2016/096116 A1 | 6/2016 |
| WO | WO 2017/128896 * | 8/2017 |
| WO | WO-2017/128896 A1 | 8/2017 |

OTHER PUBLICATIONS

Raw machine translation for descrption of WO 2017/128896 of Publication Date Aug. 2017.*
International Search Report and Written Opinion in PCT/US2017/053773, dated Dec. 1, 2017 (11 pages).

* cited by examiner

*Primary Examiner* — Valerie Rodriguez-Garcia
(74) *Attorney, Agent, or Firm* — Foley & Lardner LLP

(57) ABSTRACT

The present technology is directed to compounds of formula (II) as well as compositions thereof and methods related to modulation of FXR. In particular, the present compounds and compositions may be used to treat FXR-mediated disorders and conditions, including, e.g., liver disease, hyperlipidemia, hypercholesteremia, obesity, metabolic syndrome, cardiovascular disease, gastrointestinal disease, and atherosclerosis, and renal disease.

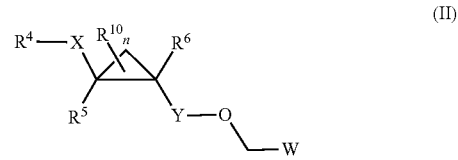

27 Claims, No Drawings

HETEROCYCLIC CONTAINING CYCLOPROPYL FXR MODULATORS

CROSS REFERENCE TO RELATED APPLICATIONS

This application claims priority to U.S. Provisional Application 62/423,928, filed Nov. 18, 2016, and Chinese Application 201610925882.1, filed Oct. 22, 2016, incorporated by reference in their entirities.

FIELD

The present technology is directed to compounds, compositions, and methods related to modulation of farnesoid X receptor (FXR). In particular, the present compounds and compositions may be used to treat FXR-mediated disorders and conditions, including, e.g., liver disease, hyperlipidemia, hypercholesteremia, obesity, metabolic syndrome, cardiovascular disease, gastrointestinal disease, atherosclerosis, and renal disease.

BACKGROUND

The Farnesoid X receptor (FXR, NR1H4) is an orphan member of the nuclear receptor gene family that is activated by farnesol metabolites (Forman et al. "Identification of a nuclear receptor that is activated by farnesol metabolites" *Cell* 1995, 81, 687-693; Seol et al. "Isolation of proteins that interact specifically with the retinoid X receptor: two novel orphan receptors" *Mol. Endocrinol.* 1995, 9, 72-85). FXR is highly expressed in the liver, gall bladder, intestine, kidney and adrenal glands.

Subsequently, bile acids were identified as natural ligands for FXR. Bile acid has many physiological functions and plays a critical role in the digestion, absorption, transportation, distribution of fat and lipid-soluble vitamins; maintain homeostasis of cholesterol and glucose. Through regulation of gene expression of bile acids, FXR serves as a key controller of bile acid homeostasis. Therefore, FXR modulation is expected to provide treatments for diseases such as cholestasis, liver fibrosis, liver cancer, atherosclerosis, diabetes and the like. FXR agonists were also reported as a treatment option for HBV infection (Radreau et al. "Reciprocal regulation of farnesoid X receptor a activity and hepatitis B virus replication in differentiated HepaRG cells and primary human hepatocytes" *FASEB J*, 2016, 30, 3146-3154).

In recent years, a variety of primary and secondary bile acids such as chenodeoxycholic acid (CDCA) that can activate FXR have been found. In 2002, Pellicciari et al. reported the first synthesis of highly active steroid FXR agonist, 6-ethyl-CDCA (Pellicciari et al. "6α-ethyl-chenodeoxycholic acid (6-ECDCA), a potent and selective FXR agonist endowed with anticholestatic activity" *J. Med. Chem.* 2002, 45, 3569-72). 6-EDCA, also known as obeticholic acid, is in clinical trials for treatment of NAFLD, NASH, liver cirrhosis and other liver conditions. It has been approved for treatment in the US for the treatment of primary biliary cholangitis. Thus, FXR modulators have been shown to serve to be therapeutically effective in a number of FXR-mediated diseases and disorders.

SUMMARY

The present technology provides compounds, compositions, and methods related to modulation of FXR. In one aspect, the present technology provides a compound according to formula I:

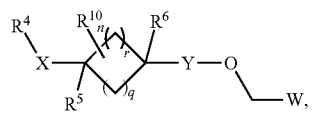

stereoisomers, and/or salts thereof; wherein
W is

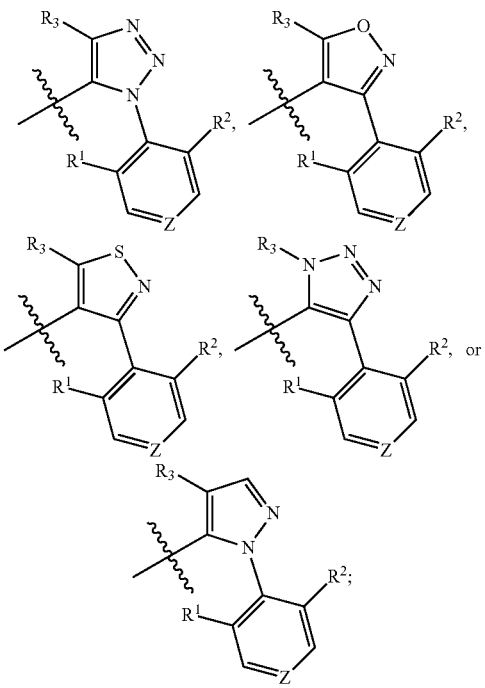

X is a substituted or unsubstituted aryl or heteroaryl group;
Y is a substituted or unsubstituted phenyl or pyridyl group;
Z is CH or N;
$R^1$ and $R^2$ are independently H, OH, halo, CN, carboxyl, $NR^aR^b$, or a substituted or unsubstituted alkyl, alkoxy, or hydroxyalkyl group;
$R^3$ is a substituted or unsubstituted alkyl or cycloalkyl group;
$R^4$ is CN, $SO_3H$, $CONR^aR^b$, $SO_2NR^aR^b$, $NHSO_2R^b$, $SO_2NHCOR^a$, $CO_2R^c$, or a substituted or unsubstituted tetrazolyl or 1,2,4-oxadiazol-5(4H)-one-3-yl group;
$R^5$ is H, F, Cl, Br, I, $CO_2R^g$, $CF_3$, CN, $NR^gR^h$, $OR^g$, or a substituted or unsubstituted alkyl group;
$R^6$ is H, halo, $CO_2R^g$, $CF_3$, CN, $NR^gR^h$, $OR^g$, or a substituted or unsubstituted alkyl group;
$R^{10}$ at each occurrence is independently halo, or a substituted or unsubstituted alkyl, alkoxy, cycloalkyl, or fluorinated cycloalkyl group;
$R^a$ at each occurrence is independently H, or a substituted or unsubstituted alkyl, haloalkyl, cycloalkyl, aryl, alkylene-$R^d$, or $SO_2$-alkyl group;
$R^b$ at each occurrence is H or a substituted or unsubstituted alkyl, or haloalkyl group;
$R^c$ is H or a substituted or unsubstituted alkyl, alkenyl, alkynyl, or cycloalkyl group;
$R^d$ is $CO_2H$, OH, or $SO_3H$;
$R^g$ and $R^h$ at each occurrence are independently H or a substituted or unsubstituted $C_1$-$C_6$ alkyl group;

n is 0, 1, 2, 3, or 4;
r is 1, 2, or 3;
q is 0, 1, 2, or 3,
provided that:

when q is 0 or 1, then at least one of $R^5$ and $R^6$ is not H or n is at least 1; and when r+q is at least 3, then $R^5$ is not F.

In a related aspect, a composition is provided that includes the compound of any one of the compounds of formula I disclosed herein and a pharmaceutically acceptable carrier.

In another aspect, a pharmaceutical composition is provided, the pharmaceutical composition including an effective amount of the compound of any one of the above embodiments for treating an FXR-mediated disorder or condition, and optionally one or more of a pharmaceutically acceptable carrier and/or excipient(s).

In another aspect, a method is provided that includes administering an effective amount of a compound of any aspect or embodiment described herein, or administering a pharmaceutical composition including an effective amount of such a compound, to a subject suffering from an FXR-mediated disorder or condition.

In another aspect, a method is provided that includes modulating FXR in vitro or in a subject by contacting FXR with an effective amount of any one of the compounds of formula I or aspects or embodiments thereof as described herein.

DETAILED DESCRIPTION

In various aspects, the present technology provides compounds and methods for modulating FXR and the treatment of FXR-mediated disorders and conditions. The compounds provided herein can be formulated into pharmaceutical compositions and medicaments that are useful in the disclosed methods. Also provided is the use of the compounds in preparing pharmaceutical formulations and medicaments.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); $CF_3$; hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; amines; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, oxadiazolonyl (including 1,2,4-oxazol-5(4H)-one-3-yl), isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolykazaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tertbutoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to —COOR$^{70}$ and —C(O)O-G groups. R$^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methyl-amino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while "sulfides" include —SR$^{80}$ groups, "sulfoxides" include —S(O)R$^{81}$ groups, "sulfones" include —SO$_2$R$^{82}$ groups, and "sulfonyls" include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C—(O) NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O$^-$. A "hydroxyalkyl" group is a hydroxyl-substituted alkyl group, such as HO—CH$_2$—.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "isocyano" refers to —NC.

The term "isothiocyano" refers to —NCS.

The phrase "selectively modulates" as used herein will be understood by persons of ordinary skill in the art and will vary to some extent depending upon the context in which the phrase is used. If there are uses of the phrase which are not clear to persons of ordinary skill in the art, given the context in which the phrase is used, the phrase at minimum refers to the compounds acting through a specific mechanism of action, resulting in fewer off-target effects because the compounds target a particular receptor over other receptors, such as an FXR over a GR receptor, LXR, PPARγ, TGR5 or PXR. This phrase may further be modified as discussed herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. Na$^+$, Li$^+$, K$^+$, Ca$^{2+}$, Mg$^{2+}$, zn$^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, guanidines may exhibit the following isomeric forms in protic organic solution, also referred to as tautomers of each other:

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

In one aspect, the present technology provides heterocyclic derivatives that modulate FXR and intermediates for making such compounds. Thus, there are provided compounds according to formula I:

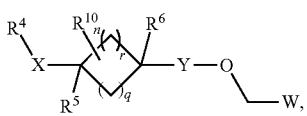

(I)

stereoisomers, and/or salts thereof wherein
W is

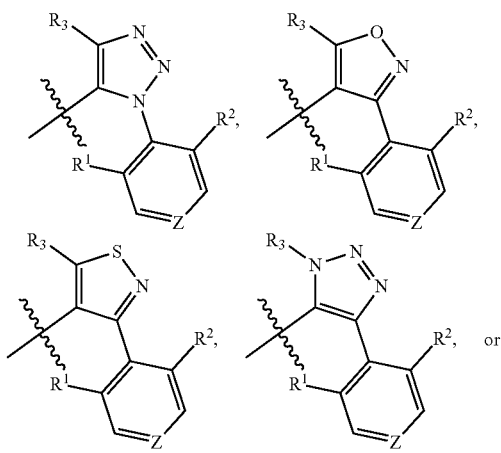

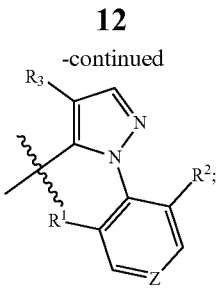

X is a substituted or unsubstituted aryl or heteroaryl group;
Y is a substituted or unsubstituted phenyl or pyridyl group;
Z is CH or N;
$R^1$ and $R^2$ are independently H, OH, halo, CN, carboxyl, $NR^aR^b$, or a substituted or unsubstituted alkyl, alkoxy, or hydroxyalkyl group;
$R^3$ is a substituted or unsubstituted alkyl or cycloalkyl group;
$R^4$ is CN, $SO_3H$, $CONR^aR^b$, $SO_2NR^aR^b$, $NHSO_2R^b$, $SO_2NHCOR^a$, $CO_2R^c$, or a substituted or unsubstituted tetrazolyl or 1,2,4-oxadiazol-5(4H)-one-3-yl group;
$R^5$ is H, F, Cl, Br, I, $CO_2R^g$, $CF_3$, CN, $NR^gR^h$, $OR^g$, or a substituted or unsubstituted alkyl group;
$R^6$ is H, halo, $CO_2R^g$, $CF_3$, CN, $NR^gR^h$, $OR^g$, or a substituted or unsubstituted alkyl group;
$R^{10}$ at each occurrence is independently halo, or a substituted or unsubstituted alkyl, alkoxy, cycloalkyl, or fluorinated cycloalkyl group;
$R^a$ at each occurrence is independently H, or a substituted or unsubstituted alkyl, haloalkyl, cycloalkyl, aryl, alkylene-$R^d$, or $SO_2$-alkyl group;
$R^b$ at each occurrence is H or a substituted or unsubstituted alkyl, or haloalkyl group;
$R^c$ is H or a substituted or unsubstituted alkyl, alkenyl, alkynyl, or cycloalkyl group;
$R^d$ is $CO_2H$, OH, or $SO_3H$;
$R^g$ and $R^h$ at each occurrence are independently H or a substituted or unsubstituted $C_1$-$C_6$ alkyl group;
n is 0, 1, 2, 3, or 4;
r is 1, 2, or 3;
q is 0, 1, 2, or 3,
provided that:
when q is 0 or 1, then at least one of $R^5$ and $R^6$ is not H or n is at least 1; and
when r+q is at least 3, then $R^5$ is not F. In some embodiments when r+q is at least 3,
then $R^5$ and/or $R^6$ is/are not F and not OH.

In some embodiments of compounds disclosed herein, q is 0, and in other embodiments, r is 1. In certain embodiments, q is 0 and r is 1, such that the compound of formula I includes a cyclopropyl group. Compounds containing cyclopropyl groups include racemic compounds or those having a cis or trans relationship between X and Y. In some embodiments wherein q is 0 and r is 1, X and Y are trans to each other. In certain embodiments the compounds of formula I have the structure II, IIA, IIB or a mixture of two or more thereof:

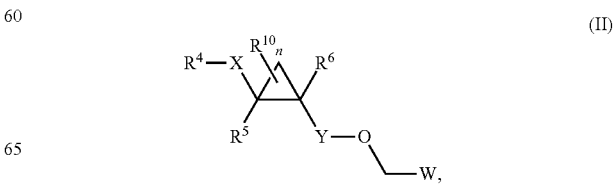

(II)

-continued

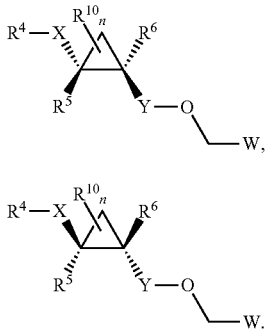

In some embodiments, W is

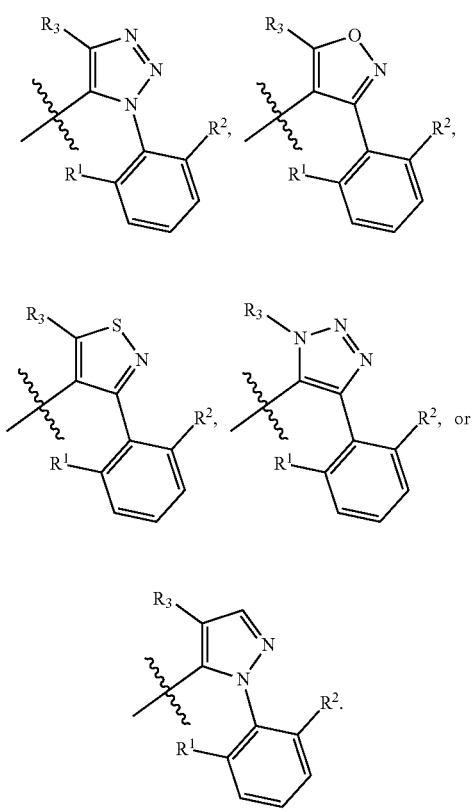

In some embodiments, W is

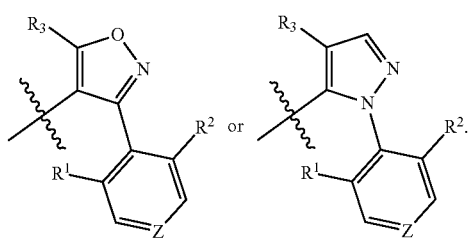

In certain embodiments disclosed herein, Z may be CH. In certain others, Z may be N. For example, in some embodiments, W is

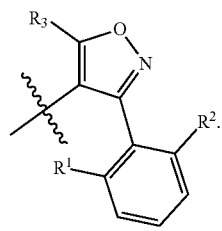

In certain embodiments of compounds disclosed herein $R^1$ and $R^2$ are independently H, halo, CN, $CO_2H$, $N^eR^f$, or a substituted or unsubstituted $C_1$-$C_6$ alkyl, $C_1$-$C_6$ alkoxy, or $C_1$-$C_6$ hydroxyalkyl group; and wherein $R^e$ and $R^f$ at each occurrence are independently H or a substituted or unsubstituted $C_1$-$C_6$ alkyl group. In some embodiments, $R^1$ and $R^2$ are not both H. In some embodiments, one of $R^1$ and $R^2$ is H and the other is selected from halo, CN, $CO_2H$, $NR^eR^f$, or a substituted or unsubstituted $C_1$-$C_6$ alkyl, $C_1$-$C_6$ alkoxy, or $C_1$-$C_6$ hydroxyalkyl group. In some embodiments, one of $R^1$ and $R^2$ is H and the other is selected from halo, a haloalkyl group, or a haloalkoxy group. For example, in some embodiments, $R^1$ is H and $R^2$ is selected from Cl, $OCHF_2$, and $OCF_3$. In some embodiments, $R^1$ and $R^2$ are independently halo, CN, $CO_2R^e$, $NR^eR^f$, or a substituted or unsubstituted $C_1$-$C_6$ alkyl, $C_1$-$C_6$ alkoxy, or $C_1$-$C_6$ hydroxyalkyl group; and wherein $R^e$ and $R^f$ at each occurrence are independently H or a substituted or unsubstituted $C_1$-$C_6$ alkyl group. In some embodiments, $R^1$ and $R^2$ are independently F, Cl, CN, $CO_2H$, $NR^eR^f$, or a substituted or unsubstituted $C_1$-$C_3$ alkyl, $C_1$-$C_3$ alkoxy, or $C_1$-$C_3$ hydroxyalkyl group; and wherein $R^e$ and $R^f$ are independently H or a substituted or unsubstituted $C_1$-$C_6$ alkyl group. In some embodiments, $R^1$ and $R^2$ are independently F, Cl, CN, $CO_2H$, $NH_2$, $CH_3$, $CH_2NH_2$, or $OCH_3$. In some embodiments, $R^1$ and $R^2$ are both Cl, both $CF_3$, both $OCF_3$, or both $OCHF_2$. In some embodiments, $R^1$ and $R^2$ are both Cl.

In some embodiments, $R^3$ is a substituted or unsubstituted $C_1$-$C_6$ alkyl or $C_3$-$C_6$ cycloalkyl group. In some embodiments, $R^3$ is a substituted or unsubstituted $C_1$-$C_3$ alkyl group. In some embodiments, $R^3$ is $CH_3$, $CH_2CH_3$, $CH(CH_3)_2$, $CH_2CH(CH_3)_2$, $CH(CH_2CH_3)_2$, $CH(CH_2CH_3)(CH_3)$, $C(CH_3)_3$, or cyclopropyl group. In some embodiments, $R^3$ is a cyclopropyl group. In some embodiments, $R^3$ is a F or $CF_3$ substituted cyclopropyl group. In some embodiments, $R^3$ is $CH(CH_3)_2$.

In some embodiments of compounds disclosed herein, $R^4$ may be $CO_2H$, $CONH_2$, $SO_2NH_2$, or a substituted or unsubstituted $CO_2$—$C_1$-$C_6$ alkyl, $CO_2$—$C_3$-$C_6$ cycloalkyl, CONH—$C_1$-$C_6$ alkyl, CONH—$C_3$-$C_6$ cycloalkyl, or NH—$SO_2$—$C_1$-$C_6$ alkyl group. In some embodiments, $R^4$ is $CO_2H$, $CONH_2$, or a substituted or unsubstituted $CO_2$—$C_1$-$C_6$ alkyl, or CONH—$C_1$-$C_6$ alkyl group. In certain embodiments the $C_1$-$C_6$ alkyl or $C_3$-$C_6$ cycloalkyl is substituted with $CO_2H$ or $SO_3H$. For example, in some embodiments, $R^4$ may be $CO_2H$, $SO_3H$, or $CO_2$—$C_1$-$C_6$ alkyl, $CO_2$—$C_3$-$C_6$ cycloalkyl, CONH—$C_1$-$C_6$ alkyl, CONH—$C_3$-$C_6$ cycloalkyl, wherein the $C_1$-$C_6$ alkyl or $C_3$-$C_6$ cycloalkyl group is substituted with $CO_2H$ or $SO_3H$. In some embodiments, $R^4$ may be $CO_2H$, $SO_3H$, CONH—$C_1$-$C_6$ alkyl-$CO_2H$ or CONH—$C_1$-$C_6$ alkyl-$SO_3H$. In certain embodiments R4 may be $CO_2H$ or an unsubstituted $CO_2$—$C_1$-$C_6$ alkyl group.

In some embodiments of the present compounds, $R^5$ is OH, F, $CO_2H$, $CF_3$, CN, $NH_2$, $CH_2NH_2$, $CH_2OH$, $C_1$-$C_3$ alkyl, or a O—($C_1$-$C_3$ alkyl) group; and $R^6$ is H. In some embodiments, $R^5$ is CN or $C_1$-$C_3$ alkyl (e.g., methyl) and $R^6$ is H. In other embodiments, $R^6$ is OH, F, $CO_2H$, $CF_3$, CN, $NH_2$, $CH_2NH_2$, $CH_2OH$, $C_1$-$C_3$ alkyl, or a O—($C_1$-$C_3$ alkyl) group; and $R^5$ is H. In some embodiments, $R^6$ is CN or $C_1$-$C_3$ alkyl (e.g., methyl) and $R^5$ is H.

In some embodiments of the present compounds, n is 0. In others n is 1 or 2. In some embodiments where $R^{10}$ is present, $R^{10}$ is halo. In others $R^{10}$ is F and/or Cl.

In some embodiments of compounds disclosed herein, Y is a phenyl or pyridyl group substituted with one or two substituents independently selected from $C_1$-$C_6$ alkyl, $C_3$-$C_6$ cycloalkyl, $C_1$-$C_6$ haloalkyl, halo, and $CF_3$. In some embodiments, Y is phenyl group substituted with one or two substituents independently selected from F, Cl, or $CF_3$ groups. In some embodiments, Y is a phenyl group substituted with one or two Cl. In some embodiments, Y is a phenyl group substituted with one Cl.

In some embodiments, the compound of formula I has the structure (III):

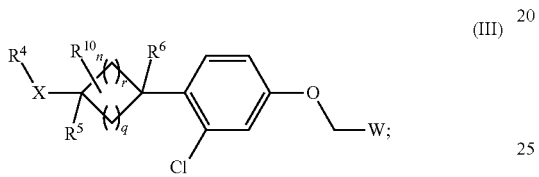

(III)

wherein: r is 1; q is 0; $R^5$ and $R^6$ are independently H, or an OH, F, $CO_2H$, $CF_3$, CN, $NH_2$, $CH_2NH_2$, $CH_2OH$, $C_1$-$C_3$ alkyl, or O—($C_1$-$C_3$ alkyl) group. In some such embodiments, $R^5$ is H, and $R^6$ is an OH, F, $CO_2H$, $CF_3$, CN, $NH_2$, $CH_2NH_2$, $CH_2OH$, $C_1$-$C_3$ alkyl, or O—($C_1$-$C_3$ alkyl) group. In certain embodiments, $R^5$ is H, and $R^6$ is $NH_2$, $CH_2NH_2$, $CH_2OH$, $CH_3$, $CF_3$, CN, $CO_2H$, F, or $OCH_3$. In some embodiments, $R^5$ is a OH, F, $CO_2H$, $CF_3$, CN, $NH_2$, $CH_2NH_2$, $CH_2OH$, $C_1$-$C_3$ alkyl, or O—($C_1$-$C_3$ alkyl) group, and $R^6$ is H. In some embodiments, $R^5$ is an $NH_2$, $CH_2NH_2$, $CH_2OH$, $CH_3$, $CF_3$, CN, $CO_2H$, F, or $OCH_3$, and $R^6$ is H.

In certain embodiments, wherein r is 1, q is 0 and n is 0, the compound of formula I has the structure IIIA:

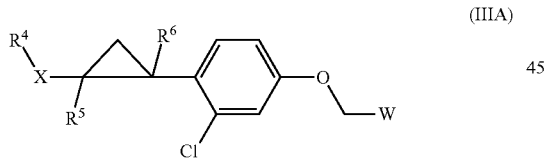

(IIIA)

wherein X, W, $R^4$, $R^5$, and $R^6$ may be defined as in any other embodiment described herein.

In some embodiments X is

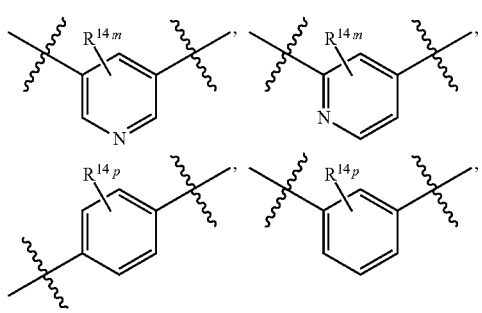

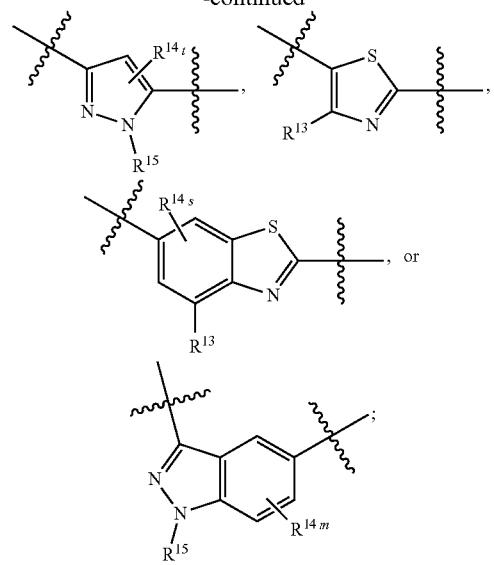

wherein:
$R^{13}$ is H, halo, or a substituted or unsubstituted $C_1$-$C_6$ alkyl, or O—($C_1$-$C_6$ alkyl) group;
$R^{14}$ at each occurrence is independently halo, $CF_3$, or a substituted or unsubstituted alkyl, or alkoxy group;
$R^{15}$ is H or a substituted or unsubstituted $C_1$-$C_6$ alkyl group;
m is 0, 1, 2, or 3;
p is 0, 1, 2, 3, or 4;
s is 0, 1, or 2; and
t is 0 or 1.

In some embodiments, $R^{13}$ is H, halo or an unsubstituted O—($C_1$-$C_3$ alkyl) group (e.g., F or $OCH_3$). In some embodiments, $R^{14}$ is a halo group. In some embodiments, $R^{14}$ is F or Cl. In some embodiments, m, p, s, or t is 0 and no $R^{14}$ is present. In some embodiments, $R^{15}$ is an unsubstituted $C_1$-$C_6$ alkyl group (e.g., isopropyl). In some embodiments, X is

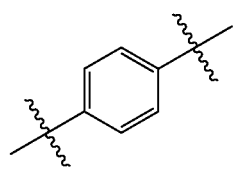

In other embodiments, X is

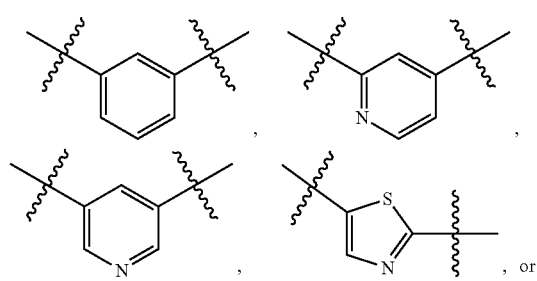

-continued

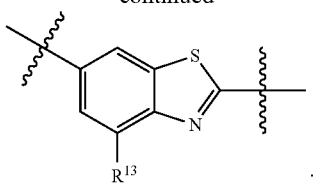

In some embodiments, X is

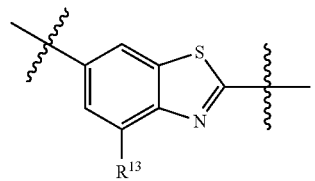

wherein $R^{13}$ is H, F or $OCH_3$.

In an aspect of the present technology, a composition is provided that includes any one of the aspects and embodiments of compounds disclosed herein (e.g., compounds of formulas I and IA) and a pharmaceutically acceptable carrier. In a related aspect, a pharmaceutical composition is provided which includes an effective amount of the compound of any one of the aspects and embodiments of compounds described herein for treating an FXR-mediated disorder or condition (optionally including a pharmaceutically acceptable carrier and/or excipient(s)). The FXR-mediated disorder or condition may be liver disease, hyperlipidemia, hypercholesteremia, obesity, metabolic syndrome, cardiovascular disease, gastrointestinal disease, atherosclerosis, or renal disease. For example, the disorder or condition may be a liver disease selected from the group consisting of primary biliary cirrhosis (PBC), cerebrotendinous xanthomatosis (CTX), primary sclerosing cholangitis (PSC), nonalcoholic fatty liver disease (NAFLD), nonalcoholic steatohepatitis (NASH), liver fibrosis, and liver cirrhosis.

In a further related aspect, a method is provided that includes administering an effective amount of a compound of any one of the aspects and embodiments described herein or administering a pharmaceutical composition comprising an effective amount of a compound of any one of the aspects and embodiments described herein to a subject suffering from an FXR-mediated disorder or condition. The FXR-mediated disorder or condition may be liver disease, hyperlipidemia, hypercholesteremia, obesity, metabolic syndrome, cardiovascular disease, gastrointestinal disease, atherosclerosis, or renal disease. In some embodiments, the disorder or condition is the disorder or condition may be a liver disease selected from the group consisting of primary biliary cirrhosis (PB C), cerebrotendinous xanthomatosis (CTX), primary sclerosing cholangitis (PSC), nonalcoholic fatty liver disease (NAFLD), nonalcoholic steatohepatitis (NASH), liver fibrosis, and liver cirrhosis.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of hyperlipidemia. Another example of an effective amount includes amounts or dosages that are capable of reducing symptoms associated with metabolic syndrome, such as, for example, obesity and/or metabolic syndrome. The effective amount of the compound may selectively modulate FXR. As used herein, a "subject" or "patient" is a mammal, such as a cat, dog, rodent or primate. Typically the subject is a human, and, preferably, a human suffering from or suspected of suffering from an FXR-mediated disorder or condition. The term "subject" and "patient" can be used interchangeably.

In still another aspect, the present technology provides methods of modulating FXR by contacting FXR with an effective amount of any compound as described herein, including but not limited to a compound of formula I or IA.

Thus, the instant present technology provides pharmaceutical compositions and medicaments comprising any of the compounds disclosed herein (e.g., compounds of formulas I and IA) and a pharmaceutically acceptable carrier or one or more excipients or fillers. The compositions may be used in the methods and treatments described herein. Such compositions and medicaments include a therapeutically effective amount of any compound as described herein, including but not limited to a compound of formulas I or IA. The pharmaceutical composition may be packaged in unit dosage form.

The pharmaceutical compositions and medicaments may be prepared by mixing one or more compounds of the present technology, stereoisomers thereof, and/or pharmaceutically acceptable salts thereof, with pharmaceutically acceptable carriers, excipients, binders, diluents or the like to prevent and treat disorders associated with the effects of increased plasma and/or hepatic lipid levels. The compounds and compositions described herein may be used to prepare formulations and medicaments that prevent or treat a variety of disorders associated with or mediated by FXR, including but not limited to liver disease, hyperlipidemia, hypercholesteremia, obesity, metabolic syndrome, cardiovascular disease, gastrointestinal disease, atherosclerosis and renal disease. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until for example, (for metabolic syndrome and/or obesity) the elevated plasma or elevated white blood cell count or hepatic cholesterol or triglycerides or progression of the disease state is reduced or stopped. For metabolic syndrome and/or obesity, the progression of the disease state can be assessed using in vivo imaging, as described, or by taking a tissue sample from a patient and observing the target of interest therein.

The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the treatment according to the present technology.

Effectiveness of the compositions and methods of the present technology may also be demonstrated by a decrease in the symptoms of hyperlipidemia, such as, for example, a decrease in triglycerides in the blood stream. Effectiveness of the compositions and methods of the present technology may also be demonstrated by a decrease in the signs and symptoms of chronic liver disease, hypercholesteremia, obesity, metabolic syndrome, cardiovascular disease, gastrointestinal disease, atherosclerosis, renal disease, colorectal cancer, and stroke.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

The compounds of the present technology can also be administered to a patient along with other conventional therapeutic agents that may be useful in the treatment of chronic liver disease, hyperlipidemia, hypercholesteremia, obesity, metabolic syndrome, cardiovascular disease, gastrointestinal disease, atherosclerosis, renal disease, colorectal cancer, and stroke. The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent in an amount that can potentially be effective for the treatment of chronic liver disease, hyperlipidemia, hypercholesteremia, obesity, metabolic syndrome, cardiovascular disease, gastrointestinal disease, atherosclerosis, renal disease, colorectal cancer, and stroke.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1\times10^{-4}$ g/kg to 1 g/kg, preferably, $1\times10^{-3}$ g/kg to 1.0 g/kg. Dosage of a compound of the present technology can also vary from 0.01 mg/kg to 100 mg/kg or, preferably, from 0.1 mg/kg to 10 mg/kg.

A compound of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

In another aspect, the present technology provides methods of identifying a target of interest including contacting the target of interest with a detectable or imaging effective quantity of a labeled compound of the present technology. A detectable or imaging effective quantity is a quantity of a labeled compound of the present technology necessary to be detected by the detection method chosen. For example, a detectable quantity can be an administered amount sufficient to enable detection of binding of the labeled compound to a target of interest including, but not limited to, a KOR. Suitable labels are known by those skilled in the art and can include, for example, radioisotopes, radionuclides, isotopes, fluorescent groups, biotin (in conjunction with streptavidin complexation), and chemoluminescent groups. Upon binding of the labeled compound to the target of interest, the target may be isolated, purified and further characterized such as by determining the amino acid sequence.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

List of Abbreviations

ACN acetonitrile
t-Bu tert-butyl
DCM dichloromethane
DIAD diisopropyl azodicarboxylate
DMF dimethylformamide
DMA dimethylacetamide
DMAP 4-dimethylaminopyridine
DMP tert-2,2-dimethoxypropane
DMSO dimethyl sulfoxide
Et ethyl
HATU (1-[bis(dimethylamino)methylene]-1H-1,2,3-triazolo[4,5-b] pyridinium 3-oxid hexafluorophosphate)
LAH lithium aluminum hydride
Me methyl
MeCN acetonitrile
NCS N-chlorosuccinimide
PCC pyridinium chlorochromate
PE petroleum ether
Ph phenyl
TEA triethylamine
TFA trifluoroacetic acid
TFAA trifluoroacetic anhydride
THF tetrahydrofuran
TLC thin layer chromatography
TMS trimethylsilyl
TsOH p-toluenesulfonic acid

Common Intermediates Synthetic Schemes

Scheme 1 (Compound INT-001, 002 and 003)

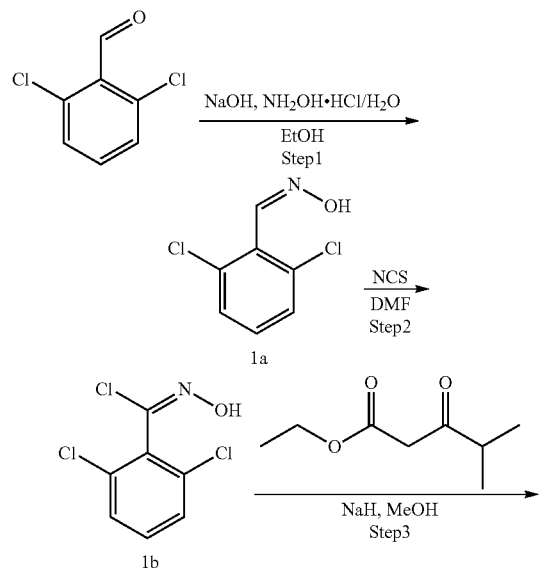

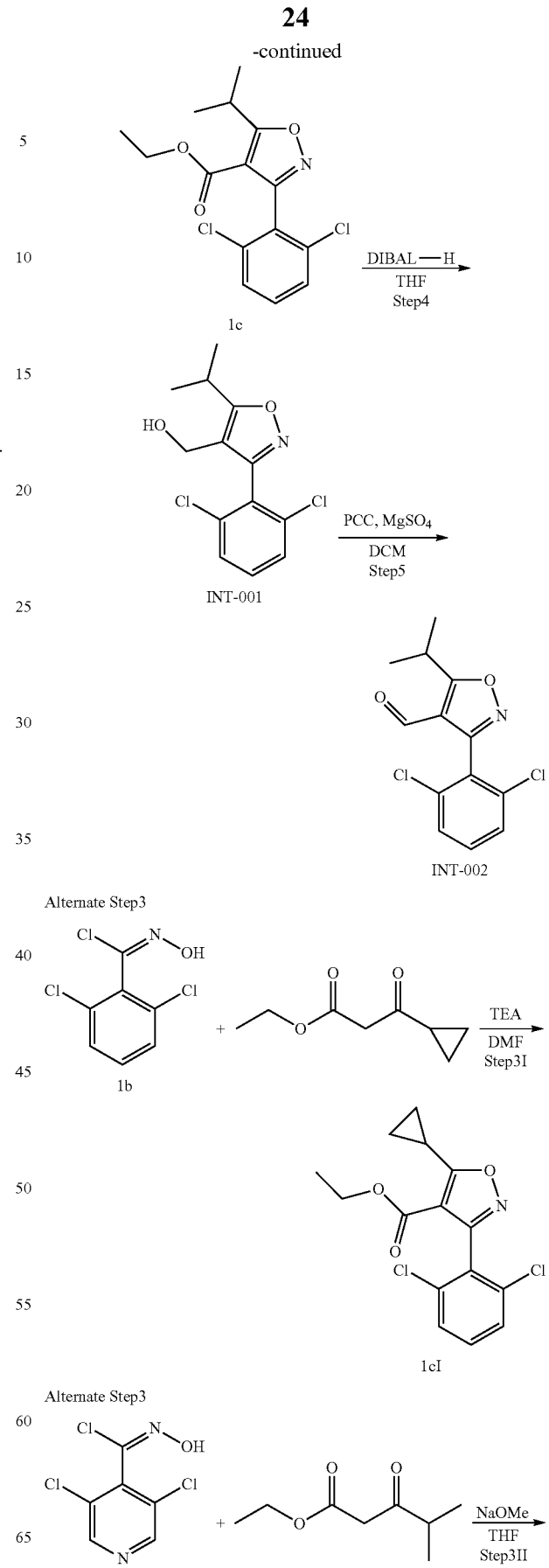

Alternate Step3

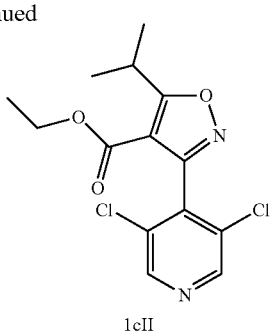

Alternate Step4

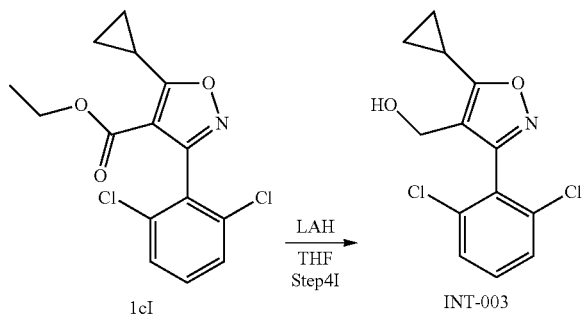

Experimental Details for Compound INT-001, 002 and 003 (Scheme 1)

(Z)—N-[(2,6-Dichlorophenyl) methylidene] hydroxylamine (Compound 1a)

To a solution of sodium hydroxide (207 ml, 2N) was added a solution of NH$_2$OH.HCl (39.4 g, 628 ml) in water (50 mL) dropwise at 0° C. The mixture was stirred for 0.5 h then a solution of 2,6-dichlorobenzaldehyde (100 g, 571 mmol) in ethanol (500 mL) was added dropwise at this temperature. The mixture was allowed warm to room temperature and stirred for another 2 h. The resulting mixture was concentrated under vacuum. The residue was suspended in a mixed solvent of water and ethanol (550 ml, 10:1). The solids were collected by filtration then washed with cooled ethanol and dried under vacuum. This resulted in 104.7 g (96%) of the title compound as a white solid. LC-MS (ESI, m/z): [M+H]$^+$=190.1.

(E)-2,6-Dichloro-N-hydroxybenzene-1-carbonimidoyl Chloride (Compound 1b)

To a solution of Compound 1a (60 g, 316 mmol) in DMF (500 mL) was added NCS (42.1 g, 315 mmol) batchwise at room temperature. The resulting mixture was stirred for 2 h at 45° C. The mixture was diluted with water and extracted with ethyl acetate several times. The organic layers were combined and washed with water and brine, then dried over anhydrous sodium sulfate, and concentrated under vacuum. This resulted in 67 g (95%) of the title compound as a white solid. The crude product was used directly without further purification.

Ethyl 3-(2,6-dichlorophenyl)-5-(propan-2-yl)-1,2-oxazole-4-carboxylate (Compound 1c)

Sodium hydride (11.1 g, 463 mmol) was added into methanol (1000 mL) batchwise at 0° C. The mixture was stirred for 0.5 h at this temperature then a solution of ethyl 4-methyl-3-oxopentanoate (48 g, 303 mmol) in methanol (30 mL) was added dropwise into above mixture at this temperature within 0.5 h. The mixture was stirred for another 0.5 h then a solution of Compound 1b (50 g, 223 mmol) in methanol (20 mL) was added dropwise. The resulting solution was stirred for another 16 h at room temperature. The reaction was quenched by adding saturated sodium bicarbonate aqueous solution. The solvent was removed under vacuum. The residue was extracted with ethyl acetate. The organic layers were combined and washed with water and brine, then dried over anhydrous sodium sulfate, and concentrated under vacuum. The residue was applied onto a silica gel column with dichloromethane/petroleum ether (1:99). This resulted in 50 g (68%) of the title compound as a white solid. LC-MS (ESI, m/z): [M+H]$^+$= 328.2.

[3-(2,6-Dichlorophenyl)-5-(propan-2-yl)-1,2-oxazol-4-yl] methanol (Compound INT-001)

To a solution of Compound 1c (50 g, 152 mmol) in THF (500 mL) was added a solution of DIBAL-H in hexane (305 mL, 610 mmol, 2M) dropwise at 0° C. The mixture was allowed warm to room temperature and stirred for another 3 h at room temperature. The reaction was quenched by adding water. The pH value of the mixture was adjusted to 2-3 with hydrogen chloride (3 N). The solvent was removed under vacuum. The residue was extracted with ethyl acetate several times. The organic layers were combined and washed with water and brine, then dried over anhydrous sodium sulfate, and concentrated under vacuum. The crude product was recrystallized from hexane and ethyl acetate. This resulted in 40 g (92%) of the title compound as a white solid. LC-MS (ESI, m/z): [M+H]$^+$=286.3.

3-(2,6-Dichlorophenyl)-5-(propan-2-yl)-1,2-oxazole-4-carbaldehyde (Compound INT-002)

To a suspension of PCC (13.2 g, 61.2 mmol) and magnesium sulfate (20.9 g, 174 mmol) in dichloromethane (100 mL) was added a solution of Compound INT-001 (8 g, 27.9 mmol) in dichloromethane (10 mL) dropwise at 0° C. The resulting mixture was allowed warm to room temperature and stirred for another 2 h. The solids were filtered out. The resulting mixture was concentrated under vacuum. The residue was applied onto a silica gel column with ethyl acetate/petroleum ether (2:8). This resulted in 7 g (88%) of the title compound as a white solid. LC-MS (ESI, m/z): [M+H]$^+$=284.2.

Ethyl 5-cyclopropyl-3-(2,6-dichlorophenyl)-1,2-oxazole-4-carboxylate (Compound 1d)

To a solution of ethyl 3-cyclopropyl-3-oxopropanoate (90.5 g, 579 mmol) and triethylamine (38 g, 376 mmol) in DMF (100 ml) was added a solution of Compound 1b (65 g, 290 mmol) in DMF (150 mL) dropwise at room temperature. The reaction was then quenched by the addition of 200 mL of water after stirring for 16 h at room temperature. The solids were collected by filtration. This resulted in 81 g (86%) of as a yellow solid. LC-MS (ESI, m/z): [M+H]$^+$= 326.2.

Ethyl-3-(3,5-dichloropyridin-4-yl)-5-(propan-2-yl)-1,2-oxazole-4-carboxylate (Compound 1cII)

To a solution of NaOMe (127 mg, 2.35 mmol) in tetrahydrofuran (15 mL) was added ethyl 4-methyl-3-oxopentanoate (324 mg, 2.05 mmol) dropwise at 0° C. The mixture was stirred for 0.5 h then a solution of (E)-3,5-dichloro-N-hydroxypyridine-4-carbonimidoyl chloride (160 mg, 0.71 mmol) in tetrahydrofuran (5 mL) was added. The resulting solution was stirred for 16 h at room temperature. The reaction was quenched by adding saturated $NH_4Cl$ solution. The resulting mixture was extracted with 3×50 mL of ethyl acetate. The organic layers were combined and washed with water and brine, then dried over anhydrous sodium sulfate, and concentrated under vacuum. The residue was applied onto a silica gel column with ethyl acetate/petroleum ether (1:4). This resulted in 466 mg (71%) of the title compound as a light yellow oil. LC-MS (ESI, m/z): $[M+H]^+$=328.9.

[5-Cyclopropyl-3-(2,6-dichlorophenyl)-1,2-oxazol-4-yl] methanol (Compound INT-003)

To a solution of Compound 1cI (50 g, 153 mmol) in THF (200 mL) was added lithium aluminum hydride (5.5 g, 162 mmol) batchwise at 0° C. The mixture was allowed warm to room temperature and stirred for 2 h at room temperature. The reaction was quenched by the addition of water. The solids were filtered out. The resulting mixture was concentrated under vacuum. The residue was recrystallized from hexane and ethyl acetate. This resulted in 34 g (78%) of the title compound as a white solid. LC-MS (ESI, m/z): $[M+H]^+$= 284.0.

Following the procedure described above for Scheme 1 and substituting the appropriate reagents, starting materials and purification methods known to those skilled in the art, the following common intermediates were prepared.

TABLE 1

| Compound | Structure | Note | LC-MS $(M + H)^+$ |
|---|---|---|---|
| INT-004 | 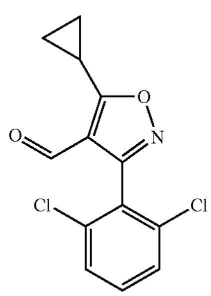 [SMILES: O=Cc1c(-c2c(Cl)cccc2Cl)noc1C1CC1] | Alternate Step3I and Step4 applied | 282.1 |
| INT-005 | 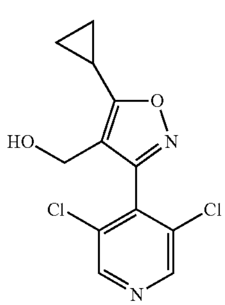 [SMILES: OCc1c(-c2c(Cl)cncc2Cl)noc1C1CC1] | Alternate Step3I applied | 284.9 |

TABLE 1-continued

| Compound | Structure | Note | LC-MS (M + H)+ |
|---|---|---|---|
| INT-006 | 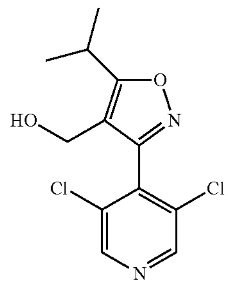 [SMILES: CC(C)c1onc(-c2c(Cl)cncc2Cl)c1CO] | Alternate Step3II applied | 287.4 |
| INT-007 | 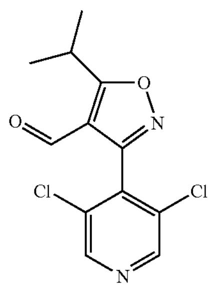 [SMILES: CC(C)c1onc(-c2c(Cl)cncc2Cl)c1C=O] | Alternate Step3II applied | 285.4 |
| INT-008 | 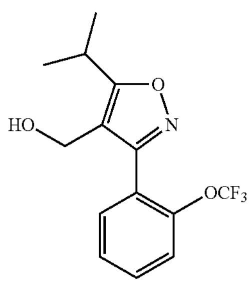 [SMILES: CC(C)c1onc(-c2ccccc2OC(F)(F)F)c1CO] | Alternate Step3II applied | 302.1 |
| INT-009 | 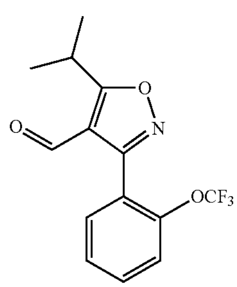 [SMILES: CC(C)c1onc(-c2ccccc2OC(F)(F)F)c1C=O] | Alternate Step3II applied | 300.1 |
| INT-010 | 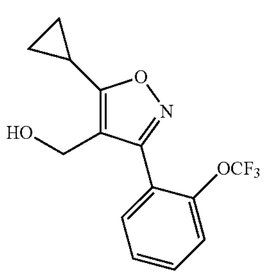 [SMILES: OCc1c(-c2ccccc2OC(F)(F)F)noc1C1CC1] | Alternate Step3I applied | 300.1 |

TABLE 1-continued

| Compound | Structure | Note | LC-MS (M + H)+ |
|---|---|---|---|
| INT-011 | 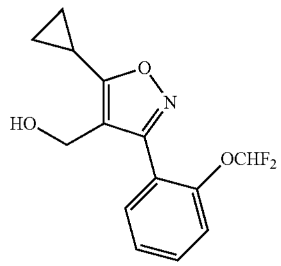 [SMILES: OCc1c(-c2ccccc2OC(F)F)noc1C1CC1] | Alternate Step3I applied | 282.0 |

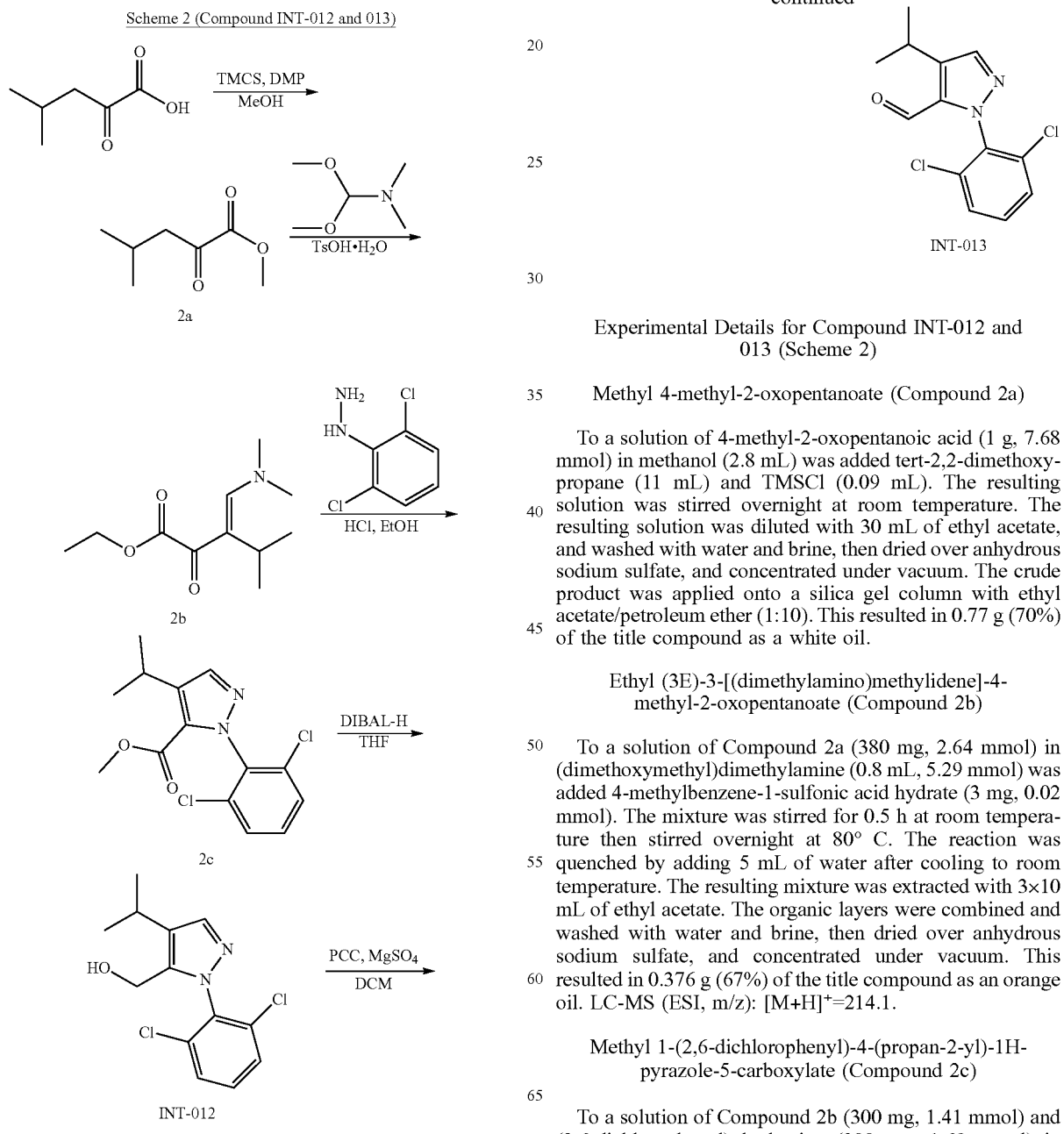

Experimental Details for Compound INT-012 and 013 (Scheme 2)

Methyl 4-methyl-2-oxopentanoate (Compound 2a)

To a solution of 4-methyl-2-oxopentanoic acid (1 g, 7.68 mmol) in methanol (2.8 mL) was added tert-2,2-dimethoxypropane (11 mL) and TMSCl (0.09 mL). The resulting solution was stirred overnight at room temperature. The resulting solution was diluted with 30 mL of ethyl acetate, and washed with water and brine, then dried over anhydrous sodium sulfate, and concentrated under vacuum. The crude product was applied onto a silica gel column with ethyl acetate/petroleum ether (1:10). This resulted in 0.77 g (70%) of the title compound as a white oil.

Ethyl (3E)-3-[(dimethylamino)methylidene]-4-methyl-2-oxopentanoate (Compound 2b)

To a solution of Compound 2a (380 mg, 2.64 mmol) in (dimethoxymethyl)dimethylamine (0.8 mL, 5.29 mmol) was added 4-methylbenzene-1-sulfonic acid hydrate (3 mg, 0.02 mmol). The mixture was stirred for 0.5 h at room temperature then stirred overnight at 80° C. The reaction was quenched by adding 5 mL of water after cooling to room temperature. The resulting mixture was extracted with 3×10 mL of ethyl acetate. The organic layers were combined and washed with water and brine, then dried over anhydrous sodium sulfate, and concentrated under vacuum. This resulted in 0.376 g (67%) of the title compound as an orange oil. LC-MS (ESI, m/z): [M+H]+=214.1.

Methyl 1-(2,6-dichlorophenyl)-4-(propan-2-yl)-1H-pyrazole-5-carboxylate (Compound 2c)

To a solution of Compound 2b (300 mg, 1.41 mmol) and (2,6-dichlorophenyl) hydrazine (300 mg, 1.69 mmol) in ethanol (6 mL) was added hydrogen chloride (0.05 mL, 12N). The mixture was stirred for 0.5 h at room temperature then stirred overnight at 80° C. The reaction was quenched by adding 6 mL of water. The resulting solution was extracted with 3×20 mL of ethyl acetate. The organic layers were combined and washed with water and brine, then dried over anhydrous sodium sulfate, and concentrated under vacuum. The residue was applied onto a silica gel column with ethyl acetate/petroleum ether (1:10). This resulted in 200 mg (45%) of the title compound as yellow oil. LC-MS (ESI, m/z): [M+H]$^+$=313.0.

[1-(2,6-Dichlorophenyl)-4-(propan-2-yl)-1H-pyrazol-5-yl] methanol (Compound INT-012)

To a solution of Compound 2c (200 mg, 0.64 mmol) in THF (5 mL) was added DIBAL-H (3 mL, 3 mmol, 1M) in hexane at 0° C. under $N_2$ atmosphere. The mixture was stirred for 3 h at room temperature. The reaction was quenched by adding 5 mL of water. The resulting solution was extracted with 3×15 mL of ethyl acetate. The organic layers were combined and washed with water and brine, then dried over anhydrous sodium sulfate, and concentrated under vacuum. The residue was applied onto a silica gel column with ethyl acetate/petroleum ether (1:5). This resulted in 100 mg (55%) of the title compound as a white solid. LC-MS (ESI, m/z): [M+H]$^+$=285.0

1-(2,6-Dichlorophenyl)-4-(propan-2-yl)-1H-pyrazole-5-carbaldehyde (Compound INT-013)

To a suspension of PCC (175 mg, 0.82 mmol 1) and magnesium sulfate (253 mg, 2.07 mmol) in dichloromethane (3 mL) was added Compound INT-012 (100 mg, 0.35 mmol). The mixture was stirred for 2 h at room temperature. The solids were filtered out. The resulting mixture was concentrated under vacuum. The residue was applied onto a silica gel column with ethyl acetate/petroleum ether (1:8). This resulted in 98 mg (99%) of the title compound as a white solid. LC-MS (ESI, m/z): [M+H]$^+$=283.0.

Scheme 3 (Compound INT-016)

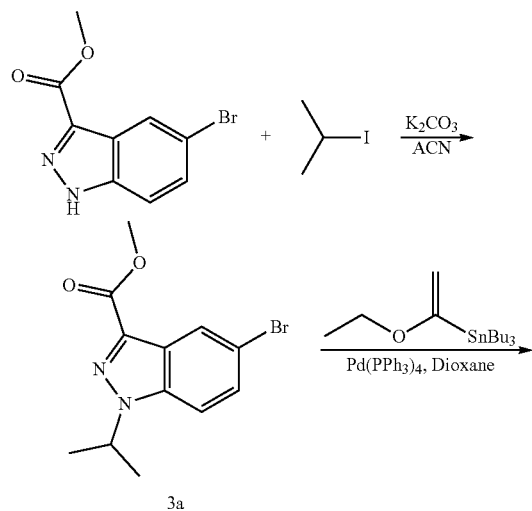

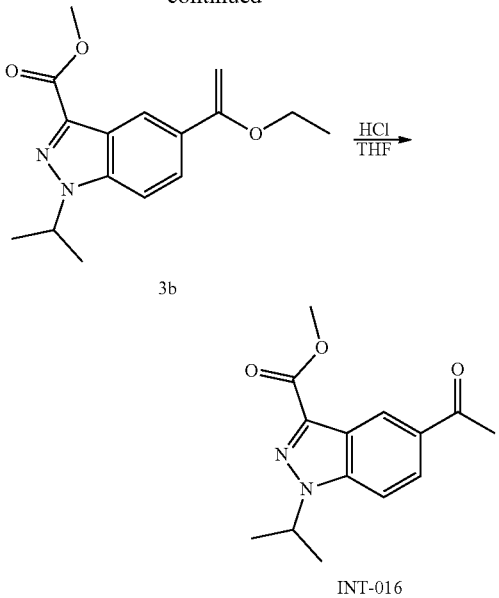

3b

INT-016

Experimental Details for Compound INT-016 (Scheme 3)

Methyl 5-bromo-1-(propan-2-yl)-1H-indazole-3-carboxylate (Compound 3a)

To a solution of methyl 5-bromo-1H-indazole-3-carboxylate (2 g, 7.84 mmol) in acetonitrile (100 mL) was added potassium carbonate (5.4 g, 39.1 mmol) and 2-iodopropane (6.6 g, 38.8 mmol). The resulting solution was stirred for 16 h at room temperature. The solids were filtered out. The resulting mixture was concentrated under vacuum. The residue was applied onto a silica gel column with ethyl acetate/petroleum ether (1:4). This resulted in 1.2 g (52%) of the title compound as a white solid. LC-MS (ESI, m/z): [M+H]$^+$=297.3.

Methyl 5-(1-ethoxyethenyl)-1-(propan-2-yl)-1H-indazole-3-carboxylate (Compound 3b)

To a solution of Compound 3a (1 g, 3.37 mmol) in dioxane (20 mL) was added tetrakis(triphenylphosphane)palladium (400 mg, 0.35 mmol) and tributyl(1-ethoxyethenyl)stannane (1.5 g, 4.15 mmol). The resulting solution was stirred for 16 h at 100° C. under $N_2$ atmosphere. The solvent was removed under vacuum. The residue was applied onto a silica gel column with ethyl acetate/petroleum ether (1:3). This resulted in 500 mg (52%) of the title compound as a white solid. LC-MS (ESI, m/z): [M+H]$^+$=289.2.

Methyl 5-acetyl-1-(propan-2-yl)-1H-indazole-3-carboxylate (Compound INT 016)

To a solution of Compound 3b (500 mg, 1.73 mmol) in tetrahydrofuran (10 mL) was added hydrogen chloride (5 mL, 3N). The resulting solution was stirred for 3 h at room temperature. The pH value of the solution was adjusted to 6-7 with saturated sodium bicarbonate solution. The resulting mixture was extracted with 3×30 mL of ethyl acetate. The organic layers were combined and washed with water and brine, then dried over anhydrous sodium sulfate, and concentrated under vacuum. The residue was applied onto a silica gel column with ethyl acetate/petroleum ether (18:82). This resulted in 400 mg (83%) of the title compound as a white solid. LC-MS (ESI, m/z): [M+H]$^+$=261.3.

Following the procedure described above for Scheme 3 and substituting the appropriate reagents, starting materials and purification methods known to those skilled in the art, the following common intermediates were prepared.

TABLE 2

| Compound | Structure | LC-MS (M + H)$^+$ |
|---|---|---|
| INT-014 | 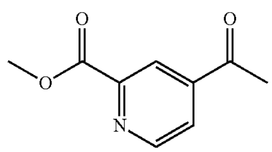 | 180.0 |
| INT-015 | 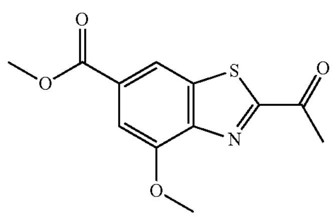 [SMILES: COC(=O)c1cc(OC)c2nc(C(C)=O)sc2c1] | 266.0 |
| INT-032 | 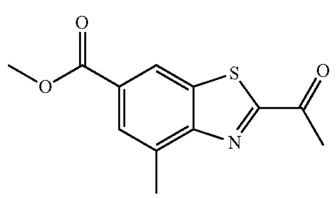 [SMILES: COC(=O)c1cc(C)c2nc(C(C)=O)sc2c1] | 250.0 |

Scheme 4 (Compound INT-017)

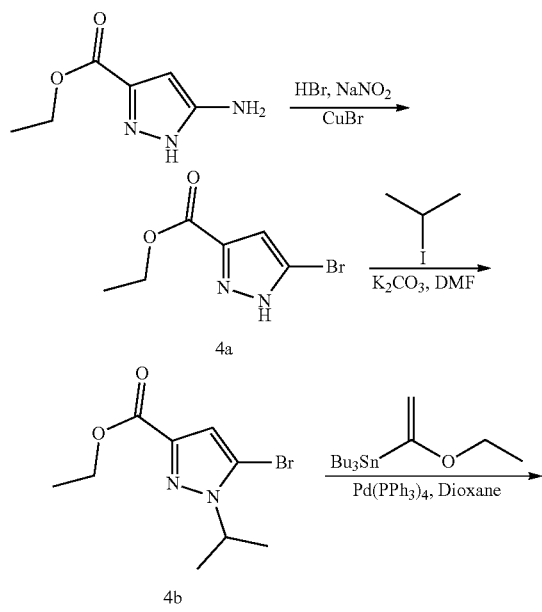

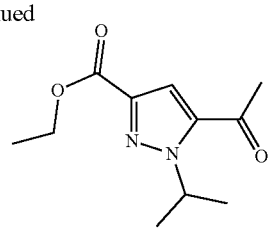

INT-017

Experimental Details for Compound INT-017
(Scheme 4)

Ethyl 5-bromo-1H-pyrazole-3-carboxylate
(Compound 4a)

To a solution of ethyl 5-amino-1H-pyrazole-3-carboxylate (500 mg, 3.54 mmol) in HBr (10 mL, 40%) was added a solution of NaNO$_2$ (269 mg, 3.90 mmol) in water (2 mL) at 0° C. The resulting solution was stirred for 10 min at 0° C. Then CuBr (1.5 g, 10.5 mmol) was added batchwise to the reaction. The mixture was stirred for 15 min at 0° C. The solids were filtered out. The resulting solution was extracted with 3×10 mL of dichloromethane. The organic layers were combined and concentrated under vacuum. The residue was applied onto a silica gel column with ethyl acetate/petroleum ether (1:10). This resulted in 260 mg (36%) of the title compound as a white solid. LC-MS (ESI, m/z): [M+H]$^+$= 219.1, 221.1

Ethyl 5-bromo-1-isopropyl-1H-pyrazole-3-carboxylate
(Compound 4b)

To a solution of Compound 4a (200 mg, 0.98 mmol) in DMF (2 mL) was added 2-iodopropane (204 mg, 1.20 mmol) and potassium carbonate (138 mg, 1.0 mmol). The resulting solution was stirred overnight at 90° C. The reaction was then quenched by addition of 5 mL of water. The resulting solution was extracted with 3×5 mL of ethyl acetate. The organic layers were combined and concentrated under vacuum. The residue was applied onto a silica gel column with ethyl acetate/petroleum ether (1:10). This resulted in 180 mg (75%) the title compound as a white solid. LC-MS (ESI, m/z): [M+H]$^+$=261.0, 263.0

Ethyl 5-acetyl-1-isopropyl-1H-pyrazole-3-carboxylate
(Compound INT-017)

To a solution of Compound 4b (1.2 g, 4.60 mmol) in dioxane (25 mL) was added tributyl(1-ethoxyvinyl)stannane (2.0 g, 5.54 mmol) and tetrakis(triphenylphosphane) palladium (530 mg, 0.46 mmol). The resulting solution was stirred overnight at 90° C. under N$_2$ atmosphere. The solids were filtered out. The resulting mixture was concentrated under vacuum. The residue was applied onto a silica gel column with ethyl acetate/petroleum ether (1:10). This resulted in 0.65 g (63%) of the title compound as a white solid. LC-MS (ESI, m/z): [M+H]$^+$=225.5.

Scheme 5 (Compound INT-019)

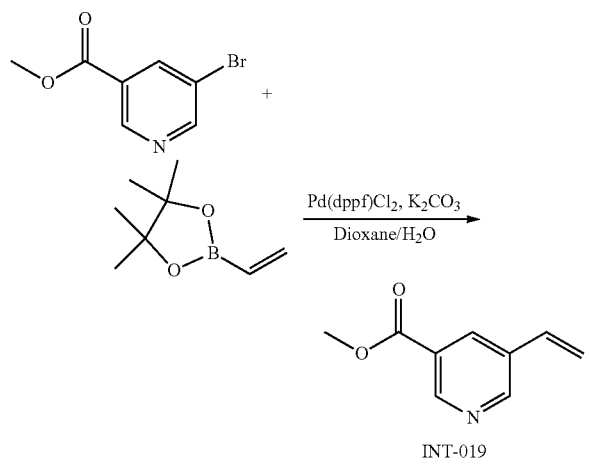

Experimental Details for Compound INT-019 (Scheme 5)

Methyl 5-ethenylpyridine-3-carboxylate (Compound INT-019)

To a solution of methyl 5-bromopyridine-3-carboxylate (500 mg, 2.31 mmol) and 2-ethenyl-4,4,5,5-tetramethyl-1,3,2-dioxaborolane (1.07 g, 6.95 mmol) in a mixed solvent of dioxane and water (9 mL, 7:2) was added potassium carbonate (476 mg, 3.44 mmol) and Pd(dppf)Cl$_2$ (84 mg, 0.11 mmol). The resulting solution was stirred for 2 h at 100° C. under N$_2$ atmosphere. The resulting solution was extracted with 3×15 mL of dichloromethane. The organic layers were combined and washed with water and brine, then dried over anhydrous sodium sulfate, and concentrated under vacuum. The residue was applied onto a silica gel column with ethyl acetate/petroleum ether (1:10). This resulted in 250 mg (66%) of the title compound as a yellow solid. LC-MS (ESI, m/z): [M+H]$^+$=164.2.

Following the procedure described above for Scheme 5 and substituting the appropriate reagents, starting materials and purification methods known to those skilled in the art, the following common intermediates were prepared.

TABLE 3

| Compound | Structure | LC-MS (M + H)$^+$ |
|---|---|---|
| INT-018 | | 163.1 |
| INT-020 | | 264.5 |
| INT-021 | 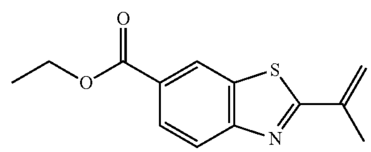 [SMILES: C=C(C)c1nc2ccc(C(=O)OCC)cc2s1] | 248.1 |
| INT-022 | 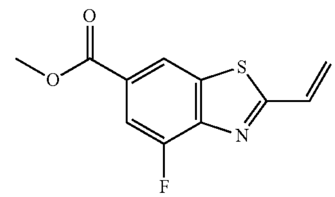 [SMILES: C=Cc1nc2c(F)cc(C(=O)OC)cc2s1] | 238.2 |
| INT-023 | 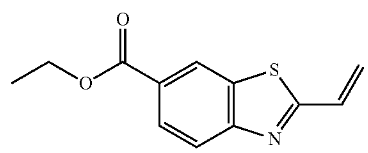 [SMILES: C=Cc1nc2ccc(C(=O)OCC)cc2s1] | 234.1 |
| INT-024 | 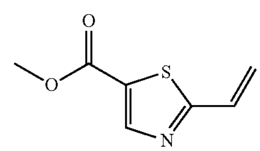 | 170.0 |
| INT-030 | 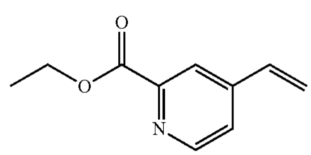 | 170.0 |
| INT-031 | 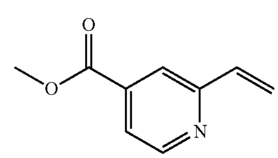 | 164.2 |
| INT-033 | 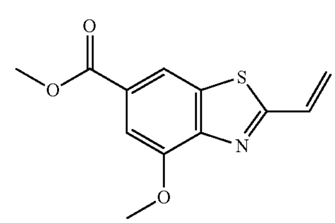 [SMILES: C=Cc1nc2c(OC)cc(C(=O)OC)cc2s1] | 250.0 |
| INT-034 | 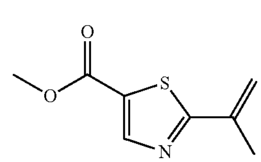 | 184.1 |

Scheme 6 (Compound INT-025)

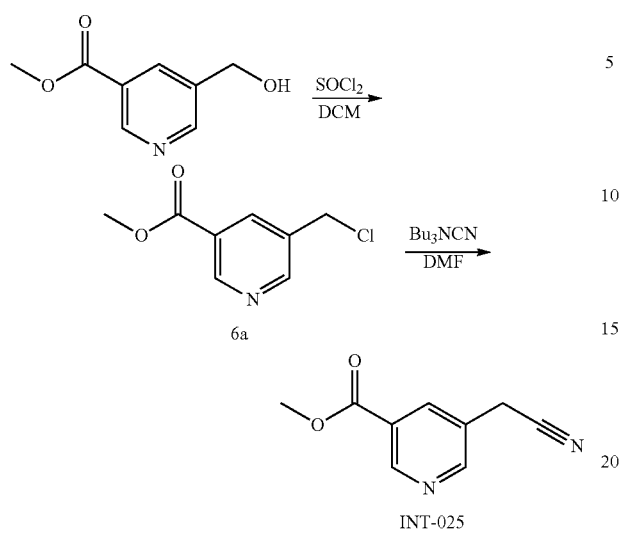

Experimental Details for Compound INT-025 (Scheme 6)

Methyl 5-(chloromethyl) pyridine-3-carboxylate (Compound 6a)

To a solution of methyl 5-(hydroxymethyl) pyridine-3-carboxylate (835 mg, 5.0 mmol) in DCM (30 mL) was added $SOCl_2$ (1.2 g, 10.1 mmol) at room temperature. The solution was stirred for 3 h at room temperature. The reaction was quenched by the addition of 50 ml of water/ice. The mixture was extracted with DCM several times. The organic layers were combined and dried over anhydrous magnesium sulfate. The residue was concentrated under vacuum. This resulted in 650 mg (crude) of the title compound as a solid. LC-MS (ESI, m/z): $[M+H+MeCN]^+=227.2$.

Methyl 5-(cyanomethyl) pyridine-3-carboxylate (Compound INT-025)

To a solution of Compound 6a (650 mg, 3.50 mmol) in DMF (25 mL) was added tributyl(cyano)azanium (900 mg, 4.26 mmol) at room temperature. The mixture was stirred for another 3 h at this temperature. The mixture was diluted with ethyl acetate and washed with water and brine, then dried over anhydrous sodium sulfate, and concentrated under vacuum. The residue was applied onto a silica gel column with ethyl acetate/hexane (1:2). This resulted in 0.35 g (57%) of the title compound as a solid. LC-MS (ESI, m/z): $[M+H]^+=177.1$.

Scheme 7 (Compound INT-026)

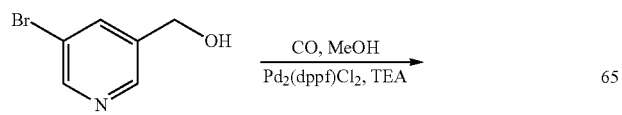

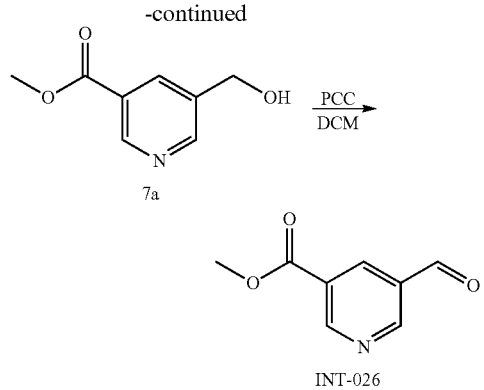

Experimental Details for Compound INT-026 (Scheme 7)

Methyl 5-(hydroxymethyl) pyridine-3-carboxylate (Compound 7a)

To a solution of (5-bromopyridin-3-yl) methanol (1.8 g, 9.57 mmol) in methanol (50 mL) was added $Pd(dppf)Cl_2$ (700 mg, 0.96 mmol) and triethylamine (6.5 mL). The reaction was stirred for 16 h at 80° C. under CO atmosphere (20 atm). The mixture was concentrated and applied onto a silica gel column with ethyl acetate/petroleum ether (1:1). This resulted in 1.2 g (75%) of the title compound as a solid. LC-MS (ESI, m/z): $[M+H]^+=168.2$.

Methyl 5-formylpyridine-3-carboxylate (Compound INT-026)

To a suspension of silica gel (1 g), PCC (450 mg) in dichloromethane (25 mL) was added Compound 7a (500 mg, 2.99 mmol). The reaction was stirred for 6 h at room temperature. The solids were filtered out. The resulting mixture was diluted with dichloromethane and washed with water and brine, dried over anhydrous magnesium sulfate, and concentrated under vacuum after filtration. The residue was applied onto a silica gel column with ethyl acetate/petroleum ether (1:1). This resulted in 300 mg (61%) of the title compound as a solid. LC-MS (ESI, m/z): $[M+H]^+=166.2$.

Scheme 8 (Compound INT-027)

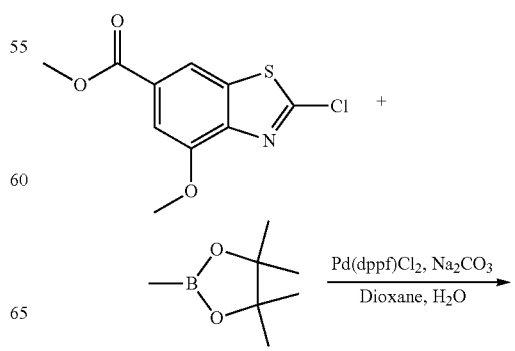

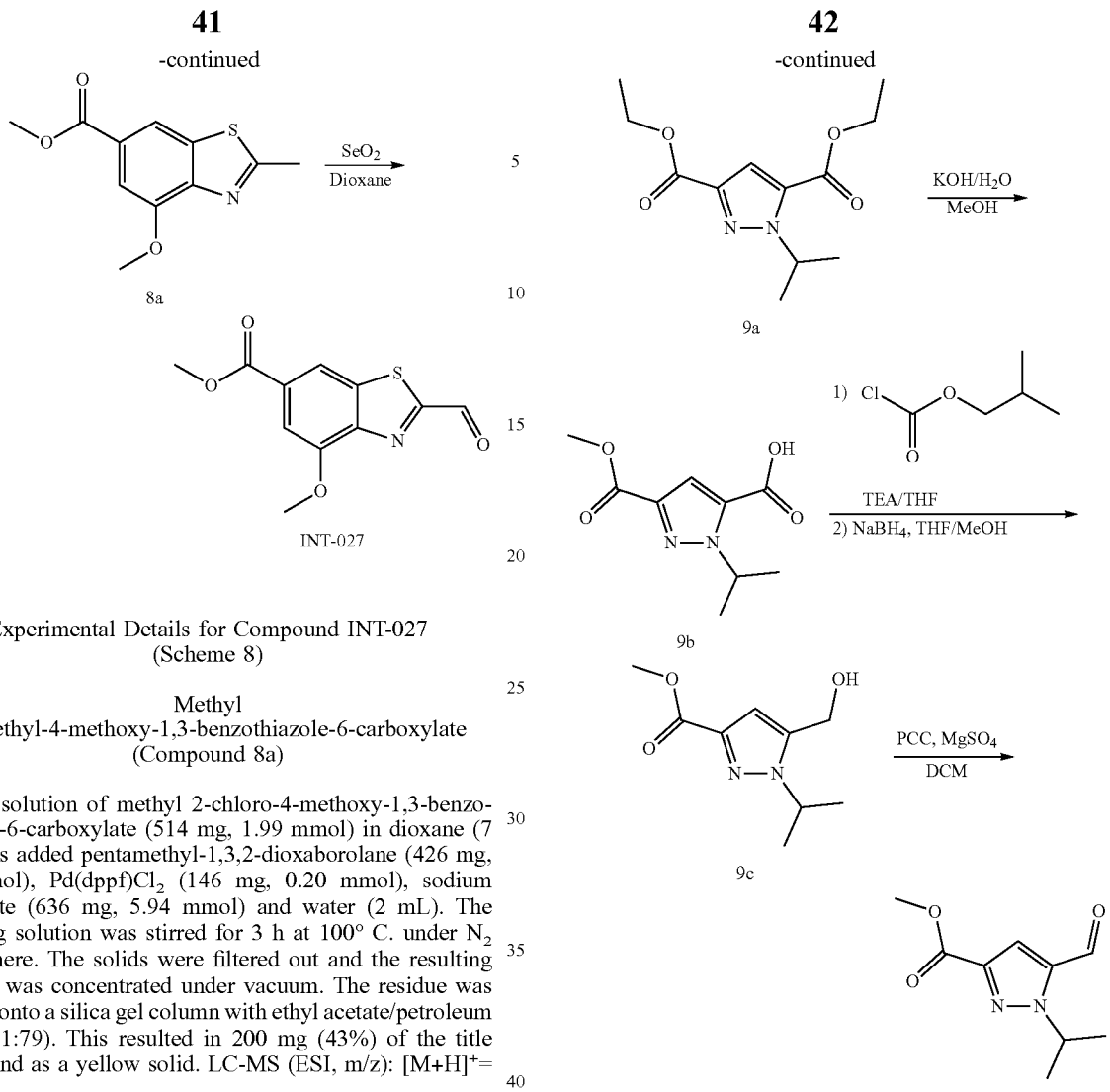

Experimental Details for Compound INT-027
(Scheme 8)

Methyl 2-methyl-4-methoxy-1,3-benzothiazole-6-carboxylate (Compound 8a)

To a solution of methyl 2-chloro-4-methoxy-1,3-benzothiazole-6-carboxylate (514 mg, 1.99 mmol) in dioxane (7 mL) was added pentamethyl-1,3,2-dioxaborolane (426 mg, 3.0 mmol), Pd(dppf)Cl$_2$ (146 mg, 0.20 mmol), sodium carbonate (636 mg, 5.94 mmol) and water (2 mL). The resulting solution was stirred for 3 h at 100° C. under N$_2$ atmosphere. The solids were filtered out and the resulting mixture was concentrated under vacuum. The residue was applied onto a silica gel column with ethyl acetate/petroleum ether (21:79). This resulted in 200 mg (43%) of the title compound as a yellow solid. LC-MS (ESI, m/z): [M+H]$^+$= 238.1.

Methyl 2-formyl-4-methoxy-1,3-benzothiazole-6-carboxylate (Compound INT 027)

To a solution of Compound 8a (200 mg, 0.84 mmol) in dioxane (3 mL) was added selenium dioxide (188 mg, 1.68 mmol). The mixture was stirred for 4 h at 100° C. The reaction was then quenched by the addition of water. The mixture was extracted with ethyl acetate several times and the organic layers were combined. The mixture was dried over anhydrous sodium sulfate and concentrated under vacuum. The residue was applied onto a silica gel column with ethyl acetate/petroleum ether (21:79). This resulted in 80 mg (38%) of the title compound as a yellow solid. LC-MS (ESI, m/z): [M+H]$^+$=252.2.

Scheme 9 (Compound INT-028)

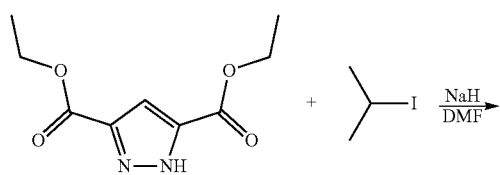

Experimental Details for Compound INT-028
(Scheme 9)

3,5-Diethyl 1-(propan-2-yl)-1H-pyrazole-3,5-dicarboxylate (Compound 9a)

To a solution of 3,5-diethyl 1H-pyrazole-3,5-dicarboxylate (3 g, 14.1 mmol) in DMF (25 mL) was added sodium hydride (620 mg, 15.5 mmol) batchwise at 0-5° C. The mixture was stirred for 0.5 h at this temperature then 2-iodopropane (2.6 g, 15.3 mmol) was added dropwise. The resulting mixture was stirred for another 6 h at room temperature. The reaction was quenched by the addition of saturated sodium bicarbonate solution. The resulting mixture was extracted with of ethyl acetate. The organic layers were combined and dried over anhydrous sodium sulfate. The mixture was concentrated under vacuum after filtration. The residue was applied onto a silica gel column with ethyl acetate/petroleum ether (16:84). This resulted in 2.8 g (78%) of the title compound as a white solid. LC-MS (ESI, m/z): [M+H]$^+$=255.3.

3-(Methoxycarbonyl)-1-(propan-2-yl)-1H-pyrazole-5-carboxylic Acid (Compound 9b)

To a solution of Compound 9a (2.8 g, 11.0 mmol) in methanol (20 mL) was added a solution of potassium hydroxide (600 mg, 10.7 mmol) in water (5 mL). The resulting solution was stirred for 16 h at room temperature. The pH value of the solution was adjusted to 3-4 with hydrogen chloride (2 N). The resulting mixture was extracted with ethyl acetate. The organic layers were combined and dried over anhydrous sodium sulfate. The mixture was concentrated under vacuum after filtration. This resulted in 2 g (80%) of the title compound as a white solid. LC-MS (ESI, m/z): [M+H]$^+$=213.2.

Methyl 5-(hydroxymethyl)-1-(propan-2-yl)-1H-pyrazole-3-carboxylate (Compound 9c)

To a solution of Compound 9b (850 mg, 4.01 mmol) and triethylamine (810 mg, 8.0 mmol) in tetrahydrofuran (10 mL) was added 2-methylpropyl chloroformate (600 mg, 4.39 mmol) dropwise at 0° C. The resulting mixture was allowed warm to room temperature and stirred for 2 h. The solids were filtered out. The resulted filtrate was added into a solution of NaBH$_4$ (152 mg, 4.02 mmol) in a mixed solvent of tetrahydrofuran (6 mL) and methanol (2 mL) at −50° C. The resulting solution was allowed warm to room temperature and stirred for another 2 h. The reaction was quenched by the addition of water. The resulting mixture was extracted with ethyl acetate several times. The organic layers were combined and washed with water and brine, then dried over anhydrous sodium sulfate, and concentrated under vacuum. The residue was applied onto a silica gel column with ethyl acetate/petroleum ether (3:7). This resulted in 530 mg (67%) of the title compound as a white solid. LC-MS (ESI, m/z): [M+H]$^+$=199.2.

Methyl 5-formyl-1-(propan-2-yl)-1H-pyrazole-3-carboxylate (Compound INT 028)

To a suspension of PCC (1.2 g, 5.57 mmol) and magnesium sulfate (1.8 g, 15.0 mmol) in dichloromethane (10 mL) was added a solution of Compound 9c (500 mg, 2.52 mmol) in dichloromethane (5 mL) dropwise at 0° C. The mixture was stirred for 3 h at room temperature. The solids were filtered out. The resulting mixture was concentrated under vacuum. The residue was applied onto a silica gel column with ethyl acetate/petroleum ether (1:4). This resulted in 400 mg (81%) of the title compound as a white solid. LC-MS (ESI, m/z): [M+H]$^+$=197.2.

Scheme 10 (Compound INT-029)

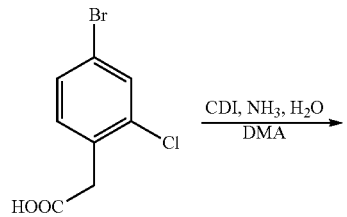

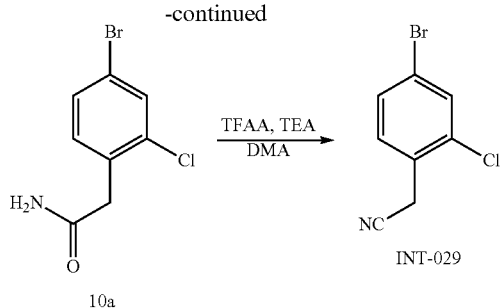

Experimental Details for Compound INT-029 (Scheme 10)

2-(4-Bromo-2-chlorophenyl) acetamide (Compound 10a)

To a solution of 2-(4-bromo-2-chlorophenyl) acetic acid (3 g, 12.0 mmol) in DMA (20 mL) was added CDI (3 g, 18.5 mmol) at room temperature. Then ammonia (3 mL, 25% w/w) was added in 45 min. The resulting solution was stirred for another 16 h at room temperature. The reaction was then quenched by the addition of 100 mL of water, extracted with 6×75 mL of ethyl acetate. The organic layers were combined, washed with water and brine and then dried over anhydrous sodium sulfate. The mixture was concentrated under vacuum after filtration. This resulted in 2.4 g (80%) of the title compound as a white solid. The product was used directly without further purification.

2-(4-Bromo-2-chlorophenyl) acetonitrile (Compound INT-029)

To a stirring solution of Compound 10a (1.8 g, 7.24 mmol) and triethylamine (2 mL, 14.5 mmol) in dichloromethane (15 mL) was added TFAA (2 mL, 14.5 mmol) dropwise at 0° C. in 3 min. The resulting solution was allowed to warm to room temperature and stirred for another 3 h. The reaction was then quenched by the addition of 100 mL of water/ice, extracted with 3×75 mL of ethyl acetate. The organic layers were combined and washed with water and brine, then dried over anhydrous magnesium sulfate and concentrated under vacuum. The residue was applied onto a silica gel column with ethyl acetate/hexane (1:8). This resulted in 0.93 g (56%) of the title compound as a white solid.

Final Compounds Synthetic Schemes

Scheme 11 (Compound IV-05)

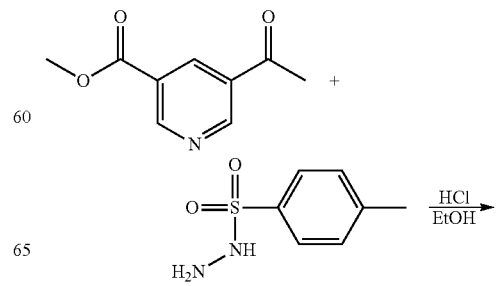

-continued

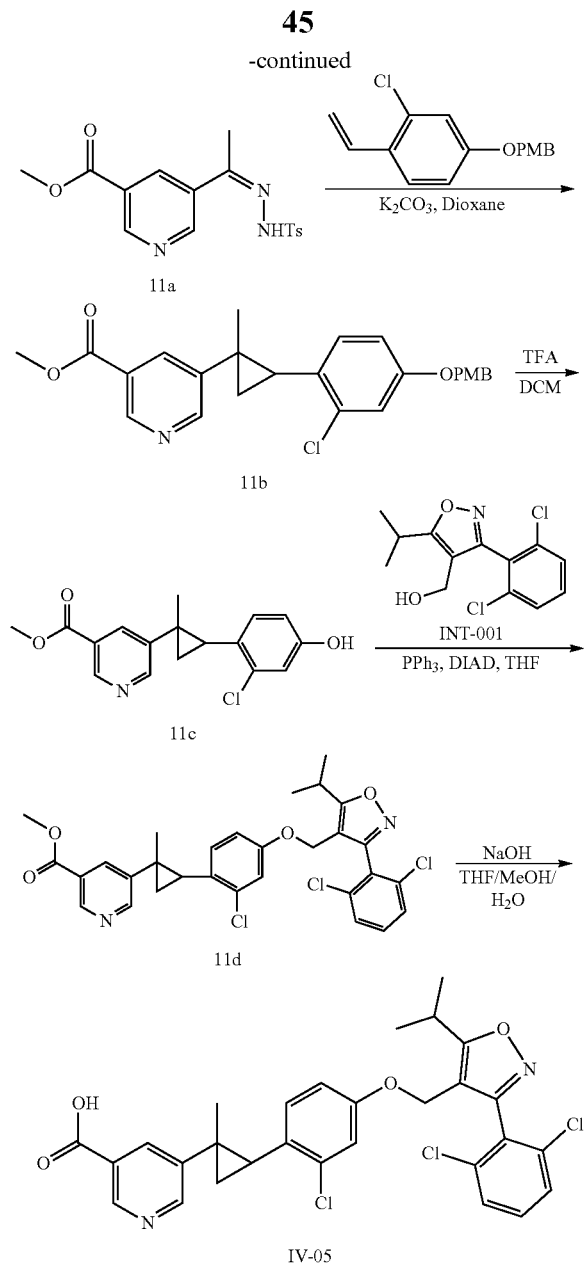

Experimental Details for Compound IV-05 (Scheme 11)

Methyl 5-[(1Z)-1-[[(4-methylbenzene)sulfonamido]imino]ethyl]pyridine-3-carboxylate (Compound 11a)

To a solution of methyl 5-acetylpyridine-3-carboxylate (180 mg, 1.0 mmol) and 4-methylbenzene-1-sulfonohydrazide (186 mg, 1.0 mmol) in ethanol (3 mL) was added one drop of hydrogen chloride (12N). The resulting solution was stirred for 1 h at room temperature. The resulting mixture was concentrated under vacuum. The residue was applied onto a silica gel column with ethyl acetate/petroleum ether (1:5). This resulted in 230 mg (66%) of the title compound as a white solid. LC-MS (ESI, m/z): $[M+H]^+$=348.1.

Methyl 5-(2-[2-chloro-4-[(4-methoxyphenyl)methoxy] phenyl]-1-methylcyclopropyl) pyridine-3-carboxylate (Compound 11b)

To a solution of Compound 11a (100 mg, 0.29 mmol) and 2-chloro-1-ethenyl-4-[(4-methoxyphenyl) methoxy] benzene (158 mg, 0.58 mmol) in dioxane (2 mL) was added potassium carbonate (46 mg, 0.33 mmol). The resulting solution was stirred for 6 h while the temperature was maintained at 110° C. The solids were filtered out. The resulting mixture was concentrated under vacuum. The residue was applied onto a silica gel column with ethyl acetate/petroleum ether (1:5). This resulted in 40 mg (32%) of the title compound as a white. LC-MS (ESI, m/z): $[M+H]^+$=438.3.

Methyl 5-[2-(2-chloro-4-hydroxyphenyl)-1-methylcyclopropyl] pyridine-3-carboxylate (Compound 11c)

To a solution of Compound 11b (180 mg, 0.42 mmol) in dichloromethane (5 mL) was added trifluoroacetic acid (0.5 mL). The resulting solution was stirred for 0.5 h at room temperature. The resulting mixture was concentrated under vacuum. The residue was applied onto a silica gel column with ethyl acetate/petroleum ether (1:4). This resulted in 100 mg (74%) of the title compound as a white solid. LC-MS (ESI, m/z): $[M+H]^+$=318.2.

Methyl 5-[2-(2-chloro-4-[[3-(2,6-dichlorophenyl)-5-(propan-2-yl)-1,2-oxazol-4-yl]methoxy] phenyl)-1-methylcyclopropyl] pyridine-3-carboxylate (Compound 11d)

To a solution of Compound 11c (150 mg, 0.47 mmol), Compound INT-001 (135 mg, 0.47 mmol) and triphenylphosphane (186 mg, 0.71 mmol) in tetrahydrofuran (5 mL) was added DIAD (142 mg, 0.70 mmol) dropwise at 0° C. The resulting solution was allowed warm to room temperature and stirred overnight. The resulting mixture was concentrated under vacuum. The residue was applied onto a silica gel column with ethyl acetate/petroleum ether (1:5). This resulted in 100 mg (36%) of the title compound as a white solid. LC-MS (ESI, m/z): $[M+H]^+$=587.2.

5-[2-(2-Chloro-4-[[3-(2,6-dichlorophenyl)-5-(propan-2-yl)-1,2-oxazol-4-yl]methoxy] phenyl)-1-methylcyclopropyl] pyridine-3-carboxylic Acid (Compound IV-05)

To a solution of Compound 11d (120 mg, 0.20 mmol) in a mixed solvent of methanol (1 mL) and tetrahydrofuran (1 mL) was added a solution of sodium hydroxide (41 mg, 1.03 mmol) in water (1 mL). The resulting solution was stirred for 1 h at 50° C. The pH value of the solution was adjusted to 3 with hydrogen chloride (2 N). The resulting mixture was concentrated under vacuum. The crude product was purified by Prep-HPLC with the following conditions (2#-AnalyseHPLC-SHIMADZU HPLC-10)): Column,)(Bridge Shield RP18 OBD Column, 5 um, 19*150 mm; Mobile Phase, Water (0.05% $NH_3.H_2O$) and ACN (20.0% ACN up to 47.0% in 7 min); Detector, UV 220 nm. This resulted in 10 mg (9%) of the title compound as a white solid. LC-MS (ESI, m/z): $[M+H]^+$=573.3. $^1$HNMR (300 MHz, $CD_3OD$-$d_4$, ppm): δ 8.97 (s, 1H), 8.81 (s, 1H), 8.45 (s, 1H), 7.56-7.42 (m, 3H), 7.18-7.13 (m, 1H), 6.87 (s, 1H), 6.77-6.73 (m, 1H), 4.88 (s, 2H), 3.50-3.40 (m, 1H), 2.41-2.31 (m, 1H), 1.64-1.61 (m, 1H), 1.43 (d, J=6.9 Hz, 6H), 1.42-1.40 (m, 1H), 1.12 (s, 3H).

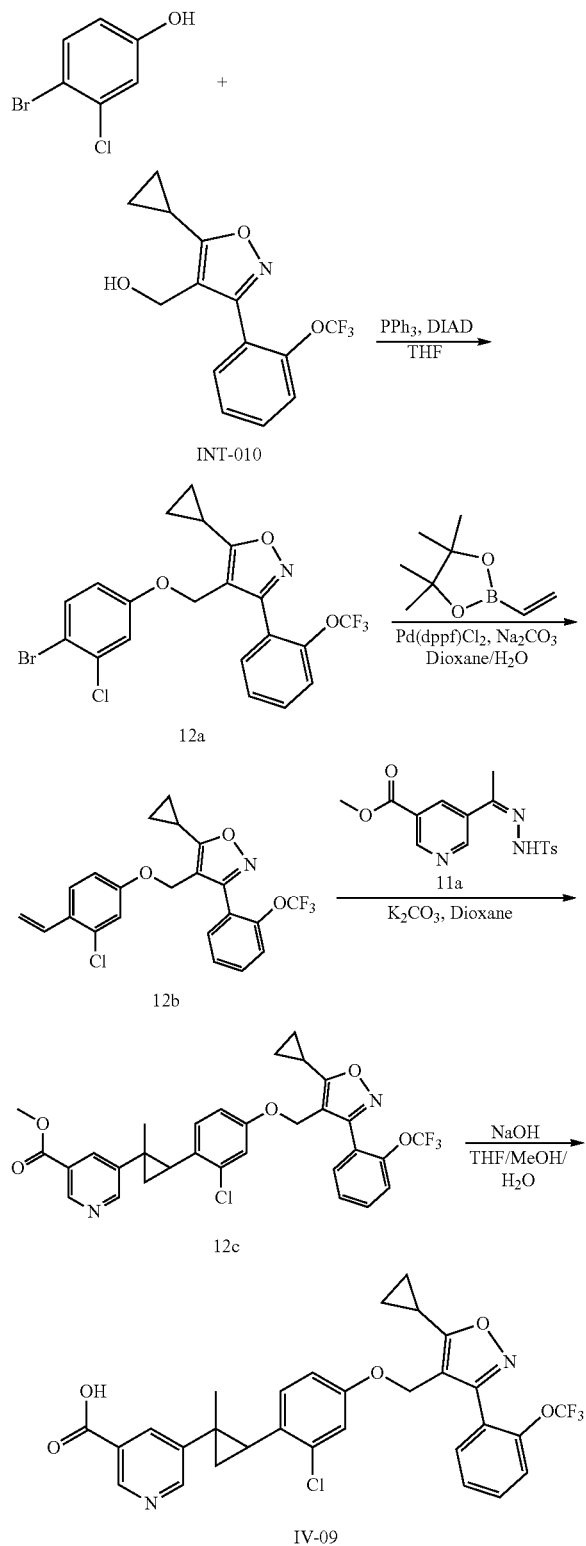

Experimental Details for Compound IV-09 (Scheme 12)

4-(4-Bromo-3-chlorophenoxymethyl)-5-cyclopropyl-3-[2-(trifluoromethoxy) phenyl]-1,2-oxazole (Compound 12a)

To a solution of Compound INT-010 (299 mg, 1.0 mmol), 4-bromo-3-chlorophenol (206 mg, 0.99 mmol) and triphenylphosphane (393 mg, 1.50 mmol) tetrahydrofuran (5 mL) was added DIAD (303 mg, 1.50 mmol) dropwise at 0° C. The resulting solution was allowed warm to room temperature and stirred for another 2 h. The resulting mixture was concentrated under vacuum. The residue was applied onto a silica gel column with ethyl acetate/petroleum ether (1:10). This resulted in 370 mg (76%) of the title compound as a white solid. LC-MS (ESI, m/z): [M+H]$^+$=488.1, 490.1.

4-(3-Chloro-4-ethenylphenoxymethyl)-5-cyclopropyl-3-[2-(trifluoromethoxy) phenyl]-1,2-oxazole (Compound 12b)

To a solution of Compound 12a (380 mg, 0.78 mmol) and 2-ethenyl-4,4,5,5-tetramethyl-1,3,2-dioxaborolane (372 mg, 2.42 mmol) in a mixed solvent of dioxane (3 mL) and water (1 mL) was added Pd(dppf)Cl$_2$ (29 mg, 0.04 mmol) and sodium carbonate (128 mg, 1.21 mmol). The resulting solution was stirred for 2 h at 100° C. under N$_2$ atmosphere. The reaction was then quenched by the addition of 5 mL of water. The resulting solution was extracted with 3×5 mL of dichloromethane. The organic layers were combined and washed with water and brine, then dried over anhydrous sodium sulfate, and concentrated under vacuum. The residue was applied onto a silica gel column with ethyl acetate/petroleum ether (1:10). This resulted in 160 mg (47%) of the title compound as a white solid. LC-MS (ESI, m/z): [M+H]$^+$= 436.0.

Methyl 5-[2-[2-chloro-4-([5-cyclopropyl-3-[2-(trifluoromethoxy) phenyl]-1,2-oxazol-4-yl] methoxy) phenyl]-1-methylcyclopropyl] pyridine-3-carboxylate (Compound 12c)

To a solution of Compound 12b (200 mg, 0.46 mmol) in dioxane (5 mL) was added Compound 11a (239 mg, 0.69 mmol) and potassium carbonate (127 mg, 0.92 mmol). The resulting solution was stirred overnight at 100° C. The solids were filtered out. The resulting mixture was concentrated under vacuum. The residue was applied onto a silica gel column with ethyl acetate/petroleum ether (1:3). This resulted in 60 mg (22%) of the title compound as a white solid. LC-MS (ESI, m/z): [M+H]+=599.1.

5-[2-[2-Chloro-4-([5-cyclopropyl-3-[2-(trifluoromethoxy) phenyl]-1,2-oxazol-4-yl] methoxy) phenyl]-1-methylcyclopropyl] pyridine-3-carboxylic Acid (Compound IV-09)

To a solution of Compound 12c (60 mg, 0.10 mmol) in a mixed solvent of tetrahydrofuran (1 mL), methanol (1 mL) and water (1 mL) was added sodium hydroxide (26.7 mg, 0.67 mmol). The resulting solution was stirred for 1 h at 50° C. The pH value of the solution was adjusted to 3 with hydrogen chloride (2 N). The resulting mixture was concentrated under vacuum. The residue was applied onto a silica gel column with dichloromethane/methanol (15:1). This resulted in 30 mg (51%) of the title compound as a white solid. LC-MS (ESI, m/z): [M+H]⁺=585.1. ¹HNMR (300 MHz, DMSO-d₆, ppm): δ 8.91 (s, 1H), 8.72 (s, 1H), 8.25-8.20 (s, 1H), 7.71-7.48 (m, 4H), 7.28-7.20 (m, 1H), 7.07-7.01 (m, 1H), 6.85-6.78 (m, 1H), 4.97 (s, 2H), 2.46-2.39 (m, 1H), 2.34-2.25 (m, 1H), 1.65-1.56 (m, 1H), 1.48-1.39 (m, 1H), 1.21-1.08 (m, 4H), 1.04 (s, 3H).

Scheme 13 (Compound IV-12)

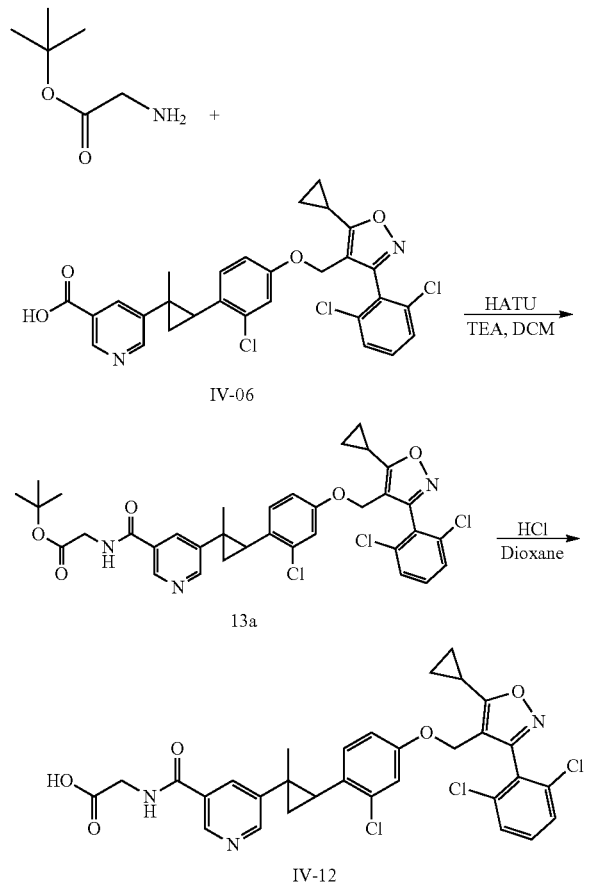

Experimental Details for Compound IV-12 (Scheme 13)

tert-Butyl 2-([5-[2-(2-chloro-4-[[5-cyclopropyl-3-(2,6-dichlorophenyl)-1,2-oxazol 4-yl] methoxy] phenyl)-1-methylcyclopropyl] pyridin-3-yl] formamido) acetate (Compound 13a)

To a solution of Compound IV-06 (20 mg, 0.04 mmol) and triethylamine (10.6 mg, 0.10 mmol) in dichloromethane (1 mL) was added HATU (39.9 mg, 0.10 mmol) at room temperate. The mixture was stirred for 10 min then tert-butyl 2-aminoacetate (14 mg, 0.11 mmol) was added. The resulting solution was stirred for 1 h at room temperature. The resulting mixture was concentrated under vacuum. The residue was applied onto a silica gel column with dichloromethane/methanol (20:1). This resulted in 22 mg (92%) of the title compound as a white solid. LC-MS (ESI, m/z): [M+H]⁺=682.2, 684.3.

2-([5-[2-(2-Chloro-4-[[5-cyclopropyl-3-(2,6-dichlorophenyl)-1,2-oxazol-4-yl]methoxy] phenyl)-1-methylcyclopropyl] pyridin-3-yl] formamido) Acetic Acid (Compound IV-12)

To a solution of Compound 13a (22 mg, 0.03 mmol) in dioxane (2 mL) was added a solution of hydrogen chloride in dioxane (4 mL, 4 M). The resulting solution was stirred for 1 h at room temperature. The resulting mixture was concentrated under vacuum. The residue was applied onto a silica gel column with dichloromethane/methanol (10:1). This resulted in 8 mg (40%) of the title compound as a white solid. LC-MS (ESI, m/z): [M+H]⁺=626.1, 628.1. ¹HNMR (300 MHz, DMSO-d₆, ppm): δ 8.85-8.77 (m, 3H), 8.15 (s, 1H), 7.65-7.52 (m, 3H), 7.22 (d, J=5.7 Hz, 1H), 6.97 (d, J=2.7 Hz, 1H), 6.79-6.75 (m, 1H), 4.93 (s, 2H), 3.84 (d, J=5.4 Hz, 2H), 2.45-2.40 (m, 1H), 2.35-2.28 (m, 1H), 1.65-1.60 (m, 1H), 1.44-1.40 (m, 1H), 1.19-1.10 (m, 4H), 1.05 (s, 3H).

Scheme 14 (Compound IV-15)

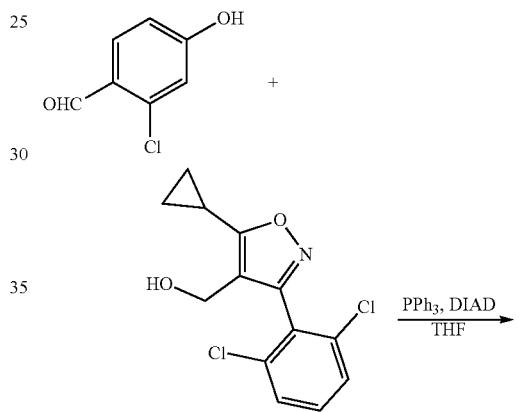

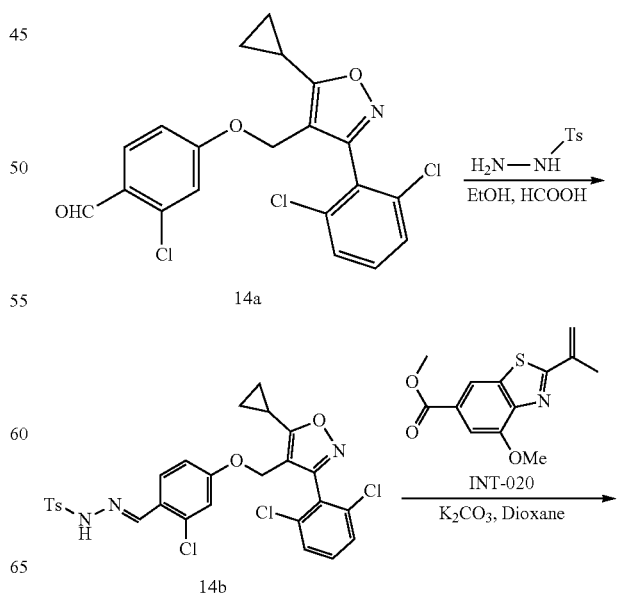

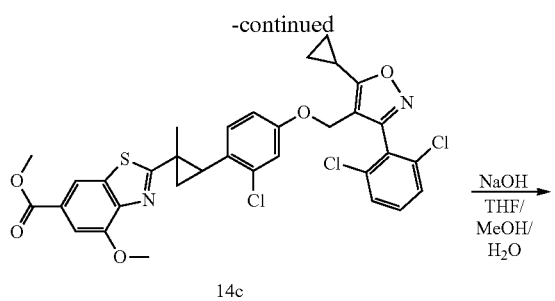

14c

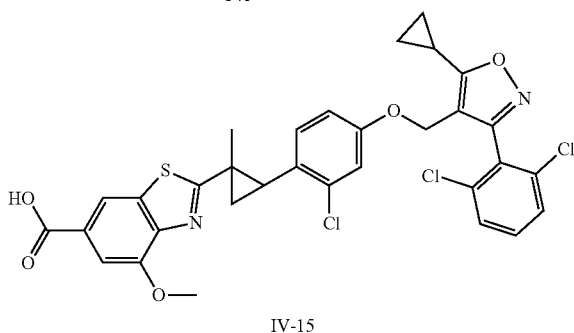

IV-15

Experimental Details for Compound IV-15 (Scheme 14)

2-Chloro-4-[[5-cyclopropyl-3-(2,6-dichlorophenyl)-1,2-oxazol-4-yl] methoxy] benzaldehyde (Compound 14a)

To a solution of 2-chloro-4-hydroxybenzaldehyde (157 mg, 1.0 mmol) and Compound INT-003 (282 mg, 0.99 mmol) in tetrahydrofuran (5 mL) was added triphenylphosphane (393 mg, 1.50 mmol). Then DIAD (303 mg, 1.50 mmol) was added dropwise at 0° C. under $N_2$ atmosphere. The resulting solution was allowed warm to room temperature and stirred for 2 h. The resulting mixture was concentrated under vacuum. The residue was applied onto a silica gel column with ethyl acetate/petroleum ether (1:10). This resulted in 400 mg (94%) of the title compound as a white solid. LC-MS (ESI, m/z): $[M+H]^+$=422.1, 424.1

(E)-1-(4-((3-(2,6-Dichlorophenyl)-5-cyclopropylisoxazol-4-yl) methoxy)-2-chlorobenzylidene)-2-tosylhydrazine (Compound 14b)

To a solution of Compound 14a (260 mg, 0.62 mmol) in ethanol (4 mL) was added 4-methylbenzenesulfonohydrazide (115 mg, 0.62 mmol) and formic acid (0.4 mL). The resulting solution was stirred for 0.5 h at room temperature. The solids were collected by filtration and washed with ethanol. This resulted in 300 mg (83%) of the title compound as a white solid. LC-MS (ESI, m/z): $[M+H]^+$=590.3, 592.3

Methyl 2-[2-(2-chloro-4-[[5-cyclopropyl-3-(2,6-dichlorophenyl)-1,2-oxazol-4-yl]methoxy] phenyl)-1-methylcyclopropyl]-4-methoxy-1,3-benzothiazole-6-carboxylate (Compound 14c)

To a solution of Compound 14b (120 mg, 0.20 mmol) in dioxane (10 mL) was added Compound INT-020 (400 mg, 1.52 mmol) and potassium carbonate (186 mg, 1.35 mmol). The resulting solution was stirred for 3 h at 100° C. The solids were filtered out. The resulting mixture was concentrated under vacuum. The residue was applied onto a silica gel column with ethyl acetate/petroleum ether (1:5). This resulted in 100 mg (73%) of the title compound as a white solid. LC-MS (ESI, m/z): $[M+H]^+$=669.0, 671.1

2-[2-(2-Chloro-4-[[5-cyclopropyl-3-(2,6-dichlorophenyl)-1,2-oxazol-4-yl]methoxy] phenyl)-1-methylcyclopropyl]-4-methoxy-1,3-benzothiazole-6-carboxylic Acid (Compound IV-15)

To a solution of Compound 14c (150 mg, 0.22 mmol) in tetrahydrofuran (2 mL) and methanol (2 mL) was added a solution of sodium hydroxide (45 mg, 1.13 mmol) in water (1 mL). The resulting solution was stirred for 1 h at 50° C. The pH value of the solution was adjusted to 3 with hydrogen chloride (2 N). The resulting mixture was concentrated under vacuum. The residue was applied onto a silica gel column with dichloromethane/methanol (15:1). This resulted in 30 mg (20%) of the title compound as a white solid. LC-MS (ESI, m/z): $[M+H]^+$=655.3, 657.3. $^1$HNMR (300 MHz, DMSO-$d_6$, ppm): δ 8.17 (s, 1H), 7.68-7.50 (m, 4H), 7.24-7.18 (m, 1H), 6.97 (s, 1H), 6.81-6.75 (s, 1H), 4.93 (s, 2H), 3.96 (s, 3H), 2.78-2.70 (m, 1H), 2.50-2.42 (m, 1H), 1.98-1.90 (m, 1H), 1.75-1.65 (m, 1H), 1.30-1.04 (m, 7H).

Scheme 15 (Compound IV-19)

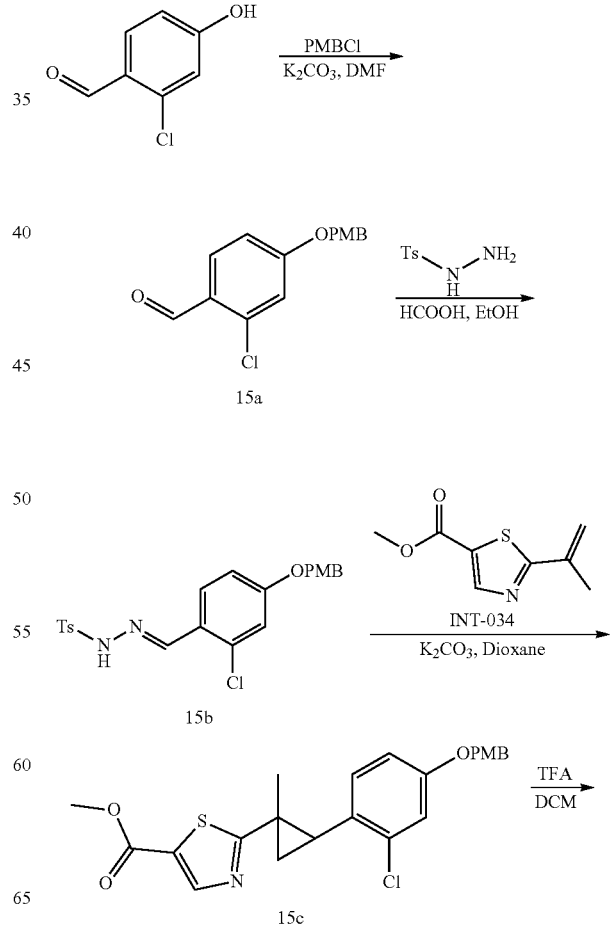

-continued

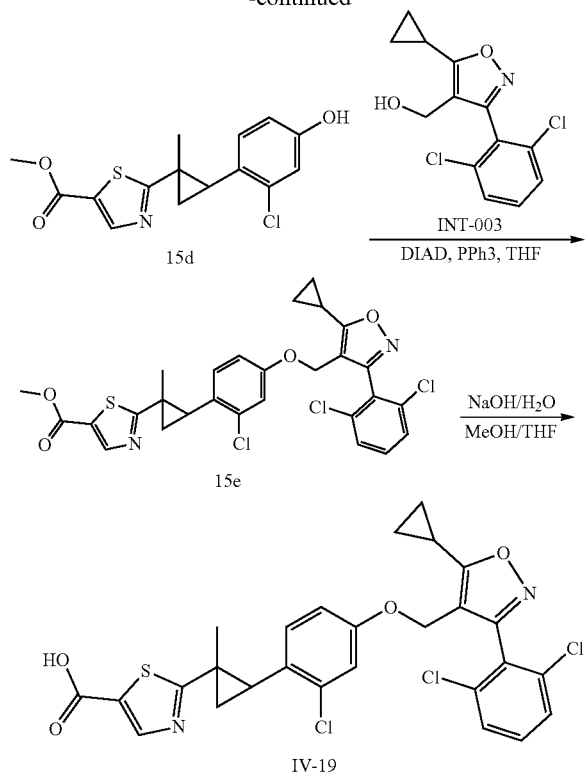

Experimental Details for Compound IV-19 (Scheme 15)

2-Chloro-4-(4-methoxybenzyloxy) benzaldehyde (Compound 15a)

To a solution of 2-chloro-4-hydroxybenzaldehyde (2 g, 12.8 mmol) in DMF (40 mL) was added 1-(chloromethyl)-4-methoxybenzene (2.1 g, 13.4 mmol) and potassium carbonate (2.7 g, 19.4 mmol). The resulting mixture was stirred for 1 h at 60° C. The reaction was then quenched by the addition of water (10 mL). The resulting solution was extracted with 3×15 mL of ethyl acetate and the organic layers were combined. The residue was concentrated under vacuum after dried over anhydrous sodium sulfate. The crude product was purified by re-crystallization from hexane. This resulted in 2.2 g (62%) of the title compound as a white solid. LC-MS (ESI, m/z): [M+H]$^+$=277.2.

(E)-N'-(2-Chloro-4-(4-methoxybenzyloxy) benzylidene)-4-methylbenzenesulfonohydrazide (Compound 15b)

To a solution of a Compound 15a (2.2 g, 7.95 mmol) in ethanol (25 mL) was added formic acid (0.1 mL) and 4-methylbenzene-1-sulfonohydrazide (1.55 g, 8.32 mmol). The resulting solution was stirred for 1 h at room temperature. The solids were collected by filtration and washed with cooled ethanol. The solid was dried in an oven under reduced pressure. This resulted in 2.5 g (71%) of the title compound as a white solid. LC-MS (ESI, m/z): [M+H]$^+$=445.2.

Methyl 2-(2-(2-chloro-4-(4-methoxybenzyloxy) phenyl)-1-methylcyclopropyl) thiazole-5-carboxylate (Compound 15c)

To a solution of methyl 2-(prop-1-en-2-yl)-1,3-thiazole-5-carboxylate (300 mg, 1.64 mmol) in dioxane (6 mL) was added Compound 15b (1.08 g, 2.35 mmol, 1.50 equiv) and potassium carbonate (450 mg, 3.23 mmol). The resulting mixture was stirred for 4 h at 100° C. The resulting mixture was concentrated under vacuum after filtration. The residue was applied onto a silica gel column with ethyl acetate/petroleum ether (25:75). This resulted in 450 mg (62%) of the title compound as a yellow oil. LC-MS (ESI, m/z): [M+H]$^+$=444.1.

Methyl 2-(2-(2-chloro-4-hydroxyphenyl)-1-methylcyclopropyl) thiazole-5-carboxylate (Compound 15d)

To a solution of Compound 15c (650 mg, 1.46 mmol) in dichloromethane (10 mL) was added trifluoroacetic acid (1 mL). The resulting solution was stirred for 10 min at room temperature. The resulting mixture was concentrated under vacuum. The residue was applied onto a silica gel column with ethyl acetate/petroleum ether (27:73). This resulted in 300 mg (63%) of the title compound as a yellow oil. LC-MS (ESI, m/z): [M+H]$^+$=324.4.

Methyl 2-(2-(2-chloro-4-((5-cyclopropyl-3-(2,6-dichlorophenyl) isoxazol-4-yl) methoxy) phenyl)-1-methylcyclopropyl) thiazole-5-carboxylate (Compound 15e)

To a solution of Compound 15d (200 mg, 0.62 mmol), Compound INT-003 (174 mg, 0.61 mmol) and triphenylphosphane (194 mg, 0.74 mmol) in THF (4 mL) was added DIAD (150 mg, 1.15 mmol) dropwise at 0° C. The resulting solution was stirred for 2 h at room temperature. The resulting mixture was concentrated under vacuum. The residue was applied onto a silica gel column with ethyl acetate/petroleum ether (23:77). This resulted in 250 mg (69%) of the title compound as a yellow solid. LC-MS (ESI, m/z): [M+H]$^+$=591.0.

2-(2-(2-Chloro-4-((5-cyclopropyl-3-(2,6-dichlorophenyl) isoxazol-4-yl) methoxy) phenyl)-1-methylcyclopropyl) thiazole-5-carboxylic Acid (Compound IV-19)

To a solution of Compound 15e (60 mg, 0.10 mmol) in a mixed solution of methanol/THF (2 mL, 1:1) was added a solution of sodium hydroxide (20 mg, 0.50 mmol) in water (0.5 ml). The resulting solution was stirred for 2 h at 50° C. The pH value of the solution was adjusted to 6 with hydrogen chloride (2 N). The resulting mixture was concentrated under vacuum. The resulting solution was diluted with 2 mL of water. The residue was applied onto a C18 gel column with CH$_3$CN/Water (46:54). This resulted in 16.5 mg (28%) of the title compound as a white solid. LC-MS (ESI, m/z): [M+Na]$^+$=597.2. $^1$HNMR (300 MHz, DMSO-d$_6$, ppm): δ 7.70 (s, 1H), 7.63-7.48 (m, 3H), 7.18-7.08 (m, 1H), 6.79-6.72 (m, 1H), 6.62-6.59 (m, 1H), 4.91-4.78 (m, 2H), 2.45-2.36 (m, 2H), 2.02-1.98 (m, 1H), 1.73 (s, 3H), 1.50-1.45 (m, 1H), 1.18-1.04 (m, 4H).

Following the procedure described above for Scheme 11-14 and substituting the appropriate reagents, starting materials and purification methods known to those skilled in the art, the following compounds of the present invention were prepared.

TABLE 4

| Compound | Structure | Scheme | LC-MS (M + H)+ | 1HNMR (ppm) |
|---|---|---|---|---|
| IV-01 | 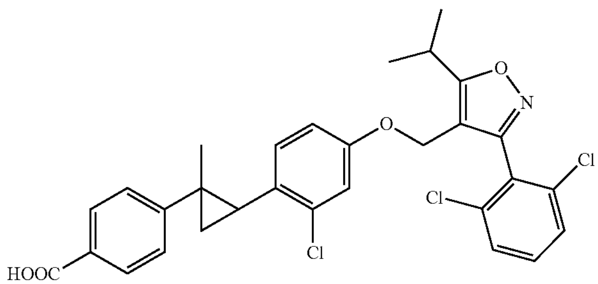 [SMILES: CC(C)c1onc(-c2c(Cl)cccc2Cl)c1COc1ccc(C2CC2(C)c2ccc(C(=O)O)cc2)c(Cl)c1] | 11 | 570.1 | CD3OD-d4: δ 7.97-7.97 (m, 2H), 7.5-7.44 (m, 5H), 7.15-7.13 (d, J = 8.0 Hz, 1H), 6.85-6.84 (d, J = 4.0 Hz, 1H), 6.74-6.72 (m, 1H), 4.86 (s, 2H), 3.48-3.41 (m, 1H), 2.37-2.33 (m, 1H), 1.59-1.55 (m, 1H), 1.44 (d, J = 6.4 Hz, 6H), 1.37-1.33 (m, 1H), 1.09 (s, 3H). |
| IV-02 | 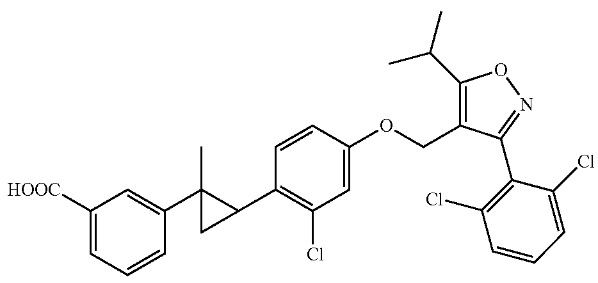 [SMILES: CC(C)c1onc(-c2c(Cl)cccc2Cl)c1COc1ccc(C2CC2(C)c2cccc(C(=O)O)c2)c(Cl)c1] | 11 | 570.2 | CD3OD-d4: δ 8.15 (s, 1H), 7.88 (d, J = 7.6 Hz, 1H), 7.72 (d, J = 7.6 Hz, 1H), 7.55-7.53 (m, 2H), 7.50-7.42 (m, 3H), 7.15 (d, J = 8.4 Hz, 1H), 6.86 (d, J = 2.4 Hz, 1H), 6.74-6.72 (m, 1H), 3.50-3.42 (m, 1H), 2.32 (t, J = 8.4 Hz, 1H), 1.53-1.50 (m, 1H), 1.44 (d, J = 7.2 Hz, 6H), 1.09 (s, 3H). |
| IV-03 | 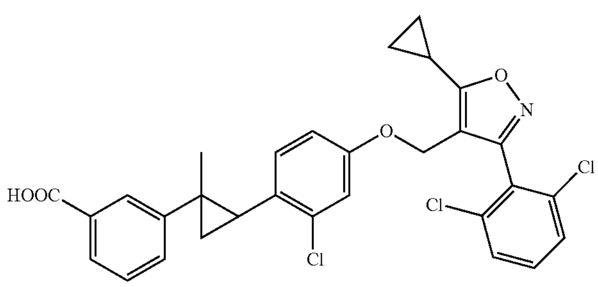 [SMILES: CC1(c2cccc(C(=O)O)c2)CC1c1ccc(OCc2c(-c3c(Cl)cccc3Cl)noc2C2CC2)cc1Cl] | 11 | 568.2 | DMSO-d6: δ 7.98 (s, 1H), 7.77 (d, J = 7.6 Hz, 1H), 7.64-7.59 (m, 2H), 7.58-7.53 (m, 2H), 7.41-7.38 (m, 1H), 7.20 (d, J = 8.8 Hz, 1H), 6.96 (d, J = 2.4 Hz, 1H), 6.77-6.74 (m, 1H), 4.93 (s, 2H), 2.57-2.52 (m, 1H), 2.26-2.22 (m, 1H), 1.47-1.45 (m, 1H), 1.37-1.35 (m, 1H), 1.20-1.13 (m, 4H), 1.01 (s, 3H). |
| IV-04 | 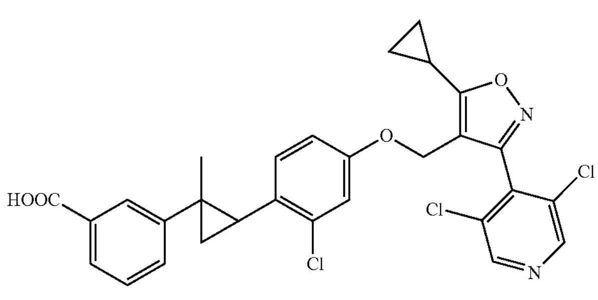 [SMILES: CC1(c2cccc(C(=O)O)c2)CC1c1ccc(OCc2c(-c3c(Cl)cncc3Cl)noc2C2CC2)cc1Cl] | 12 | 571.2 | CD3OD-d4: δ 8.68 (s, 2H), 8.15 (s, 1H), 7.88 (d, J = 7.6 Hz, 1H), 7.71 (d, J = 7.6 Hz, 1H), 7.44-7.41 (m, 1H), 7.16 (d, J = 8.4 Hz, 1H), 6.86 (d, J = 2.8 Hz, 1H), 6.72-6.69 (m, 1H), 5.00 (s, 2H), 2.41-2.31 (m, 2H), 1.54-1.50 (m, 1H), 1.32-1.25 (m, 5H), 1.08 (s, 3H). |

TABLE 4-continued
| Compound | Structure | Scheme | LC-MS (M + H)+ | 1HNMR (ppm) |
|---|---|---|---|---|
| IV-06 | 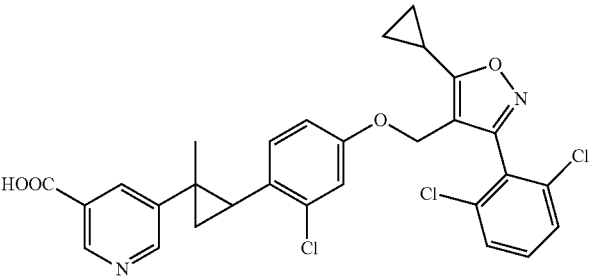 [SMILES: CC1(c2cncc(C(=O)O)c2)CC1c1ccc(OCc2c(-c3c(Cl)cccc3Cl)noc2C2CC2)cc1Cl] | 12 | 569.3, 571.3 | DMSO-d6: δ 13.50 (s, 1H), 8.92 (s, J = 1.8 Hz, 1H), 8.83 (d, J = 2.1 Hz, 1H), 8.23 (d, J = 2.1 Hz, 1H), 7.65-7.52 (m, 3H), 7.22 (d, J = 8.7 Hz, 1H), 6.98 (d, J = 2.4 Hz, 1H), 6.79-6.75 (m, 1H), 4.93 (s, 2H), 2.46-2.40 (m, 1H), 2.33-2.27 (m, 1H), 1.64-1.60 (m, 1H), 1.42 (t, J = 6.3 Hz, 1H), 1.21-1.10 (m, 4H), 1.03 (s, 3H). |
| IV-07 | 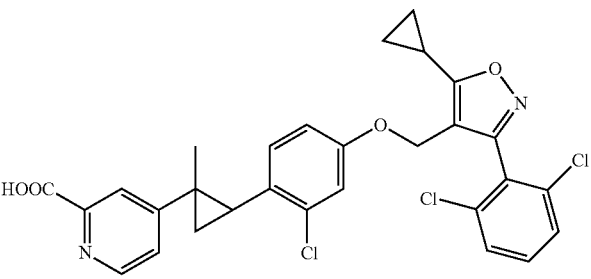 [SMILES: CC1(c2ccnc(C(=O)O)c2)CC1c1ccc(OCc2c(-c3c(Cl)cccc3Cl)noc2C2CC2)cc1Cl] | 12 | 569.2, 571.1 | DMSO-d6: δ 8.65-8.58 (m, 1H), 7.96 (s, 1H), 7.69-7.51 (m, 4H), 7.25-7.17 (m, 1H), 6.96 (m, 1H), 6.81-6.74 (m, 1H), 4.93 (s, 2H), 2.42-2.39 (m, 1H), 2.38-2.25 (m, 1H), 1.17-1.63 (m, 1H), 1.55-1.49 (m, 1H), 1.24-1.09 (m, 4H), 1.03 (s, 3H). |
| IV-08 | 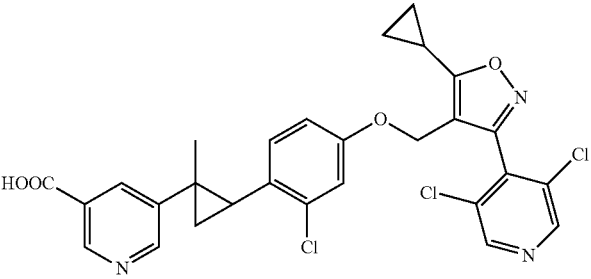 [SMILES: CC1(c2cncc(C(=O)O)c2)CC1c1ccc(OCc2c(-c3c(Cl)cncc3Cl)noc2C2CC2)cc1Cl] | 12 | 570.3 | DMSO-d6: δ 8.92-8.82 (m, 4H), 8.24-8.22 (m, 1H), 7.23-7.20 (m, 1H), 6.98-6.97 (m, 1H), 6.76-6.72 (m, 1H), 5.01 (s, 2H), 2.46-2.42 (m, 1H), 2.33-2.26 (m, 1H), 1.65-1.60 (m, 1H), 1.45-1.41 (m, 1H), 1.25-1.15 (m, 4H), 1.04 (s, 3H). |
| IV-10 | 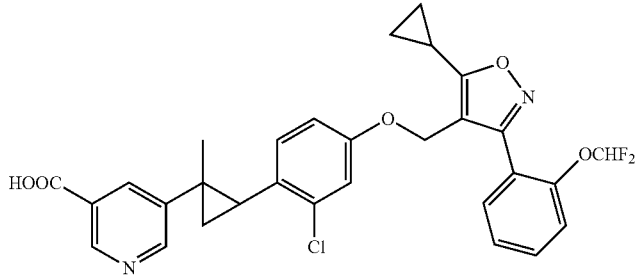 [SMILES: CC1(c2cncc(C(=O)O)c2)CC1c1ccc(OCc2c(-c3ccccc3OC(F)F)noc2C2CC2)cc1Cl] | 12 | 567.3 | DMSO-d6: δ 8.89 (s, 1H), 8.71-8.67 (m, 1H), 8.20 (s, 1H), 7.62-7.55 (m, 1H), 7.62-7.55 (m, 1H), 7.52-7.47 (m, 1H), 7.40-7.33 (m, 2H), 7.25-7.19 (m, 2H), 7.03-6.99 (m, 1H), 6.84-6.79 (m, 1H), 4.97 (s, 2H), 2.45-2.32 (m, 1H), 2.30-2.20 (m, 1H), 2.60-2.50 (m, 1H), 2.42-2.33 (m, 1H), 1.19-1.08 (m, 4H), 1.03 (s, 3H). |
| IV-11 | 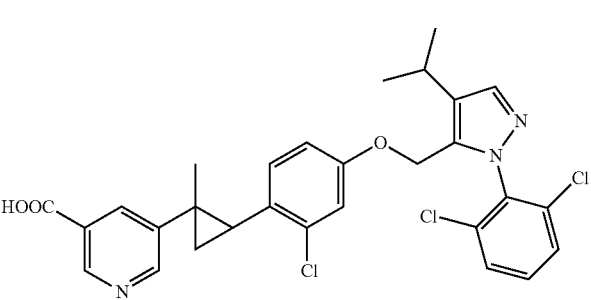 [SMILES: CC(C)c1cnn(-c2c(Cl)cccc2Cl)c1COc1ccc(C2CC2(C)c2cncc(C(=O)O)c2)c(Cl)c1] | 12 | 570.1, 572.1 | DMSO-d6: δ 8.91 (s, 1H), 8.78 (s, 1H), 8.22-8.18 (m, 1H), 7.74 (s, 1H), 7.69-7.63 (m, 2H), 7.58-7.50 (m, 1H), 7.22-7.16 (m, 1H), 7.03-6.97 (m, 1H), 6.79-6.72 (m, 1H), 4.98 (s, 2H), 3.08-2.97 (m, 1H), 2.32-2.22 (m, 1H), 1.64-1.53 (m, 1H), 1.45-1.35 (m, 1H), 1.24 (d, J = 6.9 Hz, 6H), 1.02 (s, 3H). |

TABLE 4-continued

| Compound | Structure | Scheme | LC-MS (M + H)+ | 1HNMR (ppm) |
|---|---|---|---|---|
| IV-13 | 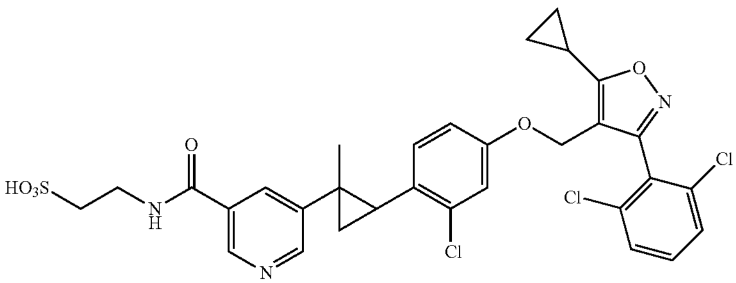 [SMILES: CC1(c2cncc(C(=O)NCCS(=O)(=O)O)c2)CC1c1ccc(OCc2c(-c3c(Cl)cccc3Cl)noc2C2CC2)cc1Cl] | 13 | 676.1, 678.1 | DMSO-d6: δ 8.84-8.72 (m, 2H), 8.12 (s, 1H), 7.55-7.40 (m, 3H), 7.24-7.15 (m, 1H), 6.94 (s, 1H), 6.80-6.71 (m, 1H), 4.92 (s, 2H), 3.57-3.52 (m, 2H), 2.75-2.70 (m, 2H), 2.46-2.40 (m, 1H), 2.32-2.27 (m, 1H), 1.62-1.57 (m, 1H), 1.42-1.37 (m, 1H), 1.28-1.10 (m, 4H), 1.04 (s, 3H). |
| IV-14 | 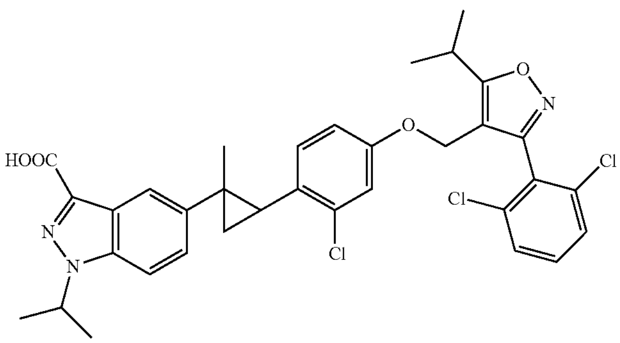 [SMILES: CC(C)c1onc(-c2c(Cl)cccc2Cl)c1COc1ccc(C2CC2(C)c2ccc3c(c2)c(C(=O)O)nn3C(C)C)c(Cl)c1] | 12 | 652.3 | DMSO-d6: δ 13.55 (s, 1H), 8.09 (s, 1H), 7.73 (d, J = 9.0 Hz, 1H), 7.67-7.59 (m, 2H), 7.59-7.51 (m, 1H), 7.45-7.42 (m, 1H), 7.18 (d, J = 8.4 Hz, 1H), 6.94 (d, J = 2.1 Hz, 1H), 6.95-6.94 (m, 1H), 5.93-5.89 (m, 1H), 4.87 (s, 1H), 3.49-3.42 (m, 1H), 2.31-2.27 (m, 1H), 1.53 (d, J = 6.6 Hz, 6H), 1.46-1.44 (m, 1H), 1.33 (m, 7H), 1.01 (s, 3H). |
| IV-16 | 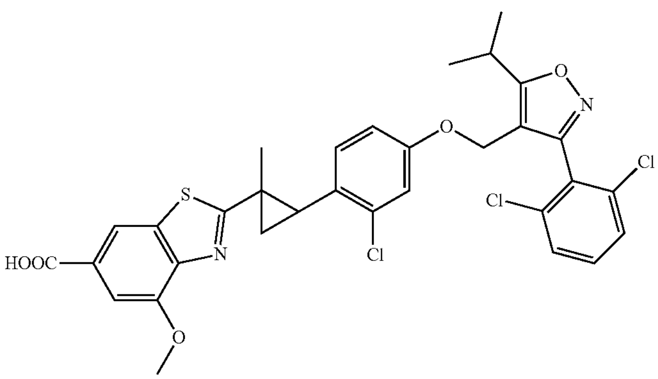 [SMILES: COc1cc(C(=O)O)cc2sc(C3(C)CC3c3ccc(OCc4c(-c5c(Cl)cccc5Cl)noc4C(C)C)cc3Cl)nc12] | 11 | 657.2 | DMSO-d6: δ 8.15 (s, 1H), 7.63-7.60 (m, 4H), 7.56-7.54 (m, 1H), 7.21-7.18 (m, 1H), 6.94-6.93 (m, 1H), 4.8 (m, 2H), 3.95 (s, 3H), 2.50-2.49 (m, 1H), 2.01-1.98 (m, 1H), 1.96-1.94 (m, 1H), 1.33-1.31 (m, 6H), 1.21-1.20 (m, 1H), 1.17 (s, 3H). |
| IV-17 | 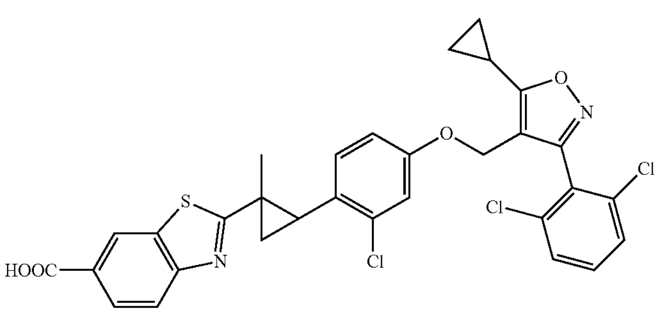 [SMILES: CC1(c2nc3ccc(C(=O)O)cc3s2)CC1c1ccc(OCc2c(-c3c(Cl)cccc3Cl)noc2C2CC2)cc1Cl] | 14 | 625.1, 627.1 | DMSO-d6: δ 8.57 (s, 1H), 8.13 (s, 1H), 8.02-8.00 (m, 1H), 7.88-7.84 (m, 1H), 7.62-7.60 (m, 2H), 7.60-7.58 (m, 1H), 7.23-7.20 (m, 1H), 6.96-6.95 (m, 1H), 6.79-6.76 (m, 1H), 4.92 (m, 2H), 2.78-2.75 (m, 1H), 2.26-2.20 (m, 1H), 1.22-1.15 (m, 6H), 1.12-1.05 (m, 2H). |

TABLE 4-continued

| Compound | Structure | Scheme | LC-MS (M + H)+ | 1HNMR (ppm) |
|---|---|---|---|---|
| IV-18 | 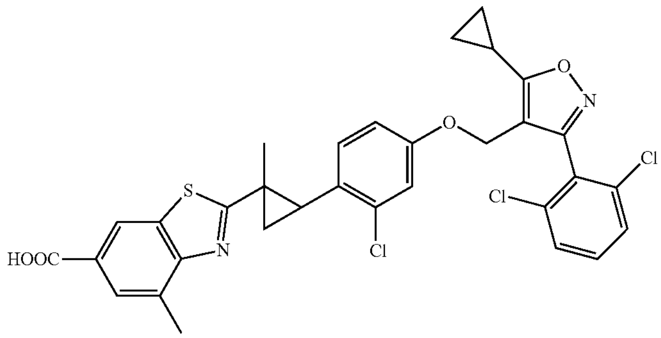 [SMILES: Cc1cc(C(=O)O)cc2sc(C3(C)CC3c3ccc(OCc4c(-c5c(Cl)cccc5Cl)noc4C4CC4)cc3Cl)nc12] | 12 | 639.2 | DMSO-d6: 8.26 (s, 1H), 7.70 (s, 1H), 7.55-7.49 (m, 3H), 7.25-7.23 (m, 1H), 6.66-6.61 (m, 2H), 4.76 (s, 2H), 2.64-2.60 (m, 2H), 2.34 (s, 3H), 2.22-2.20 (m, 1H), 1.83 (s, 3H), 1.64-1.61 (m, 1H), 1.09-1.06 (m, 5H). |
| IV-20 | 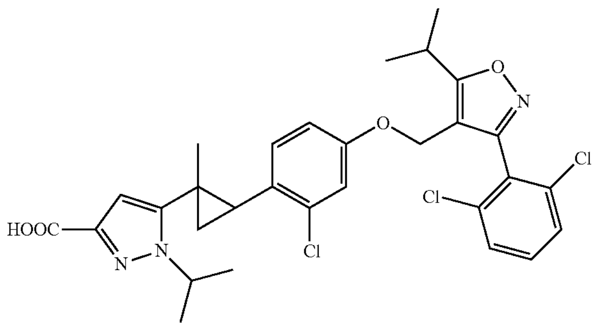 [SMILES: CC(C)c1onc(-c2c(Cl)cccc2Cl)c1COc1ccc(C2CC2(C)c2cc(C(=O)O)nn2C(C)C)c(Cl)c1] | 12 | 602.2 | DMSO-d6: δ 13.26 (s, 1H), 7.69-7.52 (m, 3H), 7.15-7.08 (m, 1H), 6.90 (s, 1H), 6.72-6.62 (m, 2H), 5.51-5.40 (m, 1H), 4.86 (s, 2H), 3.51-3.34 (m, 2H), 2.31-2.28 (m, 1H), 1.50-1.28 (m, 12H), 0.98 (s, 3H). |

Chiral Separation for Compound IV-05-1 and IV-05-2

5-[2-(2-Chloro-4-[[3-(2,6-dichlorophenyl)-5-(propan-2-yl)-1,2-oxazol-4-yl]methoxy] phenyl)-1-methylcyclopropyl] pyridine-3-carboxylic Acid (Compound IV-05-1 and IV-05-2)

Compound IV-05 (80 mg) was separated by Chiral-Prep-HPLC with the following conditions (Prep-HPLC-009): Column, CHIRAL ART Cellulose-SB S-5 um, 2*25 cm, 5 um; Mobile Phase, Hexane (0.1% TFA) and ethanol (hold 50.0% ethanol in 14 min); Detector, UV 220/254 nm. The resulted fractions from two peaks were concentrated by lyophilization. The resulted products were purified by reversed column with CH$_3$CN/Water (0.05% NH$_4$HCO$_3$) again. This resulted in 23.9 mg of Compound IV-05-2 as a white solid and 20.1 mg of Compound IV-05-1 as a white solid.

Compound IV-05-2:
Rt=6.98 min, ee %=99.5%. LC-MS (ESI, m/z): [M+H]+= 571.2. $^1$HNMR (400 MHz, DMSO-d$_6$, ppm) δ 8.87 (s, 1H), 8.7 (s, 1H), 8.19 (s, 1H), 7.61-7.50 (m, 3H), 7.21-7.14 (m, 1H), 6.94 (s, 1H), 6.75-6.67 (m, 1H), 4.87 (s, 2H), 3.50-3.40 (m, 1H), 2.28-2.20 (m, 1H), 1.58-1.51 (m, 1H), 1.40-1.35 (m, 1H), 1.37 (d, J=5.6 Hz, 6H), 1.01 (s, 3H).

Compound IV-05-1:
Rt=7.99 min, ee %=98.6%. LC-MS (ESI, m/z): [M+H]+= 571.2. $^1$HNMR (400 MHz, DMSO-d$_6$, ppm): δ 8.87 (s, 1H), 8.7 (s, 1H), 8.19 (s, 1H), 7.62-7.50 (m, 3H), 7.20-7.15 (m, 1H), 6.94 (s, 1H), 6.74-6.68 (m, 1H), 4.87 (s, 2H), 3.50-3.40 (m, 1H), 2.28-2.20 (m, 1H), 1.59-1.52 (m, 1H), 1.40-1.36 (m, 1H), 1.37 (d, J=5.6 Hz, 6H), 1.00 (s, 3H).

Chiral Separation for Compound IV-06-1 and IV-06-2

5-[2-(2-Chloro-4-[[5-cyclopropyl-3-(2,6-dichlorophenyl)-1,2-oxazol-4-yl]methoxy] phenyl)-1-methylcyclopropyl] pyridine-3-carboxylic Acid (Compound IV-06-1 and IV-06-2)

The crude product IV-06 from hydrolysis of methyl 5-[2-(2-chloro-4-[[5-cyclopropyl-3-(2,6-dichlorophenyl)-1,2-oxazol-4-yl] methoxy] phenyl)-1-methylcyclopropyl] pyridine-3-carboxylate (3.8 g, 6.51 mmol) was purified by Prep-SFC with the following conditions: Column, CHIRAL-PAK IG-03, 2.0 cm I.D*25 cm L, 5 um; Mobile Phase A: CO$_2$: 60, Mobile Phase B: MeOH (2 mM NH$_3$-MeOH): 40; Flow rate, 50 mL/min; Detector, UV 220 nm. The fractions from the first peak was concentrated by lyophilization directly without any further workup. This resulted in 1.15 g of Compound IV-06-1 as a white solid. The fractions from the second peak was purified by reversed column with CH$_3$CN/Water (0.05% NH$_4$HCO$_3$) (7:3) again after lyophilization. This resulted in 750 mg of Compound IV-06-2 as a white solid.

Compound IV-06-1:
Rt=2.15 min, ee %=98.1%. LC-MS (ESI, m/z): [M+H]+= 571.0. $^1$HNMR (400 MHz, CD$_3$OD-d$_4$, ppm): δ 8.96 (d, J=2.0 Hz, 1H), 8.81 (d, J=2.0 Hz, 1H), 8.45-8.44 (m, 1H), 7.53-7.44 (m, 3H), 8.81 (d, J=8.4 Hz, 1H), 6.89 (d, J=2 Hz, 1H), 6.76-6.74 (m, 1H), 4.93 (s, 2H), 2.38-2.32 (m, 2H), 1.62-1.59 (m, 1H), 1.44-1.23 (m, 8H).

Compound IV-06-2:
Rt=2.45 min, ee %=98.9%. LC-MS (ESI, m/z): [M+H]+= 571.2. $^1$HNMR (400 MHz, CD$_3$OD-d$_4$, ppm): 8.93 (s, 1H), 8.76 (d, J=2.0 Hz, 1H), 8.42-8.41 (m, 1H), 7.52-7.43 (m, 3H), 7.15-7.13 (m, 1H), 6.87 (d, J=2.4 Hz, 1H), 6.75-6.72 (m, 1H), 4.91 (s, 2H), 2.37-2.30 (m, 2H), 1.67-1.57 (m, 1H), 1.38-1.35 (m, 1H), 1.21-1.10 (m, 7H).

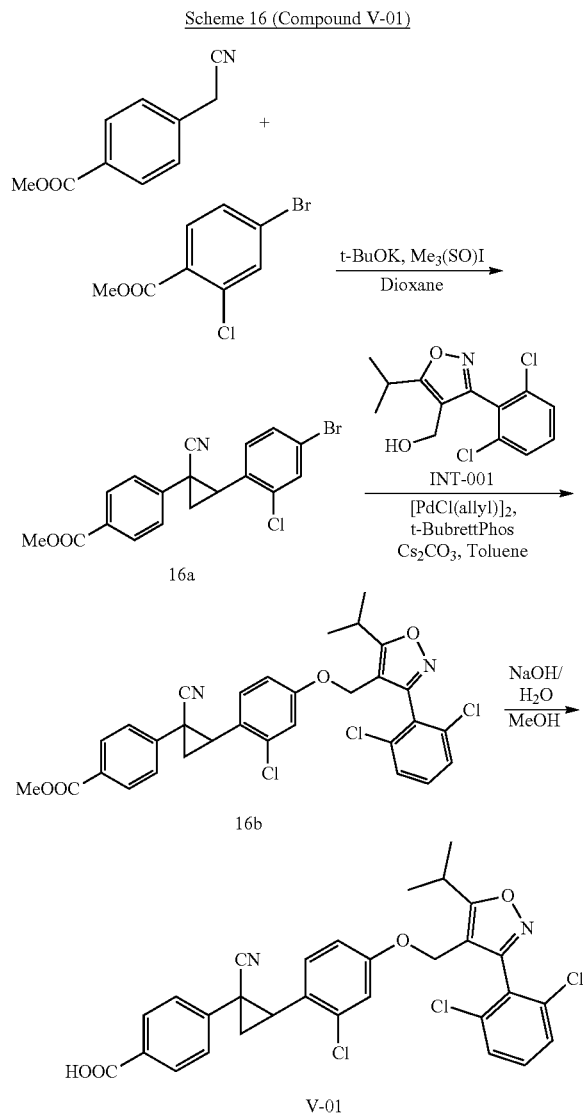

Experimental Details for Compound V-01 (Scheme 16)

Methyl 4-(2-(4-bromo-2-chlorophenyl)-1-cyanocyclopropyl) benzoate (Compound 16a)

To a stirring solution of methyl 4-(cyanomethyl) benzoate (875 mg, 4.99 mmol) in dioxane (30 mL) was added 4-bromo-3-chlorobenzaldehyde (1.30 g, 5.92 mmol). Then t-BuOK (728 mg, 6.50 mmol) was added at −30° C. After stirring for 0.5 h at room temperature, S, S-dimethylmethanesulfinyl iodide (1.65 g, 7.50 mmol) was added at −30° C. The resulting solution was stirred for another 3 h at room temperature. The reaction was then quenched by the addition of 150 mL of HCl (1 M). The resulting solution was extracted with 3×75 mL of ethyl acetate and the organic layers were combined and washed with water and brine, then dried over anhydrous magnesium sulfate and concentrated under vacuum. The residue was applied onto a silica gel column with ethyl acetate/hexane (1:8). The collected fractions were combined and concentrated under vacuum. This resulted in 0.95 g (49%) of the title compound as a colorless solid.

$^1$HNMR (300 MHz, CDCl$_3$, ppm): δ 8.15-8.04 (m, 2H), 7.66 (d, J=2.0 Hz, 1H), 7.55-7.42 (m, 3H), 7.16 (dd, J=0.8, 8.3 Hz, 1H), 3.95 (s, 3H), 2.90 (t, J=8.4 Hz, 1H), 2.30-2.26 (m, 1H), 2.17-2.12 (m, 1H).

Methyl 4-(2-(2-chloro-4-((3-(2,6-dichlorophenyl)-5-isopropylisoxazol-4-yl) methoxy) phenyl)-1-cyanocyclopropyl) benzoate (Compound 16b)

Compound 16a (172 mg, 0.44 mmol), Compound INT-001 (114 mg, 0.40 mmol), t-BuBrettPhos (18 mg, 0.04 mmol), Cs$_2$CO$_3$ (260 mg, 0.80 mmol) and [PdCl(allyl)]$_2$ (6 mg, 0.018 mmol) were added into a 20 mL sealed tube. Toluene (4 mL) was added under N$_2$ atmosphere. The resulting solution was stirred for 3.5 h at 75° C. The reaction was then quenched by the addition of 30 mL of water, extracted with 3×30 mL of ethyl acetate. The organic layers were combined, dried over anhydrous magnesium sulfate and concentrated under vacuum. The residue was applied onto a silica gel column with ethyl acetate/hexane (1:8). The collected fractions were combined and concentrated under vacuum. This resulted in 76 mg (32%) of the title compound as a yellow solid. LC-MS (ES, m/z): [M+H]$^+$=597.3.

4-(2-(2-Chloro-4-((3-(2,6-dichlorophenyl)-5-isopropylisoxazol-4-yl) methoxy) phenyl)-1-cyanocyclopropyl) benzoic Acid (Compound V-01)

To a solution of Compound 16b (76 mg, 0.13 mmol) in methanol (4 mL) was added a solution of sodium hydroxide (10 mg, 2.50 mmol) in water (2 mL). The resulting solution was stirred for 2 h at 50° C. The reaction was diluted with 30 mL of water. The pH value of the solution was adjusted to 1 with HCl (2 M). The resulting solution was extracted with 3×30 mL of ethyl acetate. Then the organic layers were combined, dried over anhydrous magnesium sulfate and concentrated under vacuum. The crude product was purified by Prep-HPLC with the following conditions (2#-AnalyseHPLC-SHIMADZU(HPLC-10)): Column, XSelect CSH Prep C18 OBD Column, 19*250 mm, 5 um; Mobile Phase, Water (0.05% HCl) and ACN (70.0% ACN up to 95.0% in 7 min); Detector, UV 254/220 nm. This resulted in 15.3 mg (21%) of the title compound as a white solid. LC-MS (ES, m/z): [M+H]$^+$=583.2. $^1$HNMR (300 MHz, DMSO-d$_6$, ppm): δ 13.04 (s, 1H), 7.98 (d, J=8.2 Hz, 2H), 7.64-7.54 (m, 5H), 7.35-7.32 (m, 1H), 7.02-7.01 (m, 1H), 6.81-6.78 (m, 1H), 4.90 (s, 2H), 3.50-3.43 (m, 1H), 2.92 (d, J=8.4 Hz, 1H), 2.50-2.45 (m, 1H), 2.29-2.26 (m, 1H), 1.33 (d, J=6.9 Hz, 6H).

Scheme 17 (Compound V-04)

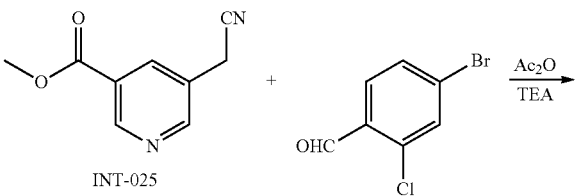

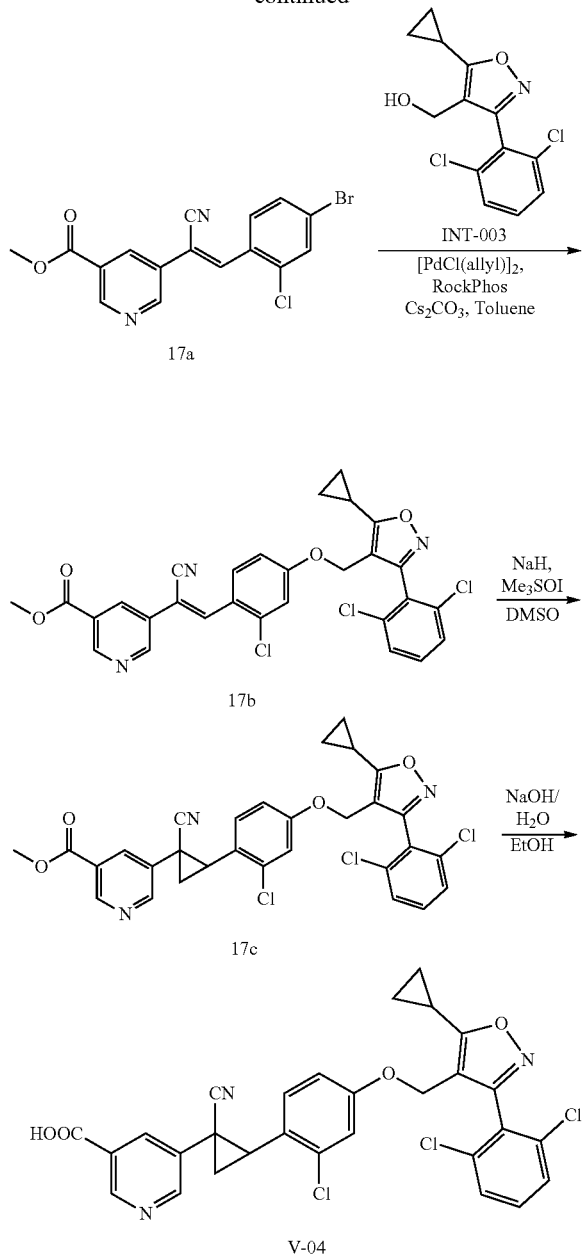

Experimental Details for Compound V-04 (Scheme 17)

Methyl 5-[(1Z)-2-(4-bromo-2-chlorophenyl)-1-cyanoeth-1-en-1-yl] pyridine-3-carboxylate (Compound 17a)

To a solution of Compound INT-025 (650 mg, 3.69 mmol) and 4-bromo-2-chlorobenzaldehyde (850 mg, 3.87 mmol) in acetyl acetate (8 mL) was added triethylamine (1.5 mL, 10.8 mmol). The reaction was stirred for 16 h at 80° C. The mixture was concentrated under vacuum. The residue was applied onto a silica gel column with ethyl acetate/petroleum ether (1:2). This resulted in 0.6 g (43%) of the title compound as a solid. LC-MS (ESI, m/z): [M+H]$^+$=379.2.

Methyl 5-((Z)-2-(4-((3-(2,6-dichlorophenyl)-5-cyclopropylisoxazol-4-yl) methoxy)-2-chlorophenyl)-1-cyanovinyl) pyridine-3-carboxylate (Compound 17b)

To a solution of Compound 17a (120 mg, 0.32 mmol) and Compound INT-003 (90 mg, 0.32 mmol) in toluene (3 mL) was added Cs$_2$CO$_3$ (200 mg, 0.61 mmol), Rockphos (15 mg, 0.03 mmol), [PdCl(allyl)]$_2$ (4 mg, 0.01 mmol). The reaction was stirred for 4 h at 80° C. under N$_2$ atmosphere. The solid was filtered out. The resulting filtrate was concentrated and applied onto a silica gel column with ethyl acetate/petroleum ether (1:1). This resulted in 90 mg (49%) of the title compound as a solid. LC-MS (ESI, m/z): [M+H]$^+$=582.2.

Methyl 5-(2-(4-((3-(2,6-dichlorophenyl)-5-cyclopropylisoxazol-4-yl) methoxy)-2-chlorophenyl)-1-cyanocyclopropyl) pyridine-3-carboxylate (Compound 17c)

To a solution of S, S-dimethylmethanesulfinyl iodide (55 mg, 0.25 mmol) in DMSO (3 mL) was added sodium hydride (15 mg, 0.38 mmol) batchwise at room temperature. The mixture was stirred for 1 h, then Compound 17b (90 mg, 0.16 mmol) was added into above mixture. The reaction was stirred for another 4 h at room temperature. The reaction was quenched by the addition of 30 mL of water. The resulted mixture was extracted with ethyl acetate several times. The organic phases were combined and washed with water and brine, then dried over anhydrous magnesium sulfate and concentrated under vacuum. The residue was applied onto a silica gel column with ethyl acetate/petroleum ether (1:1). This resulted in 50 mg (54%) of the title compound as a solid.

5-[2-(2-Chloro-4-[[5-cyclopropyl-3-(2,6-dichlorophenyl)-1,2-oxazol-4-yl]methoxy] phenyl)-1-cyanocyclopropyl] pyridine-3-carboxylic Acid (Compound V-04)

To a solution of Compound 17c (50 mg, 0.08 mmol) in ethanol (3 mL) was added a solution of sodium hydroxide (10 mg, 0.25 mmol) in water (1 mL). The mixture was stirred for 2 h at 50° C. The pH value of the solution was adjusted to 1 with HCl (2 N). The residue was extracted with ethyl acetate several times. The organic phase was combined and dried over anhydrous magnesium sulfate. The residue was concentrated under vacuum. The crude product was purified by Prep-HPLC with the following conditions (2#-AnalyseHPLC-SHIMADZU(HPLC-10)): Column, XSelect CSH Prep C18 OBD Column, 5 um, 19*150 mm; Mobile Phase, Water (0.05% HCl) and ACN (60.0% ACN up to 73.0% in 8 min); Detector, UV 220/254 nm. This resulted in 3.7 mg (8%) of the title compound as a solid. LC-MS (ESI, m/z): [M+H]$^+$=580.1. $^1$HNMR (300 MHz, DMSO-d$_6$, ppm): δ 9.04 (s, 1H), 8.89 (s, 1H), 8.31-8.30 (m, 1H), 7.64-7.63 (m, 2H), 7.60-7.57 (m, 1H), 7.37-7.34 (m, 1H), 7.06-7.05 (m, 1H), 6.84-6.81 (m, 1H), 4.96 (s, 2H), 3.06-3.03 (m, 1H), 2.50-2.37 (m, 3H), 1.23-1.10 (m, 4H).

Following the procedure described above for Scheme 16 and substituting the appropriate reagents, starting materials and purification methods known to those skilled in the art, the following compounds of the present invention were prepared.

TABLE 5

| Compound | Structure | LC-MS (M + H)+ | 1H NMR (ppm) |
|---|---|---|---|
| V-02 | 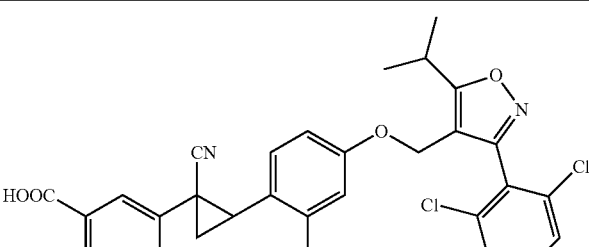 | 581.2 | DMSO-d6: δ 13.14 (s, 1H), 8.07-8.05 (m, 1H), 7.93-7.90 (m, 1H), 7.76-7.47 (m, 5H), 7.35-7.32 (m, 1H), 7.03-7.02 (m, 1H), 6.81-6.80 (m, 1H), 4.90 (s, 2H), 3.53-3.50 (m, 1H), 2.93-2.87 (m, 1H), 2.50-2.40 (m, 1H), 2.24-2.20 (m, 1H), 1.33 (d, J = 7.2 Hz, 6H). |
| V-03 | 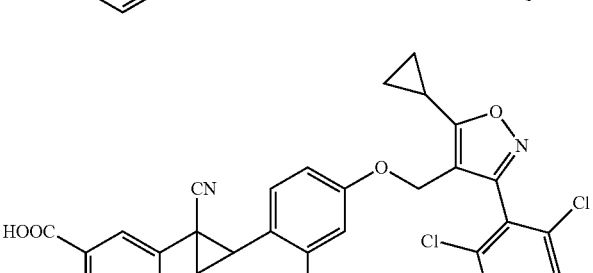 | 579.0 | DMSO-d6: δ 13.14 (s, 1H), 8.07-8.05 (m, 1H), 7.93-7.90 (m, 1H), 7.76-7.46 (m, 5H), 7.35-7.32 (m, 1H), 7.05-7.04 (m, 1H), 6.82-6.81 (m, 1H), 4.95 (s, 2H), 2.93-2.88 (m, 1H), 2.93-2.87 (m, 1H), 2.50-2.43 (m, 1H), 2.24-2.21 (m, 1H), 1.21-1.13 (m, 4H). |

Scheme 18 (Compound V2-01)

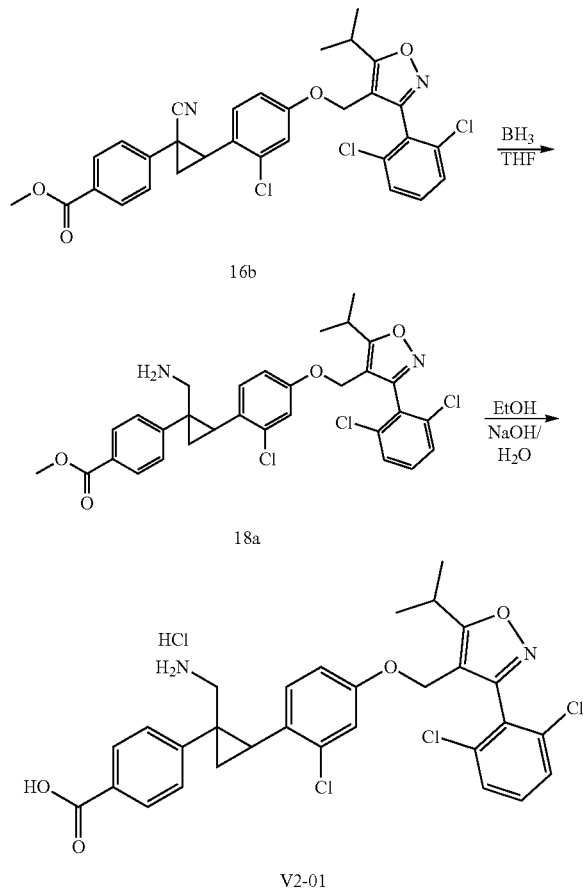

Experimental Details for Compound V2-01 (Scheme 18)

Methyl 4-(1-(aminomethyl)-2-(2-chloro-4-((3-(2,6-dichlorophenyl)-5-isopropylisoxazol-4-yl) methoxy) phenyl) cyclopropyl) benzoate (Compound 18a)

To a solution of Compound 16b (130 mg, 0.22 mmol) in THF (5 mL) was added a solution of BH3 in THF (1.2 mL, 1.20 mmol, 1M) at 0-5° C. The resulting solution was stirred for 16 h at 50° C. The reaction was then quenched by the addition of 20 mL of methanol. The resulting mixture was concentrated under vacuum. This resulted in 90 mg of the title compound as crude product. LC-MS: (ESI, m/z): [M+H]+=601.4.

4-[1-(Aminomethyl)-2-(2-chloro-4-[[3-(2,6-dichlorophenyl)-5-(propan-2-yl)-1,2-oxazol-4-yl] methoxy] phenyl) cyclopropyl] benzoic Acid Hydrochloride (Compound V2-01)

To a solution of Compound 18a (90 mg, 0.15 mmol) in ethanol (3 mL) was added a solution of sodium hydroxide (20 mg, 0.50 mmol) in water (2 mL). The resulting solution was stirred for 2 h at 50° C. The reaction was quenched by the addition of 30 mL of water. The pH value of the solution was adjusted to 1 with HCl (2 N). Then the solution was extracted with 3×30 mL of ethyl acetate. The organic layers were combined, dried over anhydrous magnesium sulfate and concentrated under vacuum. The crude was purified by Prep-HPLC with the following conditions (2#-AnalyseHPLC-SHIMADZU(HPLC-10)): Column, XSelect CSH Prep C18 OBD Column, 19*250 mm, 5 um; Mobile Phase, Water (0.05% HCl) and ACN (35.0% ACN up to 47.0% in 15 min); Detector, UV 220/254 nm. This resulted in 11.5 mg (13%) of the title compound as a white solid. LC-MS (ESI, m/z): [M+H]+=587.2. 1HNMR (300 MHz, DMSO-d6, ppm): δ 12.90 (s, 1H), 7.95-7.93 (m, 5H), 7.69-7.59 (m, 4H), 7.58-7.52 (m, 1H), 7.26-7.20 (m, 1H), 6.96 (d, J=2.5 Hz, 1H), 6.79-6.71 (m, 1H), 4.89 (s, 2H), 3.52-3.44 (m, 2H), 2.23-2.22 (m, 1H), 1.99-1.92 (m, 1H), 1.90-1.82 (m, 1H), 1.80-1.72 (m, 1H), 1.33 (d, J=6.9 Hz, 6H).

Scheme 19 (Compound VI-01)

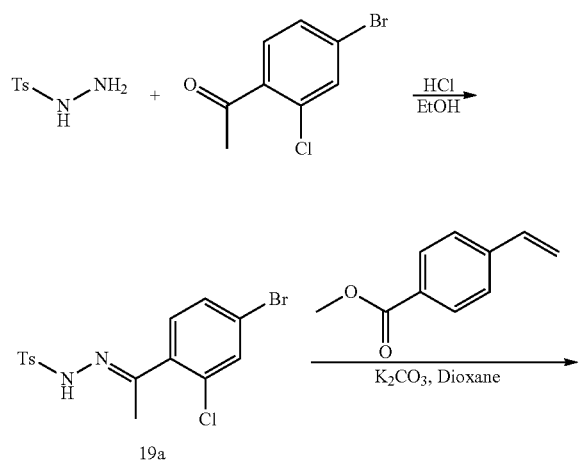

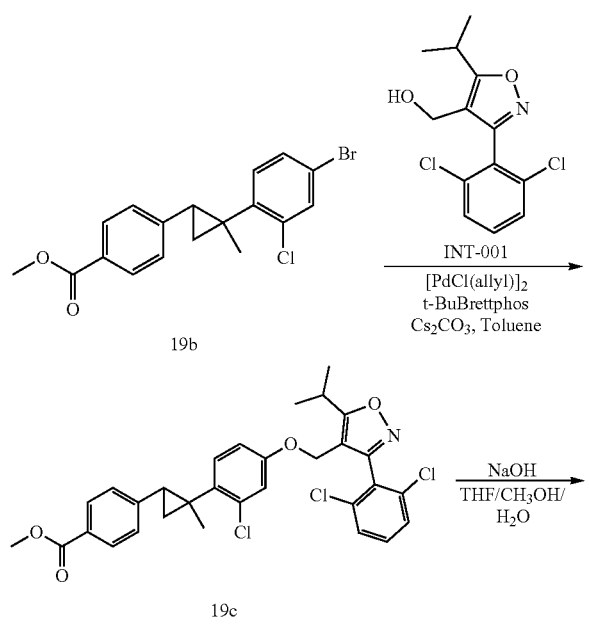

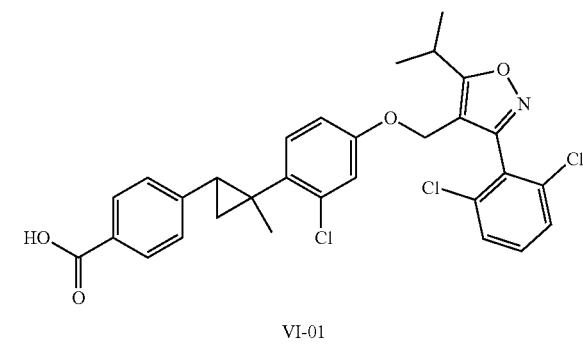

Experimental Details for Compound VI-01
(Scheme 19)

(Z)—N'-(1-(4-Bromo-2-chlorophenyl) ethylidene)-4-methylbenzenesulfonohydrazide (Compound 19a)

To a solution of 1-(4-bromo-2-chlorophenyl) ethanone (2 g, 8.62 mmol) in ethanol (30 mL) was added 4-methylbenzenesulfonohydrazide (1.7 g, 9.12 mmol) and hydrogen chloride (1.5 mL, 12N). The resulting solution was stirred for 3 h at room temperature. The solids were filtered out. The solids were applied onto a silica gel column with ethyl acetate/petroleum ether (1:15). This resulted in 2.6 g (76%) of the title compound as a white solid. LC-MS (ESI, m/z): [M+H]$^+$=403.0.

Methyl 4-(2-(4-bromo-2-chlorophenyl)-2-methylcyclopropyl) benzoate (Compound 19b)

To a solution of Compound 19a (740 mg, 1.85 mmol) in dioxane (10 mL) was added methyl 4-vinylbenzoate (900 mg, 5.55 mmol) and potassium carbonate (380 mg, 2.75 mmol). The resulting solution was stirred overnight at 100° C. The solids were filtered out. The resulting mixture was concentrated under vacuum. The residue was applied onto a silica gel column with ethyl acetate/petroleum ether (1:15). This resulted in 200 mg (29%) of the title compound as a white oil. LC-MS (ESI, m/z): [M+Na]$^+$=403.0.

Methyl 4-(2-(2-chloro-4-((3-(2,6-dichlorophenyl)-5-isopropylisoxazol-4-yl) methoxy) phenyl)-2-methylcyclopropyl) benzoate (Compound 19c)

To a mixture of Compound 19b (100 mg, 0.26 mmol) and Compound INT-001 (83.0 mg, 0.29 mmol) in toluene (3 mL) was added [PdCl(allyl)]$_2$ (4 mg, 0.012 mmol), t-BuBrettphos (13 mg, 0.03 mmol) and Cs$_2$CO$_3$ (127 mg, 0.66 mmol) under N$_2$ atmosphere. The resulting solution was stirred for 5 h at 75° C. The solids were filtered out. The resulting mixture was concentrated under vacuum. The residue was applied onto a silica gel column with ethyl acetate/petroleum ether (1:10). This resulted in 40 mg (27%) of the title compound as a white solid. LC-MS (ESI, m/z): [M+H]$^+$=584.3, 586.3.

4-(2-(2-Chloro-4-((3-(2,6-dichlorophenyl)-5-isopropylisoxazol-4-yl) methoxy) phenyl)-2-methylcyclopropyl) benzoic Acid (Compound VI-01)

To a solution Compound 19c (40 mg, 0.07 mmol) in THF/MeOH/H$_2$O (3 mL, 1:1:1) was added sodium hydroxide (14 mg, 0.35 mmol). The resulting solution was stirred for 3 h at 50° C. The pH value of the solution was adjusted to 5 with hydrogen chloride (2 N). The resulting mixture was concentrated under vacuum. The residue was applied onto a silica gel column with dichloromethane/methanol (15:1). This resulted in 7 mg (18%) of the title compound as a white solid. LC-MS (ESI, m/z): [M+H]$^+$=570.1, 572.1. $^1$HNMR (300 MHz, DMSO-d$_6$, ppm): δ 12.83 (s, 1H), 7.92 (d, J=8.4 Hz, 2H), 7.65-7.62 (m, 2H), 7.59-7.51 (m, 3H), 7.38 (d, J=8.7 Hz, 1H), 6.90 (d, J=2.4 Hz, 1H), 6.74-6.70 (m, 1H), 4.85 (s, 2H), 3.51-3.40 (m, 1H), 2.34-2.88 (m, 1H), 1.45 (t, J=6.0 Hz, 1H), 1.34 (d, J=6.9 Hz, 6H), 1.28-1.23 (m, 1H), 0.96 (s, 3H).

Scheme 20 (Compound VI-04)

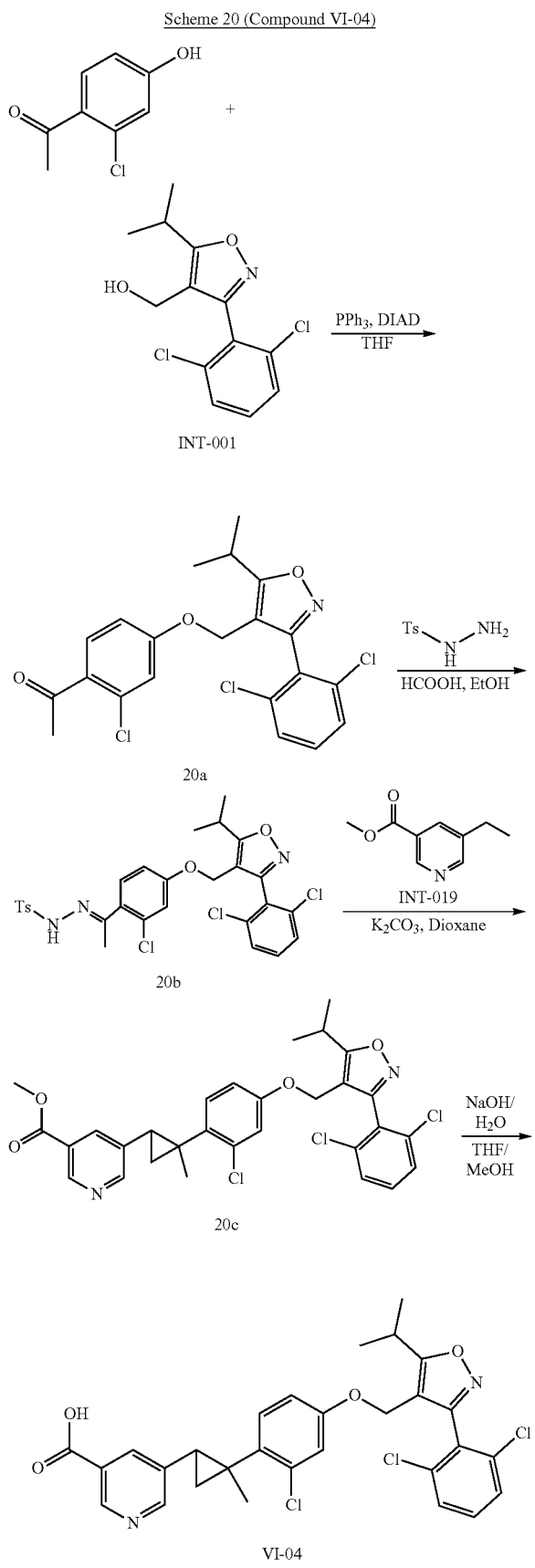

Experimental Details for Compound VI-04 (Scheme 20)

1-(2-Chloro-4-[[3-(2,6-dichlorophenyl)-5-(propan-2-yl)-1,2-oxazol-4-yl] methoxy]phenyl) ethan-1-one (Compound 20a)

To a solution of 1-(2-chloro-4-hydroxyphenyl) ethan-1-one (150 mg, 0.88 mmol), Compound INT-001 (250 mg, 0.87 mmol) and triphenylphosphane (346 mg, 1.32 mmol) in tetrahydrofuran (5 mL) was added DIAD (267 mg, 1.32 mmol) dropwise at 0° C. The resulting solution was allowed warm to room temperature and stirred for another 2 h. The resulting mixture was concentrated under vacuum. The residue was applied onto a silica gel column with ethyl acetate/petroleum ether (1:10). This resulted in 300 mg (78%) of the title compound as a white solid. LC-MS (ESI, m/z): [M+H]$^+$=438.0, 440.0.

(E)-1-(1-(4-((3-(2,6-Dichlorophenyl)-5-isopropylisoxazol-4-yl) methoxy)-2-chlorophenyl) ethylidene)-2-tosylhydrazine (Compound 20b)

To a solution of Compound 20a (300 mg, 0.68 mmol) in ethanol (5 mL) was added 4-methylbenzene-1-sulfonohydrazide (186 mg, 1.0 mmol) and formic acid (0.5 mL). The resulting solution was stirred for 0.5 h at room temperature. The resulting mixture was concentrated under vacuum. The residue was applied onto a silica gel column with ethyl acetate/petroleum ether (1:5). This resulted in 400 mg (96%) of the title compound as a white solid. LC-MS (ESI, m/z): [M+H]$^+$=606.0, 608.0.

Methyl 5-[2-(2-chloro-4-[[3-(2,6-dichlorophenyl)-5-(propan-2-yl)-1,2-oxazol-4-yl]methoxy] phenyl)-2-methylcyclopropyl] pyridine-3-carboxylate (Compound 20c)

To a solution of Compound 20b (150 mg, 0.25 mmol) and Compound INT-019 (834 mg, 5.11 mmol) in dioxane (5 mL) was added potassium carbonate (380 mg, 2.75 mmol). The resulting solution was stirred for 3 h at 100° C. The solids were filtered out. The resulting mixture was concentrated under vacuum. The residue was applied onto a silica gel column with ethyl acetate/petroleum ether (1:5). This resulted in 100 mg (69%) of the title compound as a white solid. LC-MS (ESI, m/z): [M+H]$^+$=585.2, 587.1.

5-[2-(2-Chloro-4-[[3-(2,6-dichlorophenyl)-5-(propan-2-yl)-1,2-oxazol-4-yl]methoxy] phenyl)-2-methylcyclopropyl] pyridine-3-carboxylic Acid (Compound VI-04)

To a solution of Compound 20c (60 mg, 0.10 mmol) in a mixed solvent of tetrahydrofuran and methanol (2 mL, 1:1) was added a solution of sodium hydroxide (20 mg, 0.50 mmol) in water (1 mL). The resulting solution was stirred for 1 h at 50° C. The pH value of the solution was adjusted to 3 with hydrogen chloride (2 N). The resulting mixture was concentrated under vacuum. The residue was applied onto a silica gel column with dichloromethane/methanol (15:1). This resulted in 10 mg (17%) of the title compound as a white solid. LC-MS (ESI, m/z): [M+H]$^+$=571.3. $^1$HNMR (300 MHz, DMSO-d$_6$, ppm): δ 8.93 (s, 1H), 8.76 (s, 1H), 8.18 (s, 1H), 7.64-7.53 (m, 3H), 7.41 (d, J=8.4 Hz, 1H), 6.90

(s, 1H), 6.74 (d, J=7.2 Hz, 1H), 4.85 (s, 2H), 3.48-3.43 (m, 1H), 2.39-2.33 (m, 1H), 1.48-1.46 (m, 1H), 1.35-1.24 (m, 7H), 0.97 (s, 3H).

Scheme 21 (Compound VI-12)

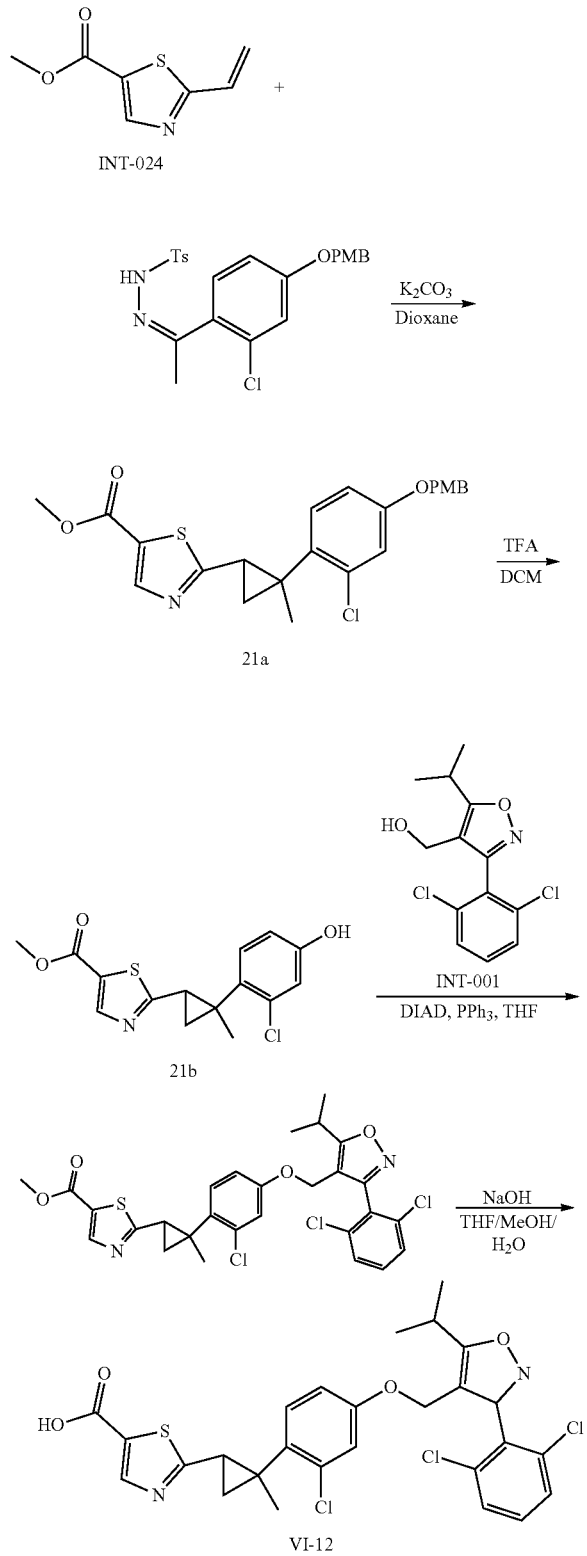

Experimental Details for Compound VI-12
(Scheme 21)

Methyl 2-(2-(2-chloro-4-(4-methoxybenzyloxy) phenyl)-2-methylcyclopropyl) thiazole-5-carboxylate (Compound 21a)

To a solution of Compound INT-024 (150 mg, 0.89 mmol) in dioxane (3 mL) was added (Z)—N'-(1-(2-chloro-4-(4-methoxybenzyloxy) phenyl) ethylidene)-4-methylbenzenesulfonohydrazide and potassium carbonate (243 mg, 1.75 mmol). The resulting solution was stirred for 4 h at 100° C. The solids were filtered out. The resulting mixture was concentrated under vacuum. The residue was applied onto a silica gel column with ethyl acetate/petroleum ether (12:88). This resulted in 300 mg (76%) of the title compound as a white solid. LC-MS (ESI, m/z): [M+H]$^+$=444.1.

Methyl 2-(2-(2-chloro-4-hydroxyphenyl)-2-methylcyclopropyl) thiazole-5-carboxylate (Compound 21b)

To a solution of Compound 21a (300 mg, 0.68 mmol) in dichloromethane (10 mL) was added trifluoroacetic acid (1 mL). The resulting solution was stirred for 0.5 h at room temperature. The resulting mixture was concentrated under vacuum. The residue was applied onto a silica gel column with ethyl acetate/petroleum ether (17:83). This resulted in 100 mg (46%) of the title compound as a white solid. LC-MS (ESI, m/z): [M+H]$^+$=324.0.

Methyl 2-(2-(2-chloro-4-((3-(2,6-dichlorophenyl)-5-isopropylisoxazol-4-yl) methoxy) phenyl)-2-methylcyclopropyl) thiazole-5-carboxylate (Compound 21c)

To a solution of Compound 21b (100 mg, 0.31 mmol), Compound INT-001 (88.2 mg, 0.31 mmol) and triphenylphosphane (97 mg, 0.37 mmol) in THF (3 mL) was added DIAD (75 mg, 0.57 mmol) dropwise at 0° C. The resulting solution was stirred for 2 h at room temperature. The resulting mixture was concentrated under vacuum. The residue was applied onto a silica gel column with ethyl acetate/petroleum ether (19:81). This resulted in 100 mg (55%) of the title compound as a white solid. LC-MS (ESI, m/z): [M+H]$^+$=593.0.

2-(2-(2-Chloro-4-((3-(2,6-dichlorophenyl)-5-isopropylisoxazol-4-yl) methoxy) phenyl)-2-methylcyclopropyl) thiazole-5-carboxylic Acid (Compound VI-12)

To a solution of Compound 21c (100 mg, 0.17 mmol) in a mixed solvent of THF/MeOH/H$_2$O (4 mL, 2:1:1) was added sodium hydroxide (34 mg, 0.85 mmol). The resulting solution was stirred for 3 h at 50° C. The pH value of the solution was adjusted to 6 with hydrogen chloride (2 N). The resulting mixture was concentrated under vacuum. The residue was filtered out. The residue was applied onto a C18 column with CH$_3$CN/Water (34:66). This resulted in 30.4 mg (31%) of the title compound as a white solid. LC-MS (ESI, m/z): [M+H]$^+$=577.1. $^1$HNMR (300 MHz, DMSO-d$_6$, ppm): δ 8.16 (s, 1H), 7.64-7.61 (s, 2H), 7.57-7.52 (m, 1H), 7.30-7.27 (d, J=8.5 Hz, 1H), 6.91-6.90 (d, J=2.6 Hz, 1H), 6.74-6.70 (m, 1H), 4.84 (s, 2H), 3.49-3.40 (m, 1H), 2.60-2.53 (m, 1H), 1.68-1.64 (m, 1H), 1.56-1.51 (m, 1H), 1.34-1.31 (d, J=7.0 Hz, 6H), 1.14 (s, 3H).

Following the procedure described above for Scheme 19-21 and substituting the appropriate reagents, starting materials and purification methods known to those skilled in the art, the following compounds of the present invention were prepared.

TABLE 6

| Compound | Structure | Scheme | LC-MS (M + H)+ | ¹HNMR (ppm) |
|---|---|---|---|---|
| VI-02 | 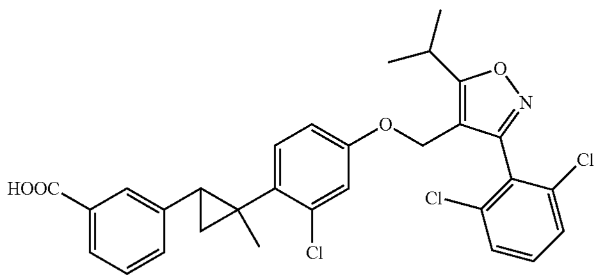 [SMILES: CC(C)c1onc(-c2c(Cl)cccc2Cl)c1COc1ccc(C2(C)CC2c2cccc(C(=O)O)c2)c(Cl)c1] | 19 | 572.1 | DMSO-d$_6$: δ 7.94 (s, 1H), 7.82-7.80 (m, 1H), 7.65-7.62 (m, 4H), 7.56-7.54 (m, 1H), 7.47-7.45 (m, 1H), 7.43-7.36 (m, 1H), 6.75-6.72 (m, 1H), 4.85 (s, 2H), 3.45-3.43 (m, 1H), 2.34-2.30 (m, 1H), 1.43-1.32 (m, 8H), 0.95 (s, 3H). |
| VI-03 | 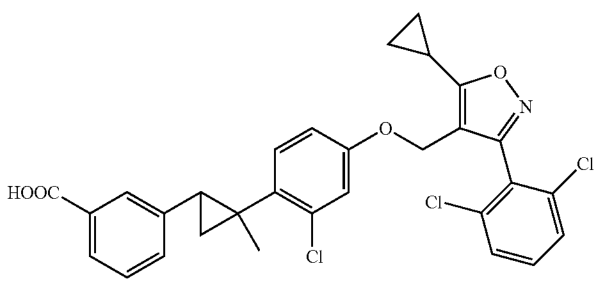 [SMILES: CC1(c2ccc(OCc3c(-c4c(Cl)cccc4Cl)noc3C3CC3)cc2Cl)CC1c1cccc(C(=O)O)c1] | 20 | 568.3, 570.3 | DMSO-d$_6$: δ 7.95 (s, 1H), 7.80-7.76 (m, 1H), 7.61-7.50 (m, 4H), 7.42-7.30 (m, 2H), 6.90 (s, 1H), 6.80-6.70 (m, 1H), 4.89 (s, 2H), 2.45-2.40 (m, 1H), 1.32-1.25 (m, 1H), 1.40-1.20 (m, 2H), 1.20-1.10 (m, 4H), 0.95 (s, 3H). |
| VI-05 | 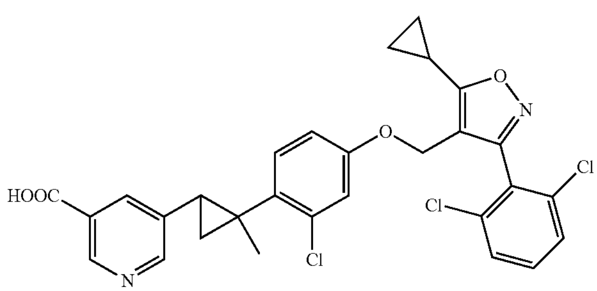 [SMILES: CC1(c2ccc(OCc3c(-c4c(Cl)cccc4Cl)noc3C3CC3)cc2Cl)CC1c1cncc(C(=O)O)c1] | 20 | 569.1, 571.1 | DMSO-d$_6$: δ 8.92 (s, 1H), 8.76 (s, 1H), 8.16 (s, 1H), 7.63-7.53 (m, 3H), 7.40-7.36 (m, 1H), 6.91-6.89 (m, 1H), 6.78-6.72 (m, 1H), 4.90 (s, 2H), 2.45-2.40 (m, 1H), 2.35-2.25 (m, 1H), 1.51-1.42 (m, 1H), 1.38-1.31 (m, 1H), 1.20-1.10 (m, 4H), 0.96 (s, 3H). |
| VI-06 | 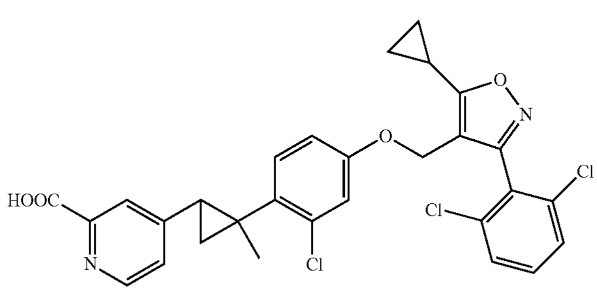 [SMILES: CC1(c2ccc(OCc3c(-c4c(Cl)cccc4Cl)noc3C3CC3)cc2Cl)CC1c1ccnc(C(=O)O)c1] | 21 | 570.6 | DMSO-d$_6$: δ 8.63-8.62 (m, 1H), 8.06 (s, 1H), 7.64-7.62 (m, 3H), 7.57-7.53 (m, 1H), 7.39-7.37 (d, J = 8.6 Hz, 1H), 6.93-6.92 (m, 1H), 6.77-6.74 (m, 1H), 4.91 (s, 2H), 2.49-2.33 (m, 2H), 1.61-1.58 (m, 1H), 1.42-1.38 (m, 1H), 1.24-1.09 (m, 4H), 1.00 (s, 3H). |

TABLE 6-continued

| Compound | Structure | Scheme | LC-MS (M + H)+ | ¹HNMR (ppm) |
|---|---|---|---|---|
| VI-07 | 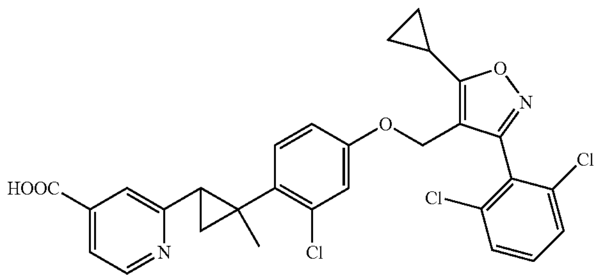 [SMILES: CC1(c2ccc(OCc3c(-c4c(Cl)cccc4Cl)noc3C3CC3)cc2Cl)CC1c1cc(C(=O)O)ccn1] | 19 | 571.3 | DMSO-d₆: δ 8.70 (d, J = 5.1 Hz, 1H), 7.98-7.97 (m, 1H), 7.64-7.61 (m, 3H), 7.57-7.55 (m, 1H), 7.38-7.36 (m, 1H), 6.91-6.90 (m, 1H), 6.76-6.73 (m, 1H), 4.90 (s, 2H), 2.51-2.50 (m, 2H), 1.76-1.73 (m, 1H), 1.34-1.31 (m, 1H), 1.20-1.18 (m, 1H), 1.80-1.50 (m, 3H), 1.45-1.20 (m, 3H). |
| VI-08 | 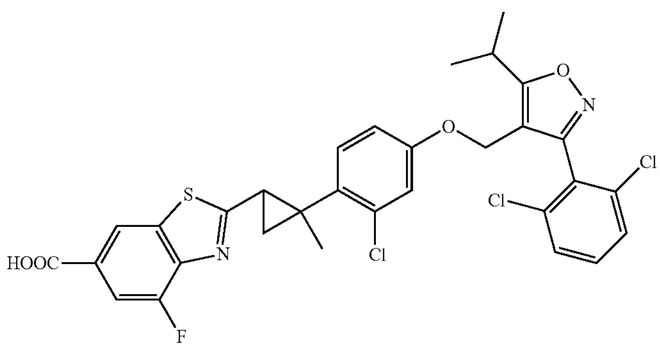 [SMILES: CC(C)c1onc(-c2c(Cl)cccc2Cl)c1COc1ccc(C2(C)CC2c2nc3c(F)cc(C(=O)O)cc3s2)c(Cl)c1] | 20 | 645.1 | DMSO-d₆: δ 8.56 (s, 1H), 7.88-7.85 (m, 1H), 7.37-7.35 (m, 2H), 7.32-7.27 (m, 2H), 6.82-6.81 (m, 1H), 6.68-6.66 (m, 1H), 4.82-4.73 (m, 2H), 3.30-3.28 (m, 1H), 2.65-2.63 (m, 1H), 2.04-2.02 (m, 1H), 1.99-1.79 (m, 1H), 1.68-1.61 (m, 6H), 1.45 (s, 3H). |
| VI-09 | 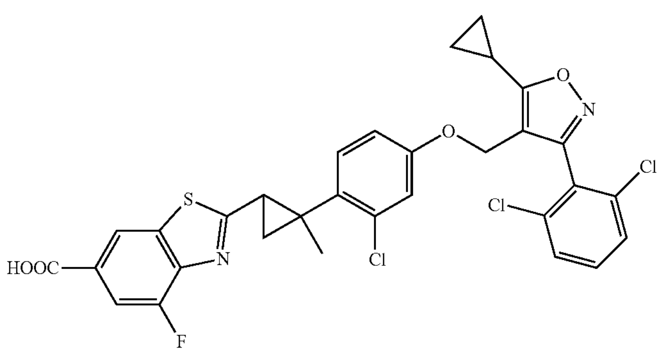 [SMILES: CC1(c2ccc(OCc3c(-c4c(Cl)cccc4Cl)noc3C3CC3)cc2Cl)CC1c1nc2c(F)cc(C(=O)O)cc2s1] | 19 | 645.3 | DMSO-d₆: δ 8.56 (d, J = 1.2 Hz, 1H), 7.82-7.80 (m, 1H), 7.64-7.63 (m, 2H), 7.62-7.61 (m, 1H), 7.36-7.34 (m, 1H), 6.96-6.95 (m, 1H), 6.78-6.75 (m, 1H), 4.92 (s, 2H), 2.82-2.79 (m, 1H), 2.50-2.45 (m, 1H), 1.86-1.81 (m, 1H), 1.67-1.63 (m, 1H), 1.24-1.20 (m, 3H), 1.18-1.15 (m, 2H), 1.15-1.15 (m, 2H). |
| VI-10 | 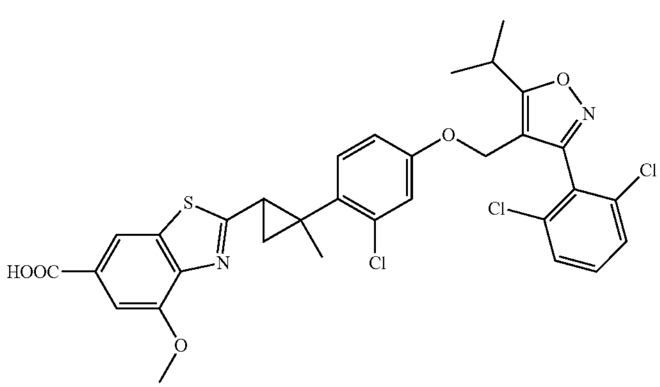 [SMILES: COc1cc(C(=O)O)cc2sc(C3CC3(C)c3ccc(OCc4c(-c5c(Cl)cccc5Cl)noc4C(C)C)cc3Cl)nc12] | 20 | 657.1 | DMSO-d₆: 8.22 (s, 1H), 7.61-7.40 (m, 5H), 6.70 (s, 2H), 4.82 (s, 2H), 3.84 (s, 3H), 3.28-3.21 (m, 1H), 2.95-2.91 (m, 1H), 1.70 (m, 1H), 1.61 (m, 1H), 1.49 (s, 3H), 1.34-1.23 (m, 6H). |

TABLE 6-continued
| Compound | Structure | Scheme | LC-MS (M + H)+ | 1HNMR (ppm) |
|---|---|---|---|---|
| VI-11 | 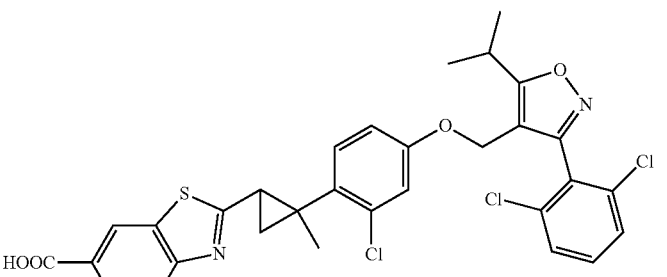 | 20 | 627.1 | DMSO-d6: δ 8.64 (m, 1H), 8.03-8.01 (m, 2H), 7.65-7.64 (m, 2H), 7.64-7.62 (m, 1H), 7.58-7.56 (m, 1H), 6.94-6.93 (m, 1H), 6.76-6.74 (m, 1H), 4.86 (s, 2H), 3.49-3.48 (m, 1H), 2.73-2.72 (m, 1H), 1.83-1.82 (m, 1H), 1.65-1.64 (m, 1H), 1.35-1.33 (m, 6H), 1.23 (s, 3H). |
| VI-13 | 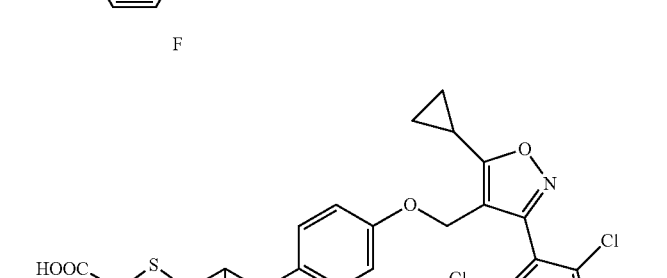 | 21 | 575.0 | DMSO-d6: δ 8.1 (s, 1H), 7.64-7.62 (m, 2H), 7.58-7.53 (m, 1H), 7.31-7.29 (m, 1H), 6.93-6.92 (d, J = 2.6 Hz, 1H), 6.77-6.74 (m, 1H), 4.90 (s, 2H), 2.58-2.55 (m, 1H), 2.47-2.42 (m, 1H), 1.67-1.64 (m, 1H), 1.55-1.51 (m, 1H), 1.21-1.11 (m, 7H). |
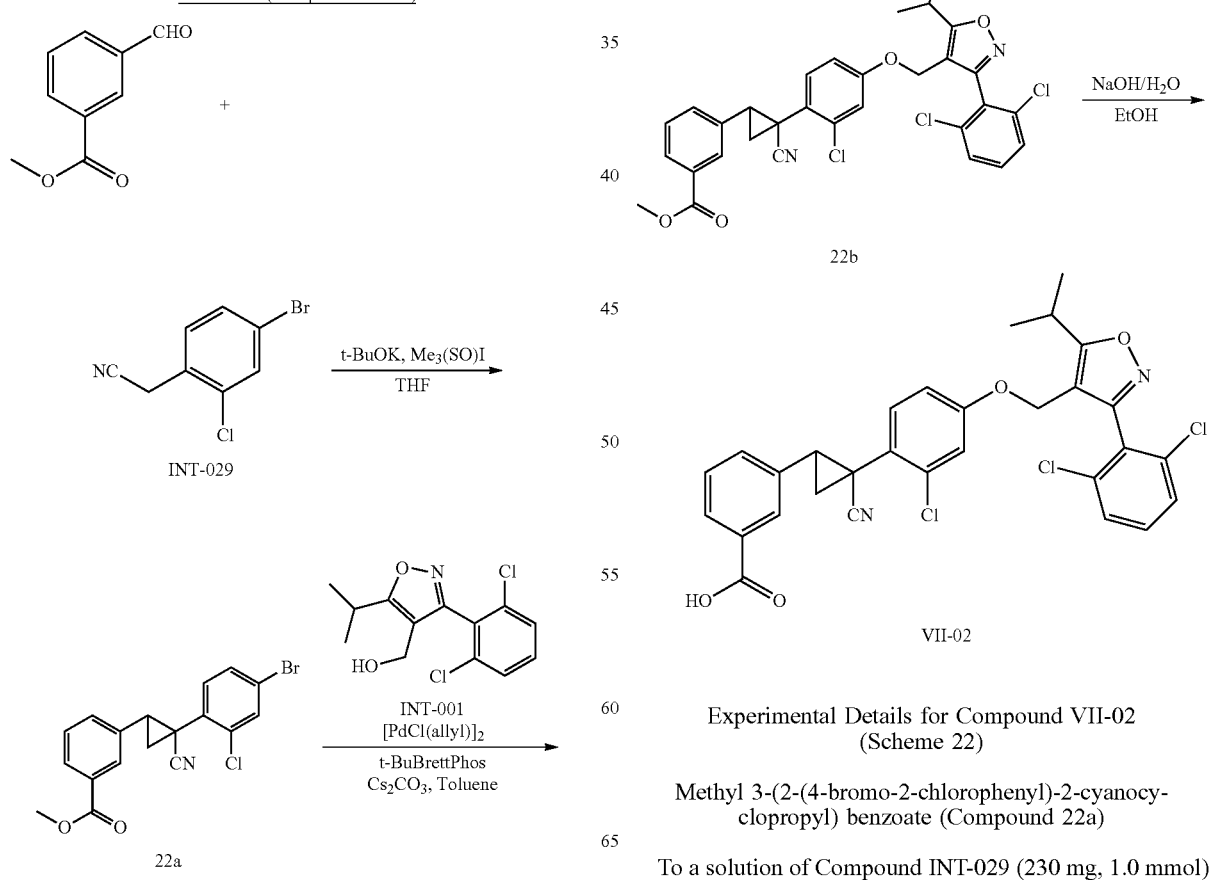
Experimental Details for Compound VII-02 (Scheme 22)
Methyl 3-(2-(4-bromo-2-chlorophenyl)-2-cyanocyclopropyl) benzoate (Compound 22a)
To a solution of Compound INT-029 (230 mg, 1.0 mmol) and methyl 3-formylbenzoate (180 mg, 1.10 mmol) in THF (10 mL) was added t-BuOK (146 mg, 1.30 mmol) at −30° C. After stirring for 0.5 h at room temperature, S, S-dimethylmethanesulfinyl iodide (330 mg, 1.50 mmol) was added one portion at −30° C. The resulting solution was stirred for 5 h at room temperature. The reaction was quenched by the addition of 50 mL of HCl (1 N). The resulted mixture was extracted with 3×50 mL of ethyl acetate. The organic layers were combined, dried over anhydrous magnesium sulfate and concentrated under vacuum. The residue was applied onto a silica gel column with ethyl acetate/hexane (1:8). The collected fractions were combined and concentrated under vacuum. This resulted in 203 mg (50%) of the title compound as a white solid. LC-MS (ESI, m/z): [M+Na+MeCN]$^+$=455.2.

Methyl 3-[2-(2-chloro-4-[[3-(2,6-dichlorophenyl)-5-(propan-2-yl)-1,2-oxazol-4-yl]methoxy] phenyl)-2-cyanocyclopropyl] benzoate (Compound 22b)

To a solution of Compound 22a (86 mg, 0.22 mmol) and Compound INT-001 (57 mg, 0.20 mmol) in toluene (3 mL) was added cesium carbonate (130 mg, 0.40 mmol), tBu-brettPhos (9 mg, 0.02 mmol), [PdCl(allyl)]$_2$ (3 mg, 0.008 mmol). The resulting solution was stirred for 3.5 h at 75° C. under N$_2$ atmosphere. The reaction was then quenched by the addition of 30 mL of water. The resulted mixture was extracted with 3×30 mL of ethyl acetate. The organic layers were combined, dried over anhydrous magnesium sulfate and concentrated under vacuum. The residue was applied onto a silica gel column with ethyl acetate/hexane (1:8). The collected fractions were combined and concentrated under vacuum. This resulted in 42 mg (35%) of the title compound as a white solid.

3-[2-(2-Chloro-4-[[3-(2,6-dichlorophenyl)-5-(propan-2-yl)-1,2-oxazol-4-yl]methoxy] phenyl)-2-cyanocyclopropyl] benzoic Acid (Compound VII-02)

To a solution of Compound 22b (42 mg, 0.07 mmol) in ethanol (4 mL) was added a solution of sodium hydroxide (10 mg, 0.25 mmol) in water (2 mL). The mixture was stirred for 2 h at 50° C. The pH value of the solution was adjusted to 1 with HCl (2 N). The resulting mixture was extracted with 3×30 mL of ethyl acetate. The organic layers were combined, dried over anhydrous magnesium sulfate and concentrated under vacuum. The crude was purified by Prep-HPLC with the following conditions (2#-AnalyseHPLC-SHIMADZU(HPLC-10)): Column, XSelect CSH Prep C18 OBD Column, 19*250 mm, 5 um; Mobile Phase, Water (0.05% HCl) and ACN (50.0% ACN up to 78.0% in 15 min); Detector, UV 254/220 nm. This resulted in 4.6 mg (11%) of the title compound as a white solid. LC-MS (ESI, m/z): [M+H]$^+$=581.0. $^1$HNMR (300 MHz, DMSO-d$_6$, ppm): δ 12.97 (s, 1H), 8.05-8.04 (m, 1H), 7.92-7.89 (m, 1H), 7.78-7.75 (m, 1H), 7.73-7.70 (m, 2H), 7.68-7.44 (m, 3H), 7.07-7.04 (m, 1H), 6.80-6.77 (m, 1H), 4.91 (s, 2H), 3.49-3.42 (m, 1H), 2.92-2.89 (m, 1H), 2.50-2.43 (m, 1H), 2.00-1.97 (m, 1H), 1.34 (d, J=7.2 Hz, 6H).

Scheme 23 (Compound VII-03)

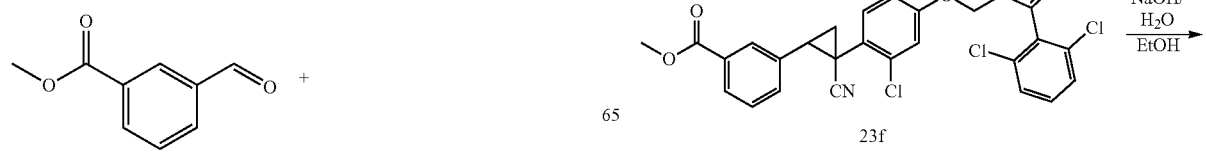

-continued

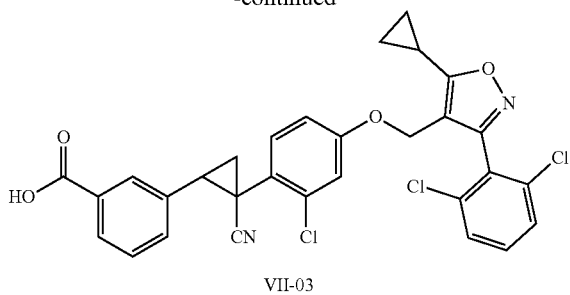

VII-03

Experimental Details for Compound VII-03 (Scheme 23)

(2Z)-2-(4-Bromo-2-chlorophenyl)-3-[3-(methoxycarbonyl) phenyl] prop-2-enoic Acid (Compound 23a)

To a solution of 2-(4-bromo-2-chlorophenyl) acetic acid (1.5 g, 6.01 mmol) and methyl 3-formylbenzoate (1 g, 6.09 mmol) in acetyl acetate (15 mL) was added triethylamine (2 g, 19.8 mmol). The resulting solution was stirred for 16 h at 120° C. The mixture was concentrated under vacuum. The residue was diluted with ethyl acetate, washed with water and brine, then dried over anhydrous sodium sulfate, and concentrated under vacuum. The residue was applied onto a silica gel column with ethyl acetate/petroleum ether (1:2). The collected fractions were combined and concentrated under vacuum. This resulted in 1.8 g (76%) of the title compound as a solid. LC-MS (ESI, m/z): [M+H]$^+$=395.0.

Methyl 3-[(1Z)-2-(4-bromo-2-chlorophenyl)-2-carbamoyleth-1-en-1-yl] benzoate (Compound 23b)

To a solution of Compound 23a (1.8 g, 4.55 mmol) in DMA (30 mL) was added CDI (1.6 g, 9.87 mmol) batchwise at 0° C. The mixture was stirred for 1.5 h at room temperature. Then ammonia (2 mL, 25% w/w) was added one portion. The resulting mixture was stirred for another 2 h at room temperature. The resulting solution was diluted with 3×100 mL of ethyl acetate. The organic layers were combined and washed with water and brine, then dried over anhydrous sodium sulfate, and concentrated under vacuum. The residue was applied onto a silica gel column with ethyl acetate/petroleum ether (1:1). The collected fractions were combined and concentrated under vacuum. This resulted in 1.7 g (95%) of the title compound as a solid. LC-MS (ESI, m/z): [M+H]$^+$=396.1.

Methyl 3-[(1Z)-2-(4-bromo-2-chlorophenyl)-2-cyanoeth-1-en-1-yl] benzoate (Compound 23c)

Compound 23b (1.7 g, 4.31 mmol) was added batchwise into a precooled solvent of POCl$_3$ (5 mL) at 0° C. Then a drop of DMF was added into above mixture. The resulting solution was stirred for 2 h at 0° C. The reaction was then quenched by the addition of 100 g of water/ice after the solvent was removed under vacuum. The resulting mixture was extracted with 3×100 mL of ethyl acetate. The organic layers were combined and washed with water and brine, then dried over anhydrous magnesium sulfate, and concentrated under vacuum. The residue was applied onto a silica gel column with ethyl acetate/petroleum ether (1:2). The collected fractions were combined and concentrated under vacuum. This resulted in 1.4 g (86%) of the title compound as a solid. LC-MS (ESI, m/z): [M+Na+MeCN]$^+$=440.9.

3-[2-(4-Bromo-2-chlorophenyl)-2-cyanocyclopropyl] benzoic Acid (Compound 23d)

To a solution of Compound 23c (1.4 g, 3.72 mmol,) and S, S-dimethylmethanesulfinyl iodide (1.5 g, 6.82 mmol) in DMSO (10 mL) was added sodium hydride (300 mg, 7.50 mmol) batchwise. The resulting mixture was stirred for 16 h at room temperature. The reaction was then quenched by the addition of 50 mL of water/ice. The pH value of the solution was adjusted to 2 with hydrogen chloride (2 N). The resulting mixture was extracted with 3×75 mL of ethyl acetate. The organic layers were combined and washed with water and brine, then dried over anhydrous magnesium sulfate, and concentrated under vacuum. The residue was applied onto a silica gel column with ethyl acetate/petroleum ether (1:1). The collected fractions were combined and concentrated under vacuum. This resulted in 0.8 g (57%) of the title compound as a solid.

Methyl 3-[2-(4-bromo-2-chlorophenyl)-2-cyanocyclopropyl] benzoate (Compound 23e)

To a solution of Compound 23d (800 mg, 2.12 mmol), iodomethane (450 mg, 3.17 mmol) in DMF (20 mL) was added potassium carbonate (600 mg, 4.31 mmol). The resulting mixture was stirred for 2 h at room temperature. The resulting mixture was diluted with water and extracted with 3×75 mL of ethyl acetate. The organic layers were combined and washed with water and brine, then dried over anhydrous magnesium sulfate, and concentrated under vacuum. The residue was applied onto a silica gel column with ethyl acetate/petroleum ether (1:2). The collected fractions were combined and concentrated under vacuum. This resulted in 0.8 g (96%) of the title compound as a solid. LC-MS (ES, m/z): [M+Na+MeCN]$^+$=455.1

Methyl 3-[2-(2-chloro-4-[[5-cyclopropyl-3-(2,6-dichlorophenyl)-1,2-oxazol-4-yl]methoxy] phenyl)-2-cyanocyclopropyl] benzoate (Compound 23f)

To a solution of Compound 23e (800 mg, 2.05 mmol) and Compound INT-003 (630 mg, 2.22 mmol) in toluene (12 mL) was added cesium carbonate (1.3 g, 3.98 mmol), RockPhos (94 mg, 0.19 mmol) and [PdCl(allyl)]$_2$ (15 mg, 0.04 mmol). The resulting solution was stirred for 2 h at 80° C. under N$_2$ atmosphere. The resulting mixture was concentrated under vacuum. The residue was applied onto a silica gel column with ethyl acetate/petroleum ether (1:2). The collected fractions were combined and concentrated under vacuum. This resulted in 0.8 g (66%) of the title compound as a solid. LC-MS (ES, m/z): [M+H]$^+$=595.3.

3-[2-(2-Chloro-4-[[5-cyclopropyl-3-(2,6-dichlorophenyl)-1,2-oxazol-4-yl]methoxy] phenyl)-2-cyanocyclopropyl] benzoic Acid (Compound VII-03)

To a solution of Compound 23f (900 mg, 1.52 mmol) in ethanol (20 mL) was added a solution of sodium hydroxide (200 mg, 5.0 mmol) in water (10 mL). The mixture was stirred for 2 h at 50° C. The pH value of the mixture was adjusted the pH value to 1 with HCl (2 N). The resulting mixture was extracted with 3×30 mL of ethyl acetate. The organic layers were combined, dried over anhydrous magnesium sulfate and concentrated under vacuum. The crude was purified by Prep-HPLC with the following conditions (2#-AnalyseHPLC-SHIMADZU(HPLC-10)): Column, XSelect CSH Prep C18 OBD Column, 19*250 mm, 5 um; Mobile Phase, Water (0.05% HCl) and ACN (70.0% ACN up to 87.0% in 7 min); Detector, UV 254/220 nm. This resulted in 800 mg (91%) of the title compound as a white solid. LC-MS (ESI, m/z): [M+H]$^+$=581.2. $^1$HNMR (300 MHz, DMSO-$d_6$, ppm): δ 13.05 (s, 1H), 8.05-8.04 (m, 1H), 7.92-7.89 (m, 1H), 7.73-7.71 (m, 1H), 7.71-7.60 (m, 2H), 7.57-7.49 (m, 3H), 7.06-7.05 (m, 1H), 6.84-6.82 (m, 1H), 4.96 (s, 2H), 2.93-2.91 (m, 1H), 2.50-2.47 (m, 2H), 2.02-1.96 (m, 1H), 1.21-1.15 (m, 4H).

Scheme 24 (Compound VII-05)

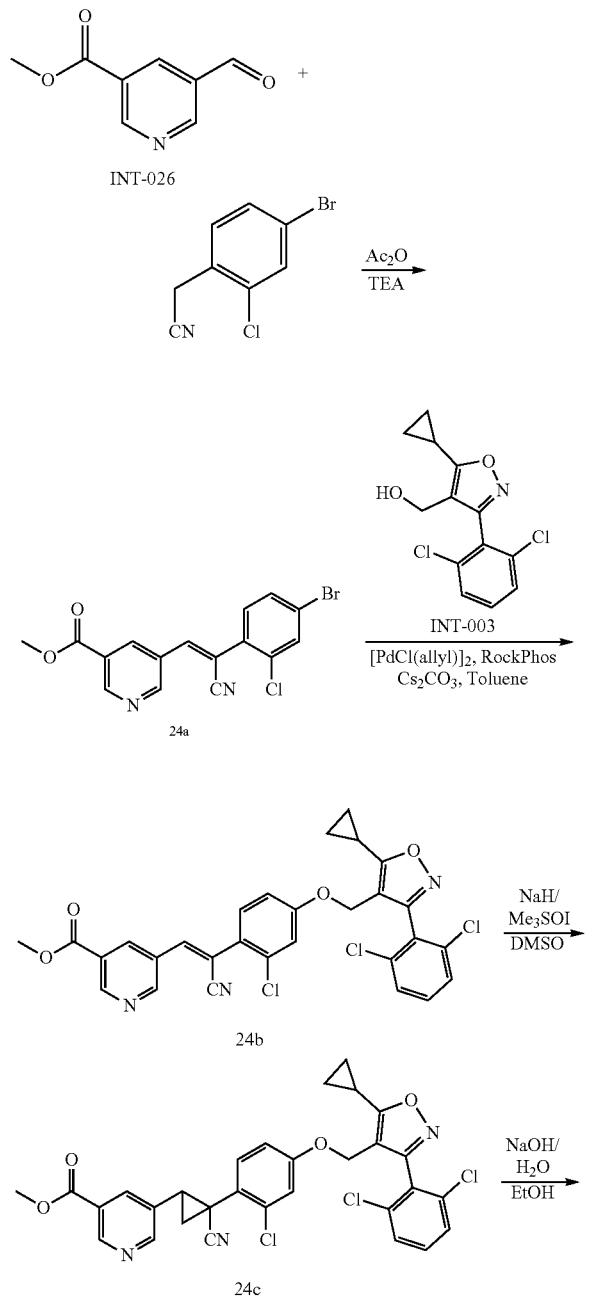

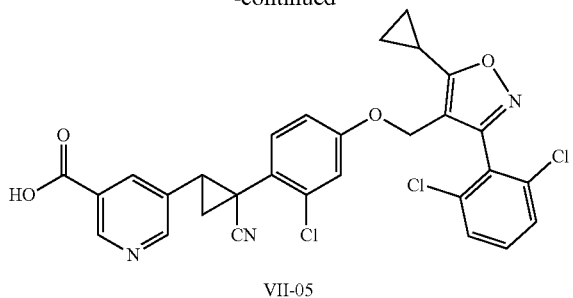

VII-05

Experimental Details for Compound VII-05
(Scheme 24)

Methyl 5-((Z)-2-(4-bromo-2-chlorophenyl)-2-cyanovinyl) pyridine-3-carboxylate (Compound 24a)

To a solution of Compound INT-026 (300 mg, 1.82 mmol), 2-(4-bromo-2-chlorophenyl) acetonitrile (500 mg, 2.18 mmol) in acetyl acetate (8 mL) was added triethylamine (1 mL, 7.23 mmol). The reaction was stirred for 16 h at 80° C. The mixture was concentrated under vacuum. The residue was applied onto a silica gel column with ethyl acetate/petroleum ether (1:1). This resulted in 450 mg (78%) of the title compound as a solid. LC-MS (ESI, m/z): [M+H+MeCN]$^+$=420.2.

Methyl 5-((Z)-2-(4-((3-(2,6-dichlorophenyl)-5-cyclopropylisoxazol-4-yl) methoxy)-2-chlorophenyl)-2-cyanovinyl) pyridine-3-carboxylate (Compound 24b)

To a solution of Compound 24a (120 mg, 0.31 mmol) and Compound INT-003 (90 mg, 0.32 mmol) in toluene (3 mL) was added Cs$_2$CO$_3$ (200 mg, 0.61 mmol), Rockphos (13 mg, 0.03 mmol), [PdCl(allyl)]$_2$ (4 mg, 0.01 mmol). The reaction was stirred for 4 h at 80° C. under N$_2$ atmosphere. The filtrate was concentrated under vacuum after filtration. The residue was applied onto a silica gel column with ethyl acetate/petroleum ether (1:1) This resulted in 110 mg (61%) of the title compound as a solid. LC-MS (ESI, m/z): [M+H]$^+$= 582.3.

Methyl 5-(2-(4-((3-(2,6-dichlorophenyl)-5-cyclopropylisoxazol-4-yl) methoxy)-2-chlorophenyl)-2-cyanocyclopropyl) pyridine-3-carboxylate (Compound 24c)

To a solution of S, S-dimethylmethanesulfinyl iodide (100 mg, 0.45 mmol) in DMSO (3 mL) was added sodium hydride (20 mg, 0.50 mmol) batchwise at room temperature. The mixture was stirred for another 1 h at this temperature then a solution of Compound 24b (110 mg, 0.19 mmol) in DMSO (2 mL) was added dropwise at room temperature. The reaction was stirred for another 4 h at room temperature. The reaction was quenched by the addition of 30 mL of water. The resulted mixture was extracted with ethyl acetate several times. The organic layers were combined and washed with water and brine, then dried over anhydrous magnesium sulfate, and concentrated under vacuum. The residue was applied onto a silica gel column with ethyl acetate/petroleum ether (1:2) This resulted in 60 mg (54%) of the title compound as a solid.

5-(2-(4-((3-(2,6-Dichlorophenyl)-5-cyclopropylisoxazol-4-yl) methoxy)-2-chlorophenyl)-2-cyanocyclopropyl) pyridine-3-carboxylic Acid (Compound VII-05)

To a solution of Compound 24c (60 mg, 0.10 mmol) in ethanol (3 mL) was added a solution of sodium hydroxide (10 mg, 0.25 mmol) in water (1 mL). The reaction was stirred for 2 h at 50° C. The pH value of the mixture was adjusted to 1 with HCl (2 N). The mixture was concentrated under vacuum. The crude product was purified by Prep-HPLC with the following conditions (2#-AnalyseHPLC-SHIMADZU(HPLC-10)): Column, XSelect CSH Prep C18 OBD Column, 5 um, 19*150 mm; Mobile Phase, Water (10 mmol/L $NH_4HCO_3$) and ACN (20.0% ACN up to 50.0% in 10 min); Detector, UV 220/254 nm. This resulted in 5.5 mg (8%) of the title compound as a solid. LC-MS (ESI, m/z): $[M+H]^+=582.2$. $^1$HNMR (400 MHz, DMSO-$d_6$, ppm): δ 8.97 (s, 1H), 8.72 (s, 1H), 8.22-8.21 (m, 1H), 7.63-7.61 (m, 2H), 7.58-7.51 (m, 2H), 7.07-7.06 (m, 1H), 6.84-6.83 (m, 1H), 4.96 (s, 2H), 2.92-2.89 (m, 1H), 2.50-2.49 (m, 2H), 2.01-1.99 (m, 1H), 1.21-1.19 (m, 2H), 1.17-1.15 (m, 2H).

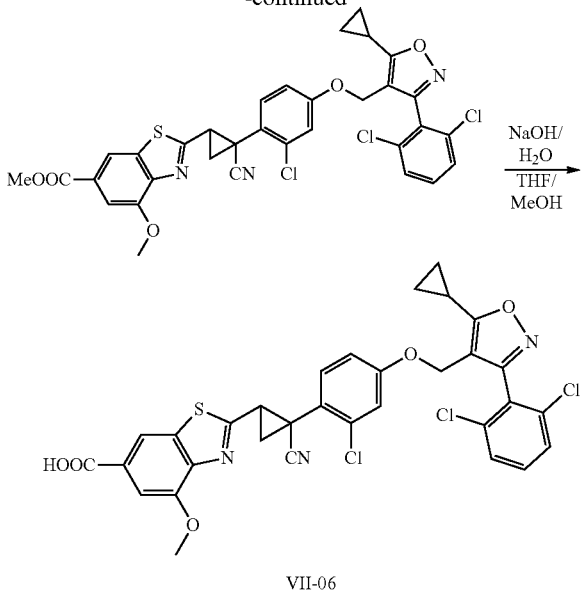

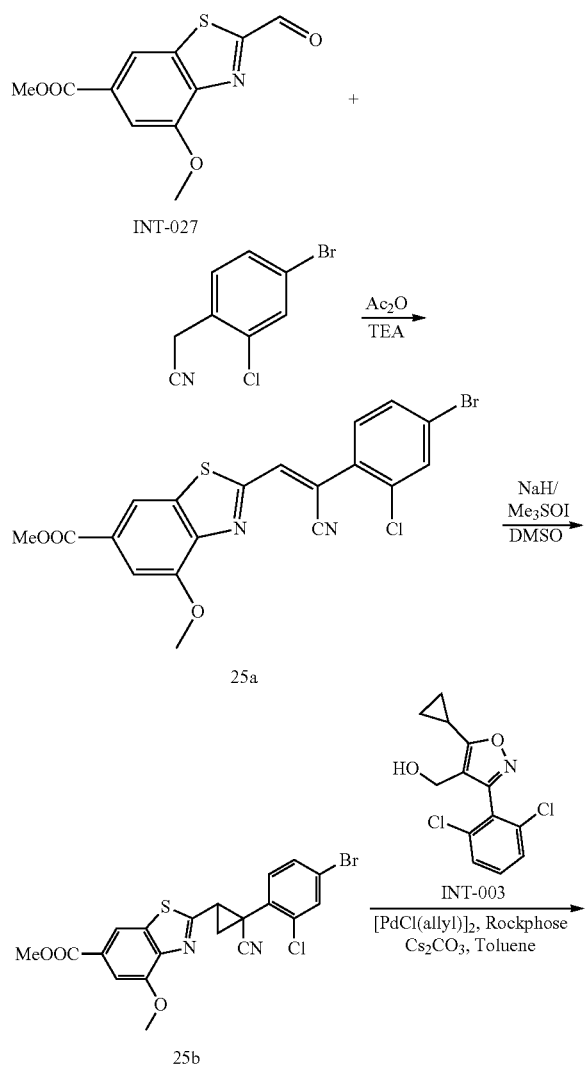

Experimental Details for Compound VII-06 (Scheme 25)

Methyl 2-[(1Z)-2-(4-bromo-2-chlorophenyl)-2-cyanoeth-1-en-1-yl]-4-methoxy-1,3-benzothiazole-6-carboxylate (Compound 25a)

To a solution of Compound INT-027 (80 mg, 0.32 mmol) in acetyl acetate (2 mL) was added 2-(4-bromo-2-chlorophenyl) acetonitrile (73 mg, 0.32 mmol) and triethylamine (97 mg, 0.96 mmol). The resulting solution was stirred 16 h at 120° C. The resulting mixture was concentrated under vacuum. This residue was applied onto a silica gel column with ethyl acetate/petroleum ether (27:73). This resulted in 110 mg (74%) of the title compound as a yellow solid. LC-MS (ESI, m/z): $[M+H]^+=463.0$.

Methyl 2-[2-(4-bromo-2-chlorophenyl)-2-cyanocyclopropyl]-4-methoxy-1,3-benzothiazole-6-carboxylate (Compound 25b)

To a suspension of sodium hydride (11.1 mg, 0.46 mmol) in DMSO (2 mL) was added S, S-dimethylmethanesulfinyl iodide (60 mg, 0.27 mmol) batchwise at room temperature. The mixture was stirred for 1 h at this temperature, then Compound 25a (110 mg, 0.24 mmol) was added one portion. The resulting solution was stirred for another 4 h at room temperature. The reaction was then quenched by the addition of water. The resulting solution was extracted with ethyl acetate and the organic layers were combined. The mixture was dried over anhydrous sodium sulfate and concentrated under vacuum. This residue was applied onto a silica gel column with ethyl acetate/petroleum ether (12:88). This resulted in 40 mg (35%) of the title compound as a yellow solid. LC-MS (ESI, m/z): $[M+H]^+=477.0$.

Methyl 2-[2-(2-chloro-4-[[5-cyclopropyl-3-(2,6-dichlorophenyl)-1,2-oxazol-4-yl]methoxy] phenyl)-2-cyanocyclopropyl]-4-methoxy-1,3-benzothiazole-6-carboxylate (Compound 25c)

To a solution of Compound 25b (40 mg, 0.08 mmol) in toluene (1 mL) was added Compound INT-003 (29 mg, 0.10 mmol), [PdCl(allyl)]₂ (1.2 mg, 0.003 mmol), RockPhose (4 mg, 0.008 mmol) and cesium carbonate (78 mg, 0.24 mmol). The resulting mixture was stirred for 3 h at 80° C. under N₂ atmosphere. The resulting mixture was concentrated under vacuum. This residue was applied onto a silica gel column with ethyl acetate/petroleum ether (1:3). This resulted in 20 mg (35%) of the title compound as a yellow solid. LC-MS (ESI, m/z): [M+H]⁺=680.0.

2-[2-(2-Chloro-4-[[5-cyclopropyl-3-(2,6-dichlorophenyl)-1,2-oxazol-4-yl]methoxy] phenyl)-2-cyanocyclopropyl]-4-methoxy-1,3-benzothiazole-6-carboxylic Acid (Compound VII-06)

To a solution of Compound 25c (20 mg, 0.03 mmol) in a mixed solvent of THF (1 mL) and methanol (1 mL) was added a solution of sodium hydroxide (6 mg, 0.15 mmol) in water (1 mL). The resulting solution was stirred for 1 h at 50° C. The pH value of the solution was adjusted to 6-7 with hydrogen chloride (2 N) after cooling to room temperature. The resulting mixture was concentrated under vacuum. The residue was applied onto a silica gel column with dichloromethane/ethyl acetate (56:44). This resulted in 1.6 mg (8%) of the title compound as a yellow solid.

LC-MS (ESI, m/z): [M+H]⁺=666.0. ¹HNMR (300 MHz, CDCl₃, ppm): δ 8.31 (s, 1H), 7.62-7.48 (m, 5H), 7.09-7.08 (m, 1H), 6.90-6.79 (m, 1H), 5.10-4.85 (m, 2H), 4.22 (s, 1H), 4.01 (s, 3H), 3.80-3.77 (m, 1H), 2.70-2.60 (m, 1H), 2.30-2.20 (m, 1H), 1.20-1.10 (m, 4H).

Following the procedure described above for Scheme 22 and 25 and substituting the appropriate reagents, starting materials and purification methods known to those skilled in the art, the following compounds of the present invention were prepared.

TABLE 7

| Compound | Structure | Scheme | LC-MS (M + H)⁺ | ¹HNMR (ppm) |
|---|---|---|---|---|
| VII-01 | 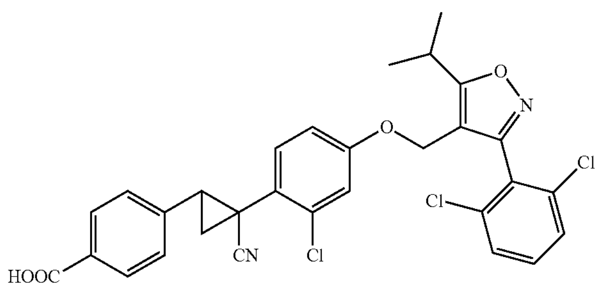 [SMILES: CC(C)c1onc(-c2c(Cl)cccc2Cl)c1COc1ccc(C2(C#N)CC2c2ccc(C(=O)O)cc2)c(Cl)c1] | 22 | 583.2 | DMSO-d₆: δ 13.00 (s, 1H), 7.97-7.95 (m, 2H), 7.64-7.49 (m, 6H), 7.04-6.78 (m, 2H), 4.91 (s, 2H), 3.77-3.44 (m, 2H), 2.92-2.86 (m, 1H), 2.04-1.99 (m, 1H), 1.34 (d, J = 6.9 Hz, 6H). |
| VII-04 | 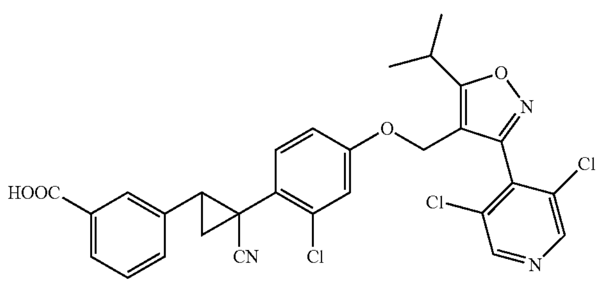 [SMILES: CC(C)c1onc(-c2c(Cl)cncc2Cl)c1COc1ccc(C2(C#N)CC2c2cccc(C(=O)O)c2)c(Cl)c1] | 22 | 580.1 | CDCl₃: δ 8.61-8.57 (m, 2H), 8.15-8.08 (m, 1H), 8.08-8.06 (m, 1H), 7.67-7.65 (m, 1H), 7.53-7.51 (m, 1H), 7.30-7.26 (m, 1H), 6.90-6.86 (m, 1H), 6.69-6.66 (m, 1H), 4.83 (s, 2H), 2.72-2.67 (m, 1H), 2.21-2.03 (m, 2H), 1.91-1.89 (m, 1H), 1.34-1.26 (m, 2H), 1.26-1.21 (m, 2H). |
| VII-07 | 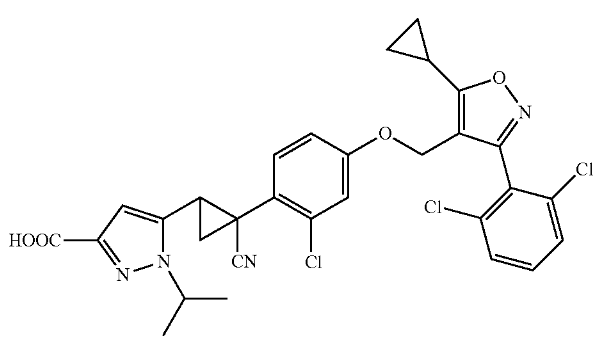 [SMILES: CC(C)n1nc(C(=O)O)cc1C1CC1(C#N)c1ccc(OCc2c(-c3c(Cl)cccc3Cl)noc2C2CC2)cc1Cl] | 25 | 611.1 | CDCl₃: δ 7.43-7.35 (m, 3H), 7.31-7.20 (m, 1H), 6.90-6.86 (m, 2H), 6.76-6.73 (m, 1H), 4.83 (s, 3H), 2.53-2.50 (m, 1H), 2.19-2.12 (m, 1H), 2.10-1.98 (m, 2H), 1.71-1.61 (m, 3H), 1.60-1.50 (m, 3H), 1.35-1.25 (m, 2H), 1.23-1.20 (m, 2H). |

TABLE 7-continued

| Compound | Structure | Scheme | LC-MS (M + H)+ | ¹HNMR (ppm) |
|---|---|---|---|---|
| VII-08 | 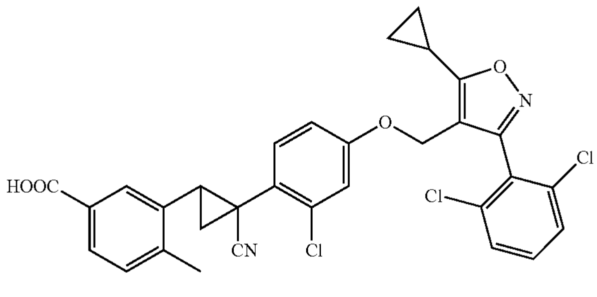 [SMILES: Cc1ccc(C(=O)O)cc1C1CC1(C#N)c1ccc(OCc2c(-c3c(Cl)cccc3Cl)noc2C2CC2)cc1Cl] | 25 | 593.0 | DMSO-d$_6$: δ 12.92 (s, 1H), 7.86-7.81 (m, 2H), 7.63-7.53 (m, 4H), 7.43-7.41 (m, 1H), 7.09-7.08 (m, 1H), 6.87-6.84 (m, 1H), 4.96 (s, 2H), 3.13-3.09 (m, 1H), 2.56 (s, 3H), 2.50-2.49 (m, 1H), 2.29-2.25 (m, 1H), 1.86-1.82 (m, 1H), 1.21-1.19 (m, 2H), 1.19-1.17 (m, 2H). |
| VII-09 | 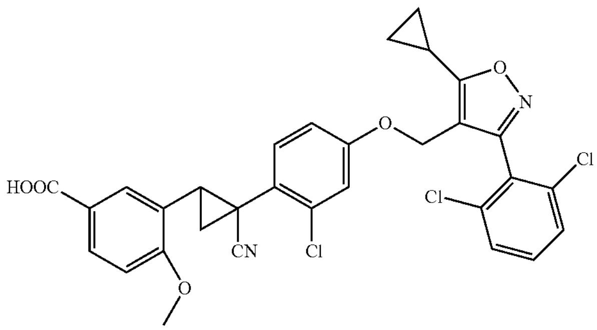 [SMILES: COc1ccc(C(=O)O)cc1C1CC1(C#N)c1ccc(OCc2c(-c3c(Cl)cccc3Cl)noc2C2CC2)cc1Cl] | 25 | 609.0 | DMSO-d$_6$: δ 12.78 (s, 1H), 7.98-7.96 (m, 1H), 7.79-7.78 (m, 1H), 7.67-7.53 (m, 3H), 7.23-7.21 (m, 1H), 7.06-7.05 (m, 1H), 6.91-6.88 (m, 1H), 4.95 (s, 2H), 4.00 (s, 3H), 3.00-2.96 (m, 1H), 2.50-2.49 (m, 1H), 2.33-2.27 (m, 1H), 1.74-1.70 (m, 1H), 1.19-1.17 (m, 2H), 1.16-1.12 (m, 2H). |
| VII-10 | 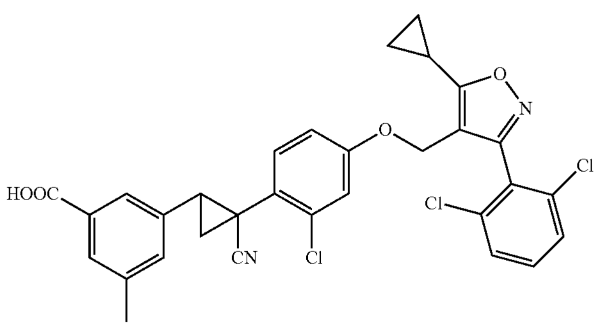 [SMILES: Cc1cc(C(=O)O)cc(C2CC2(C#N)c2ccc(OCc3c(-c4c(Cl)cccc4Cl)noc3C3CC3)cc2Cl)c1] | 25 | 595.1 | DMSO-d$_6$: δ 13.04 (brs, 1H), 7.85 (s, 1H), 7.73 (s, 1H), 7.64-7.62 (m, 2H), 7.57-7.51 (m, 3H), 7.06 (d, J = 2.4 Hz, 1H), 6.84-6.81 (m, 1H), 4.96 (s, 2H), 2.91-2.87 (m, 1H), 2.51-2.50 (m, 1H), 2.41 (s, 3H), 2.41-2.40 (m, 1H), 1.99-1.95 (m, 1H), 1.23-1.19 (m, 4H). |

Chiral Separation for Compound VII-03-1 and VII-03-2

3-[2-(2-Chloro-4-[[5-cyclopropyl-3-(2,6-dichlorophenyl)-1,2-oxazol-4-yl]methoxy] phenyl)-2-cyanocyclopropyl] benzoic Acid (Compound VII-03-1 and VII-03-2)

3.7 g Compound VII-03 (96% purity) was separated by Chiral-Prep-HPLC with the following conditions: (Prep-LAB 100G-YMC): Column, CHIRAL ART Cellulose-SB S-5 um, 2*25 cm, 5 um; Mobile Phase, Hexane (1% HOAc) and ethanol (hold 50.0% ethanol in 15 min); Detector, UV 254/220 nm. The fractions from the first peak was concentrated by lyophilization. This resulted in 1.24 g of Compound VII-03-1 as a white solid. The resulted product from second peak was purified by reversed column with CH$_3$CN/Water (0.05% HCl) (7:3). This resulted in 1.03 g of Compound VII-03-2 as a white solid.

Compound VII-03-1:

Rt=4.62 min, ee %=99.9%. LC-MS (ESI, m/z): [M+H]$^+$= 579.3. ¹H NMR (400 MHz, DMSO-d$_6$, ppm): δ 13.06 (s, 1H), 8.6 (s, 1H), 7.93-7.91 (m, 1H), 7.74-7.72 (m, 1H), 7.64-7.62 (m, 2H), 7.57-7.51 (m, 3H), 7.07-7.06 (m, 1H), 6.85-6.82 (m, 1H), 4.97 (s, 2H), 2.95-2.91 (m, 1H), 2.50-2.40 (m, 2H), 2.00-1.99 (m, 1H), 1.23-1.12 (m, 4H).

Compound VII-03-2:

Rt=5.81 min, ee %=99.8%. LC-MS (ESI, m/z): [M+H]$^+$= 579.3. ¹H NMR (400 MHz, DMSO-d$_6$, ppm): δ 13.04 (s, 1H), 8.6 (s, 1H), 7.92-7.90 (m, 1H), 7.74-7.72 (m, 1H), 7.64-7.62 (m, 2H), 7.57-7.51 (m, 3H), 7.07-7.06 (m, 1H), 6.85-6.82 (m, 1H), 4.96 (s, 2H), 2.95-2.91 (m, 1H), 2.50-2.40 (m, 2H), 2.01-1.99 (m, 1H), 1.21-1.19 (m, 4H).

Biological Assays

The compounds of the present technology may be assayed using the following procedures and show or will be shown to have FXR binding activity.

FXR Transactivation Assay

Reagents:

HEK293T pGL4.35 [luc2P/9XGAL4 UAS/Hygro]

pBIND-FXR Vector

DMEM medium, high glucose

Fetal Bovine Serum (FBS, heat-inactivated)

Penicillin-Streptomycin (10000 U/ml, 100 ml)
DMEM, High Glucose, HEPES, no Phenol Red
Opti-MEM® I Reduced Serum Medium
Steady-Glo™ Luciferase Assay System
TransIT-293 Transfection Reagent
GW4064 as a positive control
Process:
1. Hek293T cells were plated at $1.1*10^6$/ml into a 100 mm dish.
2. Cells were transfected with 8.4 μg of pBind-FXR, 1.26 μg of the reporter vector pGL4.35 (Promega). Cells were incubated at 37° C. under 5% CO2 atmosphere.
3. All of compounds were 3-fold serial diluted from 10 mM stock for 10 doses in DMSO.
4. Transfer compound dilutions into 384 well assay plates using liquid workstation.
5. Seed 25 ul HEK293T cells into 384 well assay plate (prepared step 4) at $0.6*10^5$/ml. Cells were incubated at 37° C. under 5% CO2 atmosphere overnight.
6. Add 25 ul steady-Glo™ Luciferase Assay Reagent into each well of 384-well assay plate.
7. Record the luminescence value on Envision 2104 plate reader.
8. Calculate EC50 by fitting % Activity values and log of compound concentrations to nonlinear regression (dose response–variable slope) with Graphpad 5.0.

FXR Coactivator Assay
Reagents:
LanthaScreen™ TR-FRET Farnesoid X Receptor Coactivator Assay
GW4064 as a positive control
Process:
1. All of compounds were 3-fold serial diluted from 10 mM stock for 10 doses in DMSO.
2. Dilute each 100× agonist serial dilution to 2× using Complete Coregulator buffer G.
3. Transfer 10 μl of each of the 2× agonist serial dilutions to 384 well assay plates.
4. Add 5 μl of 4×FXR-LBD to 384 well assay plates.
5. Add 5 μl of 4× peptide/4× antibody solution to 384 well assay plates.
6. Incubate at room temperature protected from light.
7. Read the plate at wavelengths of 520 nm and 495 nm on Envision 2104 plate reader.
8. Calculate the TR-FRET ratio by dividing the emission signal at 520 nm by the emission signal at 495 nm.
9. Calculate EC50 by fitting % Activity values and log of compound concentrations to nonlinear regression (dose response–variable slope) with Graphpad 5.0.

The present compounds exhibit superior activity in both the coactivator assay and the transactivation assay, compared to other non-substituted cyclopropyl-based FXR modulators, possibly due to enhanced interaction of the substituted cyclopropyl moiety with the target. In some embodiments, the present compounds exhibit more than an order of magnitude better activity than the known non-substituted cyclopropyl-based FXR modulators. In addition, the present compounds display better solubility and ADME profiles than other non-substituted cyclopropyl-based FXR modulators. In some embodiments, the present compounds are more stable and less toxic than, e.g., FXR modulators that include the stilbene moiety. Selected present compounds are evaluated in mouse disease model of liver fibrosis and NASH. Superior in vivo efficay, e.g., improvement of ALT/AST liver enzymes, liver fibrosis and NASH score, is observed with the present compounds compared to non-substituted cyclopropyl-based FXR modulators.

TABLE 8

| Compound | FXR Transactivation Assay ($EC_{50}$) | FXR Coactivator Assay ($EC_{50}$) |
| --- | --- | --- |
| IV-01 | C | B |
| IV-02 | B | A |
| IV-03 | B | A |
| IV-04 | B | — |
| IV-05 | A | A |
| IV-05-1 | A | A |
| IV-05-2 | B | A |
| IV-06 | A | A |
| IV-06-1 | B | — |
| IV-06-2 | A | — |
| IV-07 | C | — |
| IV-08 | B | — |
| IV-09 | B | — |
| IV-10 | B | — |
| IV-11 | A | — |
| IV-12 | C | — |
| IV-13 | — | A |
| IV-14 | C | — |
| IV-15 | B | A |
| IV-16 | B | — |
| IV-17 | B | — |
| IV-18 | — | C |
| IV-19 | — | B |
| IV-20 | B | A |
| V-01 | C | A |
| V-02 | B | A |
| V-03 | C | — |
| V-04 | C | — |
| V2-01 | — | C |
| VI-01 | B | A |
| VI-02 | A | A |
| VI-03 | A | — |
| VI-04 | A | A |
| VI-05 | A | A |
| VI-06 | A | — |
| VI-07 | B | — |
| VI-08 | A | — |
| VI-09 | A | — |
| VI-10 | — | B |
| VI-11 | A | — |
| VI-12 | A | — |
| VI-13 | A | — |
| VII-01 | C | A |
| VII-02 | B | A |
| VII-03 | A | A |
| VII-03-1 | B | A |
| VII-03-2 | A | A |
| VII-04 | B | — |
| VII-05 | C | — |
| VII-06 | B | — |
| VII-07 | C | — |
| VII-08 | A | — |
| VII-09 | B | — |
| VII-10 | A | — |

A: $EC_{50}$ = 10 nM to 100 nM;
B: $EC_{50}$ = 101 nM-400 nM
C: $EC_{50}$ = 401 nM-5 uM

EQUIVALENTS

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A compound according to formula (II):

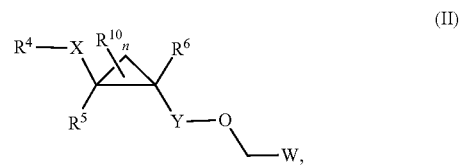

stereoisomers, and/or salts thereof; wherein
W is

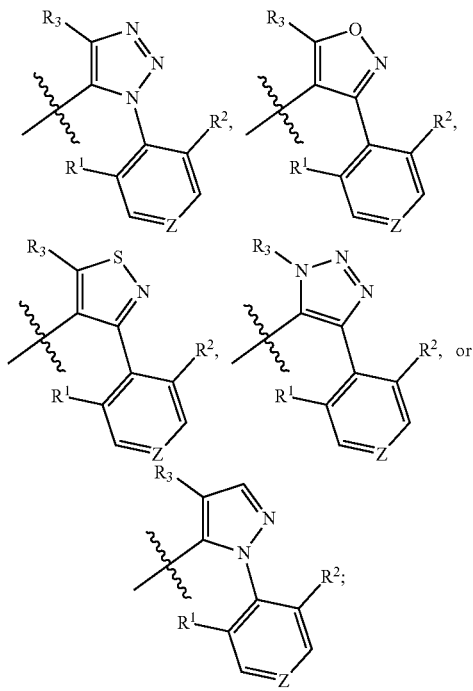

X is a substituted or unsubstituted aryl or heteroaryl group;

Y is a substituted or unsubstituted phenyl or pyridyl group;

Z is CH or N;

$R^1$ and $R^2$ are independently H, OH, halo, CN, carboxyl, $NR^aR^b$, or a substituted or unsubstituted alkyl, alkoxy, or hydroxyalkyl group;

$R^3$ is a substituted or unsubstituted alkyl or cycloalkyl group;

$R^4$ is CN, $SO_3H$, $CONR^aR^b$, $SO_2NR^aR^b$, $NHSO_2R^b$, $SO_2NHCOR^a$, $CO_2R^c$, or a substituted or unsubstituted tetrazolyl or 1,2,4-oxadiazol-5(4H)-one-3-yl group;

$R^5$ is CN or $C_1$-$C_3$ alkyl group and $R^6$ is H; $R^5$ is H and $R^6$ is CN or $C_1$-$C_3$ alkyl group; or $R^5$ and $R^6$ are independently CN or $C_1$-$C_3$ alkyl group;

$R^{10}$ at each occurrence is independently halo, or a substituted or unsubstituted alkyl, alkoxy, cycloalkyl, or fluorinated cycloalkyl group;

$R^a$ at each occurrence is independently H, or a substituted or unsubstituted alkyl, haloalkyl, cycloalkyl, aryl, alkylene-$R^d$, or $SO_2$-alkyl group;

$R^b$ at each occurrence is H or a substituted or unsubstituted alkyl, or haloalkyl group;

$R^c$ is H or a substituted or unsubstituted alkyl, alkenyl, alkynyl, or cycloalkyl group;

$R^d$ is $CO_2H$, OH, or $SO_3H$;

$R^g$ and $R^h$ at each occurrence are independently H or a substituted or unsubstituted $C_1$-$C_6$ alkyl group; and n is 0, 1, 2, 3, or 4.

2. The compound of claim 1 wherein W is

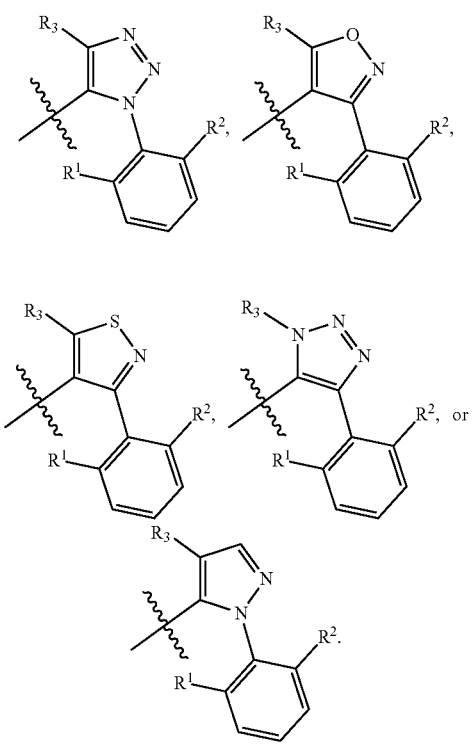

3. The compound of claim 1 wherein W is

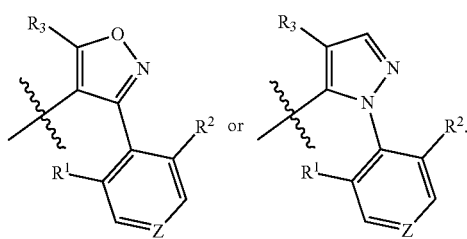

4. The compound of claim 1, wherein Z is N.

5. The compound of claim 1, wherein W is

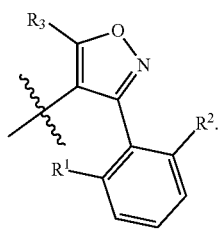

6. The compound of claim 1, wherein $R^4$ is $CO_2H$, $CONH_2$, $SO_2NH_2$, or a substituted or unsubstituted $CO_2$—$C_1$-$C_6$ alkyl, $CO_2$—$C_3$-$C_6$ cycloalkyl, CONH—$C_1$-$C_6$ alkyl, CONH—$C_3$-$C_6$ cycloalkyl, or NH—$SO_2$—$C_1$-$C_6$ alkyl group.

7. The compound of claim 6, wherein $R^4$ is $CO_2H$, $CONH_2$, or a substituted or unsubstituted $CO_2$—$C_1$-$C_6$ alkyl, or CONH—$C_1$-$C_6$ alkyl group.

8. The compound of claim 6, wherein $R^4$ is $CO_2H$ or CONH—$C_1$-$C_6$ alkyl wherein the C1-C6 alkyl is substituted with $SO_3H$.

9. The compound of claim 1, wherein Y is a phenyl or pyridyl group substituted with one or two substituents independently selected from the group consisting of $C_1$-$C_6$ alkyl, $C_3$-$C_6$ cycloalkyl, $C_1$-$C_6$ haloalkyl, and halo.

10. The compound of claim 9, wherein Y is phenyl group substituted with one or two substituents independently selected from the group consisting of F, Cl, and $CF_3$ groups.

11. The compound of claim 1, wherein $R^1$ and $R^2$ are independently H, halo, CN, $CO_2H$, $NR^eR^f$, or a substituted or unsubstituted $C_1$-$C_6$ alkyl, $C_1$-$C_6$ alkoxy, or $C_1$-$C_6$ hydroxyalkyl group; and wherein $R^e$ and $R^f$ at each occurrence are independently H or a substituted or unsubstituted $C_1$-$C_6$ alkyl group.

12. The compound of claim 11, wherein $R^1$ and $R^2$ are independently H, F, Cl, CN, $NR^eR^f$, or a substituted or unsubstituted $C_1$-$C_3$ alkyl, $C_1$-$C_3$ alkoxy, or $C_1$-$C_3$ hydroxyalkyl group.

13. The compound of claim 11, wherein $R^1$ and $R^2$ are independently H, F, Cl $OCHF_2$, $OCF_3$, CN, $NH_2$, $CH_3$, $CH_2NH_2$, or $OCH_3$.

14. The compound of claim 11, wherein $R^1$ and $R^2$ are both Cl, or $R^1$ is H and $R^2$ is Cl, $OCF_3$ or $OCHF_2$.

15. The compound of claim 1, wherein $R^3$ is a substituted or unsubstituted $C_1$-$C_6$ alkyl or $C_3$-$C_6$ cycloalkyl group.

16. The compound of claim 15, wherein $R^3$ is $CH_3$, $CH_2CH_3$, $CH(CH_3)_2$, $CH_2CH(CH_3)_2$, $CH(CH_2CH_3)_2$, $CH(CH_2CH_3)(CH_3)$, $C(CH_3)_3$, or cyclopropyl.

17. The compound of claim 1, wherein $R^5$ is CN or $CH_3$; and $R^6$ is H.

18. The compound of claim 1, wherein $R^6$ is CN or $CH_3$; and $R^5$ is H.

19. The compound of claim 1, wherein the compound has the structure IIIA:

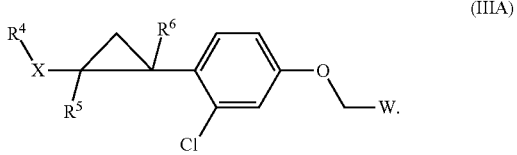

(IIIA)

20. The compound of claim 1, wherein X is

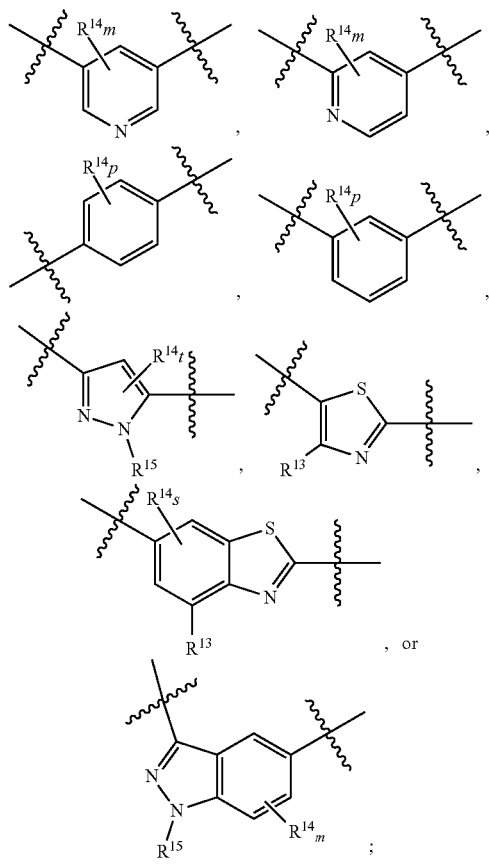

wherein:
$R^{13}$ is H, halo, or a substituted or unsubstituted $C_1$-$C_6$ alkyl, or O—($C_1$-$C_6$ alkyl) group;
$R^{14}$ at each occurrence is independently halo, $CF_3$, or a substituted or unsubstituted alkyl, or alkoxy group;
$R^{15}$ is H or a substituted or unsubstituted $C_1$-$C_6$ alkyl group;
m is 0, 1, 2, or 3;
p is 0, 1, 2, 3, or 4;
s is 0, 1, or 2; and
t is 0 or 1.

21. The compound of claim 20, wherein $R^{13}$ is an unsubstituted O—($C_1$-$C_3$ alkyl) group.

22. The compound of claim 20 wherein m, p, s, or t is 0.

23. A composition comprising the compound of claim 1 and a pharmaceutically acceptable carrier.

24. A pharmaceutical composition comprising an effective amount of the compound of claim 1 for treating a liver disease selected from the group consisting of primary biliary cirrhosis (PBC), cerebrotendinous xanthomatosis (CTX), primary sclerosing cholangitis (PSC), nonalcoholic fatty liver disease (NAFLD), nonalcoholic steatohepatitis (NASH), liver fibrosis, and liver cirrhosis.

25. A method for treating a liver disease selected from the group consisting of primary biliary cirrhosis (PBC), cerebrotendinous xanthomatosis (CTX), primary sclerosing cholangitis (PSC), nonalcoholic fatty liver disease (NAFLD), nonalcoholic steatohepatitis (NASH), liver fibrosis, and liver cirrhosis comprising administering an effective amount of a compound of claim 1, or administering a pharmaceutical composition comprising an effective amount of a compound of claim 1, to a subject in need thereof.

26. A method for activating FXR comprising contacting FXR with an effective amount of a compound of claim 1.

27. The compound of claim 9, wherein the $C_1$-$C_6$ haloalkyl substituent is $CF_3$.

* * * * *